(12) United States Patent
Miller, III et al.

(10) Patent No.: US 8,398,296 B2
(45) Date of Patent: Mar. 19, 2013

(54) MAGNETICALLY COUPLED SYSTEM FOR MIXING

(75) Inventors: Harlan Miller, III, Fort Myers, FL (US);
George Meichel, Fort Myers, FL (US);
Edward Legere, Lake Worth, FL (US);
Edwin Malkiel, Naples, FL (US);
Robert Paul Woods, Naples, FL (US);
Oliver Ashley, Fort Myers, FL (US);
Joseph Katz, Baltimore, MD (US);
Jason Ward, Fort Myers, FL (US); Paul Petersen, West Palm Beach, FL (US)

(73) Assignee: Algenol Biofuels Inc., Bonita Springs, FL (US)

( * ) Notice: Subject to any disclaimer, the term of this patent is extended or adjusted under 35 U.S.C. 154(b) by 0 days.

(21) Appl. No.: 13/405,012

(22) Filed: Feb. 24, 2012

(65) Prior Publication Data
US 2012/0220027 A1    Aug. 30, 2012

Related U.S. Application Data

(60) Provisional application No. 61/447,004, filed on Feb. 25, 2011, provisional application No. 61/575,644, filed on Aug. 24, 2011.

(51) Int. Cl.
*B01F 13/08* (2006.01)
*B01F 3/04* (2006.01)

(52) U.S. Cl. .......... 366/273; 366/102; 366/332; 261/81; 261/120

(58) Field of Classification Search .......... 366/273, 366/274, 255, 256, 257, 259, 260, 101, 102, 366/103, 332; 261/81, 120
See application file for complete search history.

(56) References Cited

U.S. PATENT DOCUMENTS

| | | | | | |
|---|---|---|---|---|---|
| 2,097,002 | A | * | 10/1937 | Thaller | 378/134 |
| 3,206,172 | A | * | 9/1965 | Brejcha et al. | 366/273 |
| 4,287,062 | A | * | 9/1981 | von Nordenskjold | 261/120 |
| 4,465,377 | A | * | 8/1984 | de Bruyne | 366/273 |
| 4,498,785 | A | * | 2/1985 | de Bruyne | 366/274 |
| 4,534,656 | A | * | 8/1985 | de Bruyne | 366/247 |
| 4,549,812 | A | * | 10/1985 | Bothorel et al. | 366/142 |
| 4,560,521 | A | * | 12/1985 | Walling et al. | 264/437 |
| 4,759,635 | A | * | 7/1988 | MacMichael et al. | 366/274 |
| 4,760,028 | A | * | 7/1988 | deBruyne et al. | 435/302.1 |
| 4,797,212 | A | * | 1/1989 | von Nordenskjold | 261/121.1 |
| 4,828,706 | A | * | 5/1989 | Eddleman | 210/644 |
| 4,960,521 | A | * | 10/1990 | Keller | 210/644 |
| 5,028,142 | A | * | 7/1991 | Ostoich et al. | 366/273 |
| 5,078,504 | A | * | 1/1992 | Landa et al. | 366/118 |
| 5,089,179 | A | * | 2/1992 | von Nordenskjold | 261/81 |
| 5,762,418 | A | * | 6/1998 | Van Drie | 366/332 |

(Continued)

FOREIGN PATENT DOCUMENTS
WO    WO 2005/121310    12/2005

OTHER PUBLICATIONS

Weissman et al., "Photobioreactor Design: Mixing, Carbon Utilization, and Oxygen Accumulation," Biotechnology and Bioengineering 31: 336-344 (1988).

(Continued)

*Primary Examiner* — Tony G Soohoo
(74) *Attorney, Agent, or Firm* — Lawrence B. Ebert; David J. Lorenz

(57) ABSTRACT

The invention provides a mixing system comprising a magnetically coupled drive system and a foil for cultivating algae, or cyanobacteria, in an open or enclosed vessel. The invention provides effective mixing, low energy usage, low capital expenditure, and ease of drive system component maintenance while maintaining the integrity of a sealed mixing vessel.

4 Claims, 49 Drawing Sheets

U.S. PATENT DOCUMENTS

| | | | | |
|---|---|---|---|---|
| 6,382,827 | B1* | 5/2002 | Gebrian | 366/274 |
| 6,467,946 | B1* | 10/2002 | Gebrian | 366/273 |
| 6,663,276 | B2* | 12/2003 | Yale | 366/273 |
| 6,733,171 | B2* | 5/2004 | Schob | 366/273 |
| 7,513,680 | B2* | 4/2009 | Reusche et al. | 366/273 |
| 7,566,164 | B2* | 7/2009 | Zarom | 366/289 |
| 7,824,904 | B1 | 11/2010 | Dimanshteyn | |
| 7,832,922 | B2* | 11/2010 | Schoeb | 366/273 |
| 2006/0118494 | A1* | 6/2006 | Rundt et al. | 210/695 |
| 2007/0045194 | A1* | 3/2007 | Reusche et al. | 210/695 |
| 2009/0035856 | A1 | 2/2009 | Galliher et al. | |
| 2009/0130757 | A1 | 5/2009 | Terentiev | |
| 2009/0142827 | A1* | 6/2009 | Schoeb | 435/302.1 |
| 2009/0219780 | A1 | 9/2009 | Castillo | |
| 2011/0003366 | A1 | 1/2011 | Zeikus | |
| 2012/0220027 | A1* | 8/2012 | Miller et al. | 366/273 |

OTHER PUBLICATIONS

Zhang et al., "Microbioreactors for Bioprocess Development," Journal of the Association for Laboratory Automation 12:143-151 (2007).

Boon et al., "Comparing a Range of Impellers for 'Stirring as Foam Disruption'," Biochemical Engineering Journal 10:183-195 (2002).

Bouaifi et al., "Power Consumption, Mixing Time and Homogenisation Energy in Dual-Impeller Agitated Gas-Liquid Reactors," Chemical Engineering and Processing 40:87-95 (2001).

Chaumont et al., "Biotechnology of Algal Biomass Production: A Review of Systems for Outdoor Mass Culture," Journal of Applied Phycology 5:593-604 (1993).

Chisti et al., "Oxygen Transfer and Mixing in Mechanically Agitated Airlift Bioreactors," Biochemical Engineering Journal 10:143-153 (2002).

Laws et al., "A Simple Algal Production System Designed to Utilize the Flashing Light Effect," Biotechnology and Bioengineering 15:2319-2335 (1983).

Laws et al., "High Algal Production Rates Achieved in a Shallow Outdoor Flume," Biotechnology and Bioengineering 28: 191-197 (1986).

Mears, "Design, Construction and Testing of Pilot Scale Photobioreactor Subsystems," Master of Science (MS) Thesis, Ohio University, Mechanical Engineering (Engineering and Technology), pp. 1-88 (2008).

Nienow et al., "The Versatility of Up-Pumping Hydrofoil Agitators," Chemical Engineering Research and Design 82:1073-1081 (2004).

Ogbanna et al., "A Novel Internally Illuminated Stirred Tank Photobioreactor for Large-Scale Cultivation of Photosynthetic Cells," Journal of Fermentation and Bioengineering 82:61-67 (1996).

Ugwu et al., "Photobioreactors for Mass Cultivation of Algae," Bioresource Technology 99:4021-4028 (2008).

Vrabel et al., "Mixing in Large-Scale Vessels Stirred With Multiple Radial or Radial and Axial Up-Pumping Impellers: Modelling and Measurements," Chemical Engineering Science 55:5881-5896 (2000).

* cited by examiner

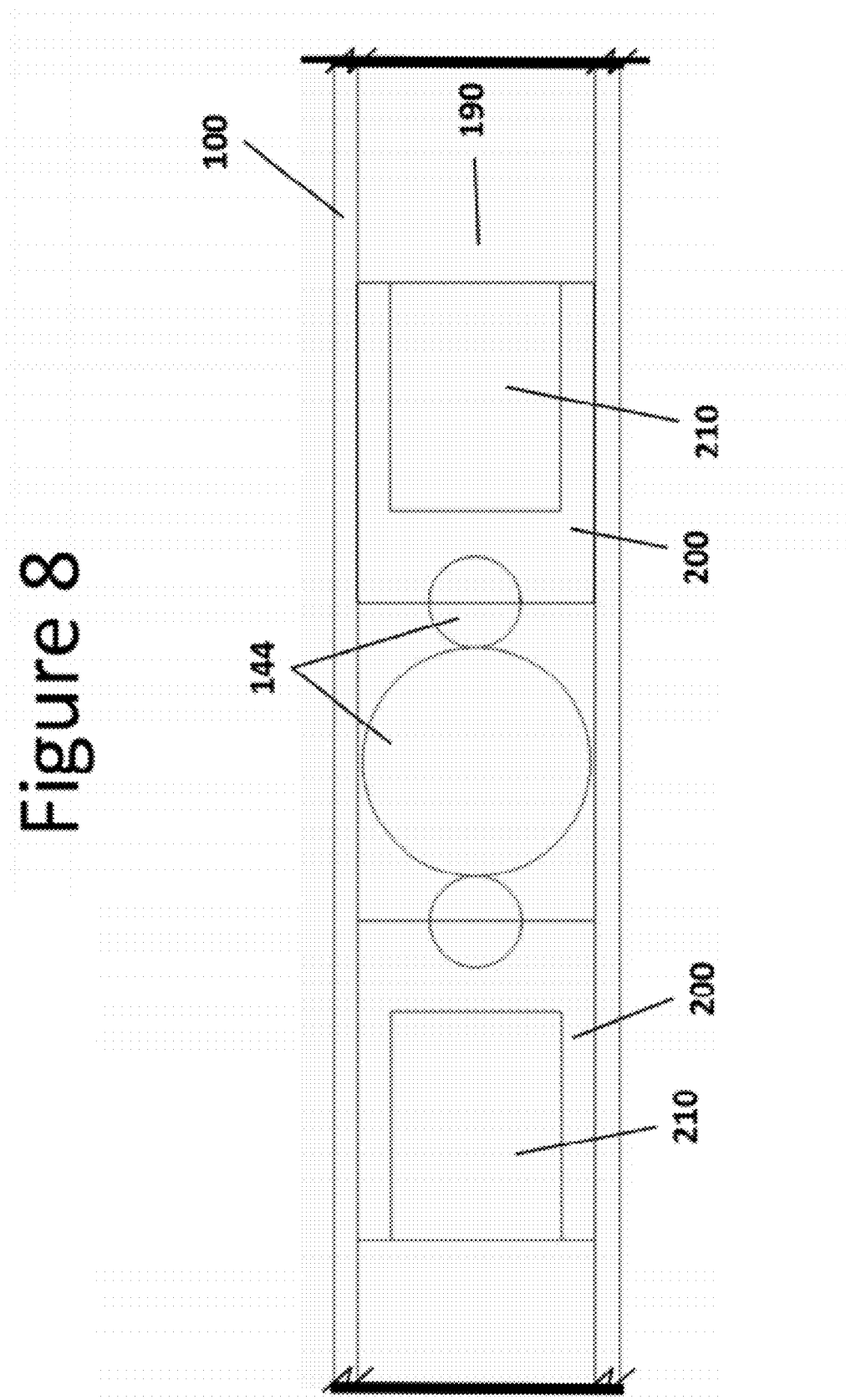

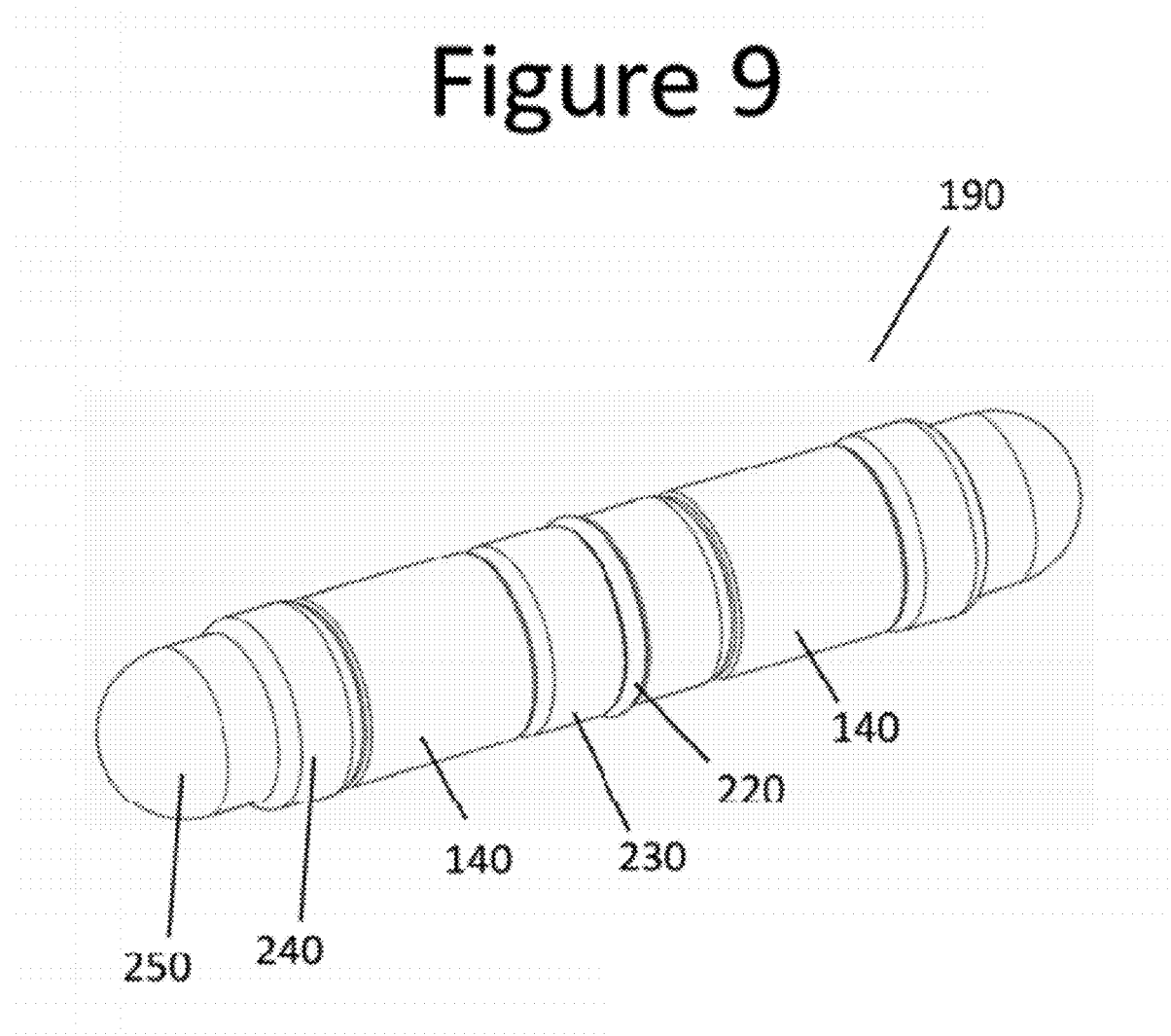

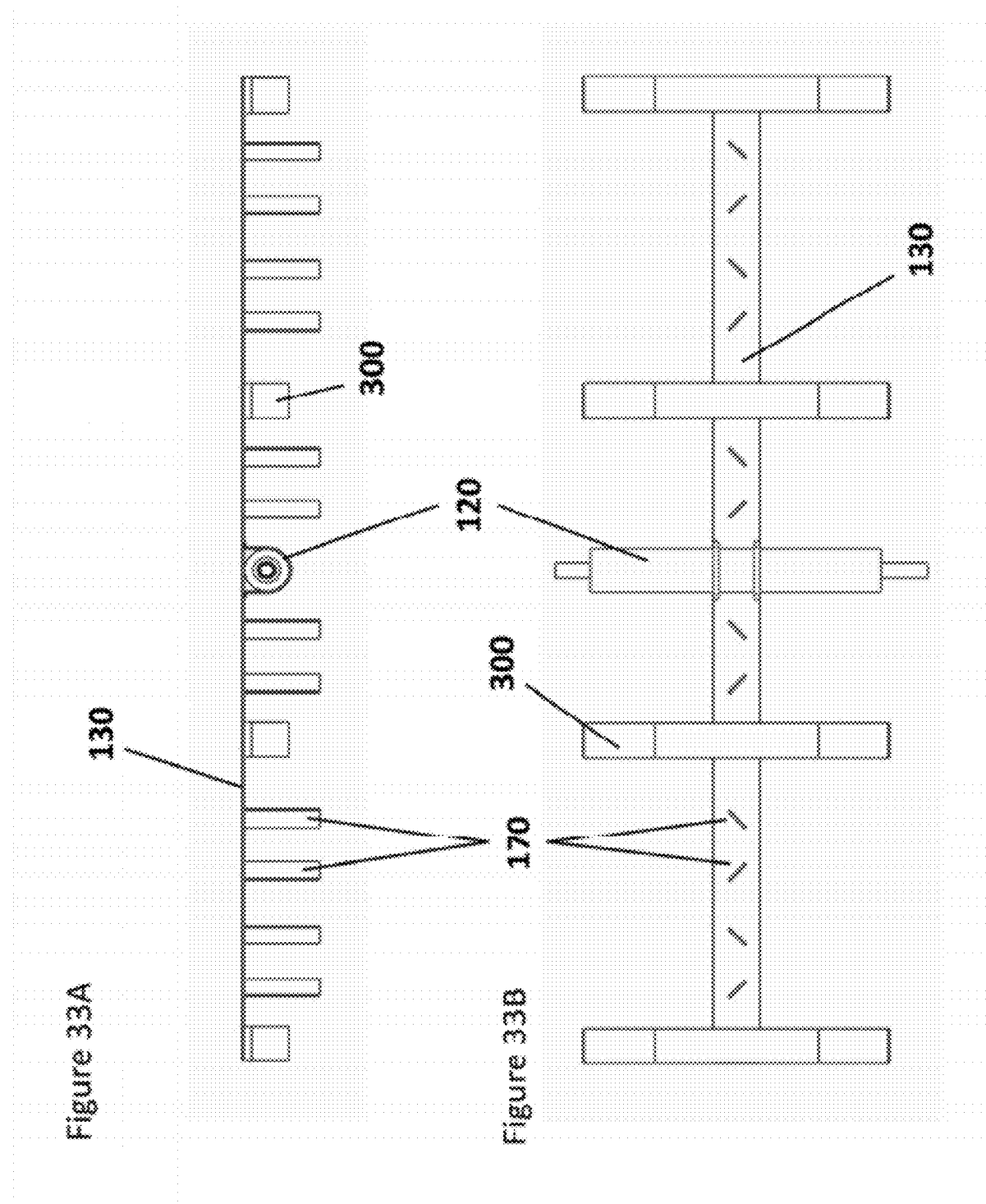

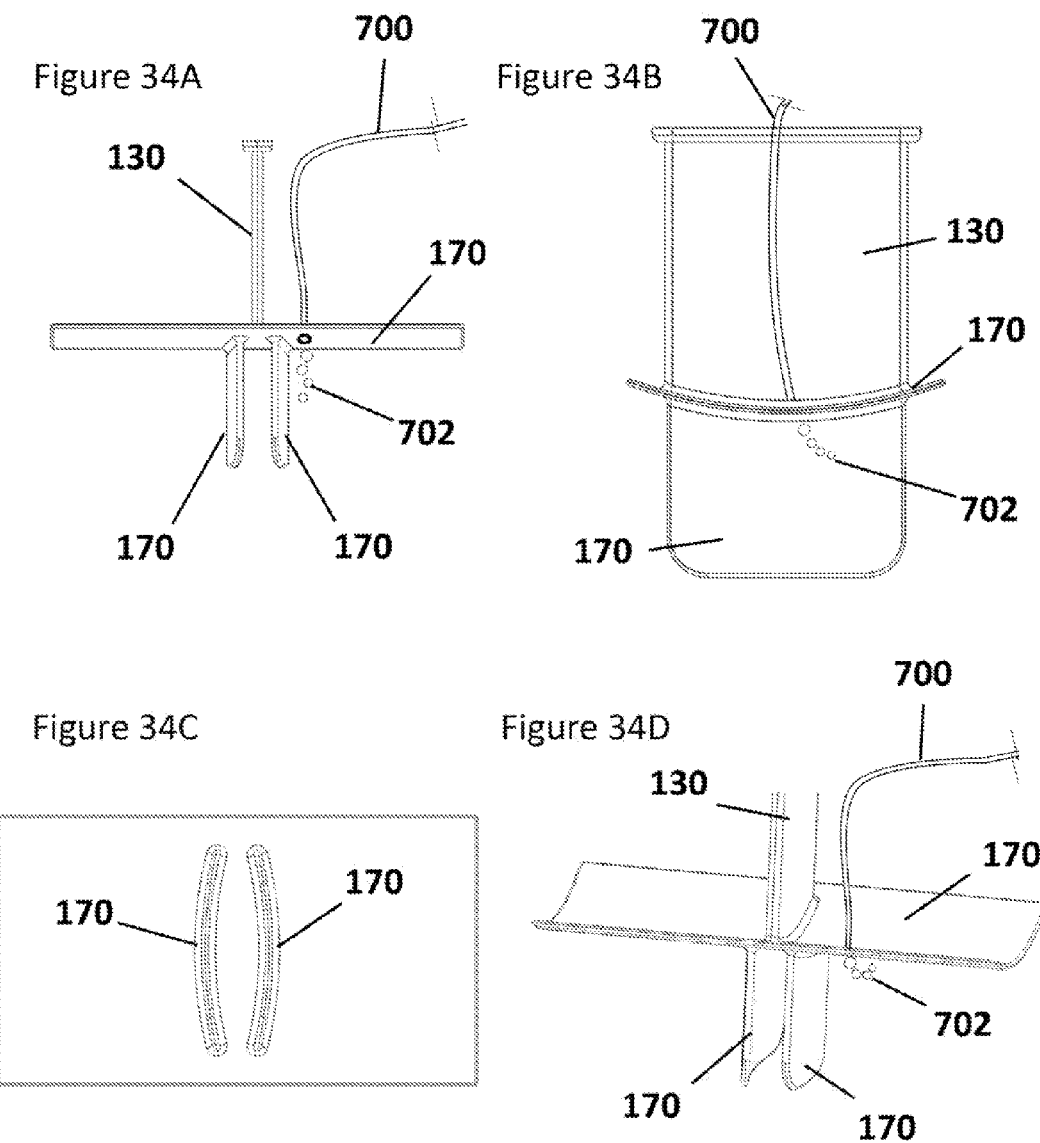

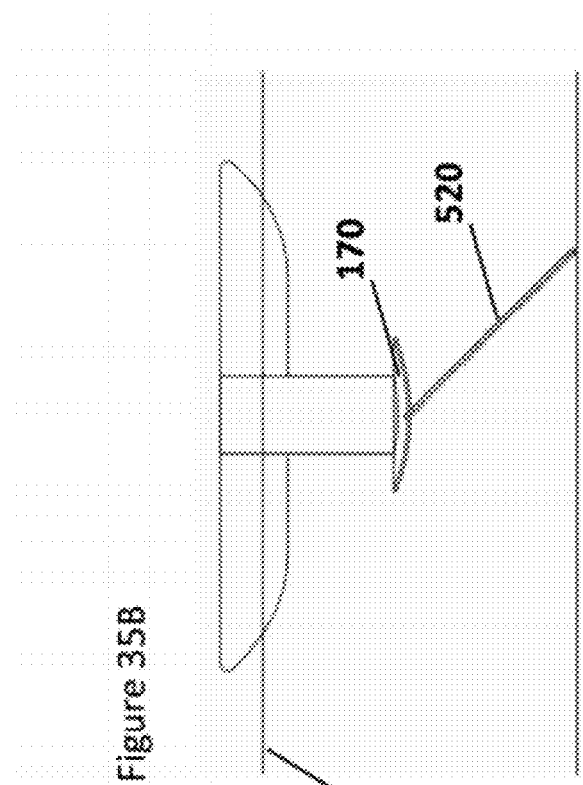
Figure 35A
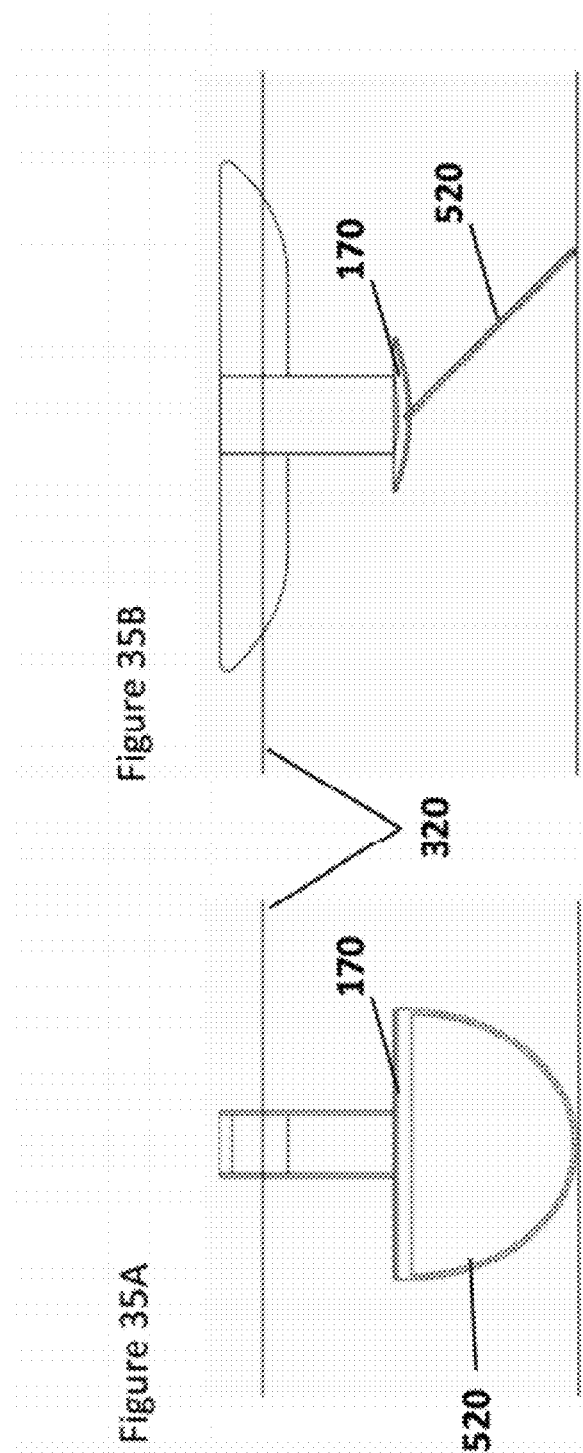
Figure 35B
Figure 35C
Figure 35D

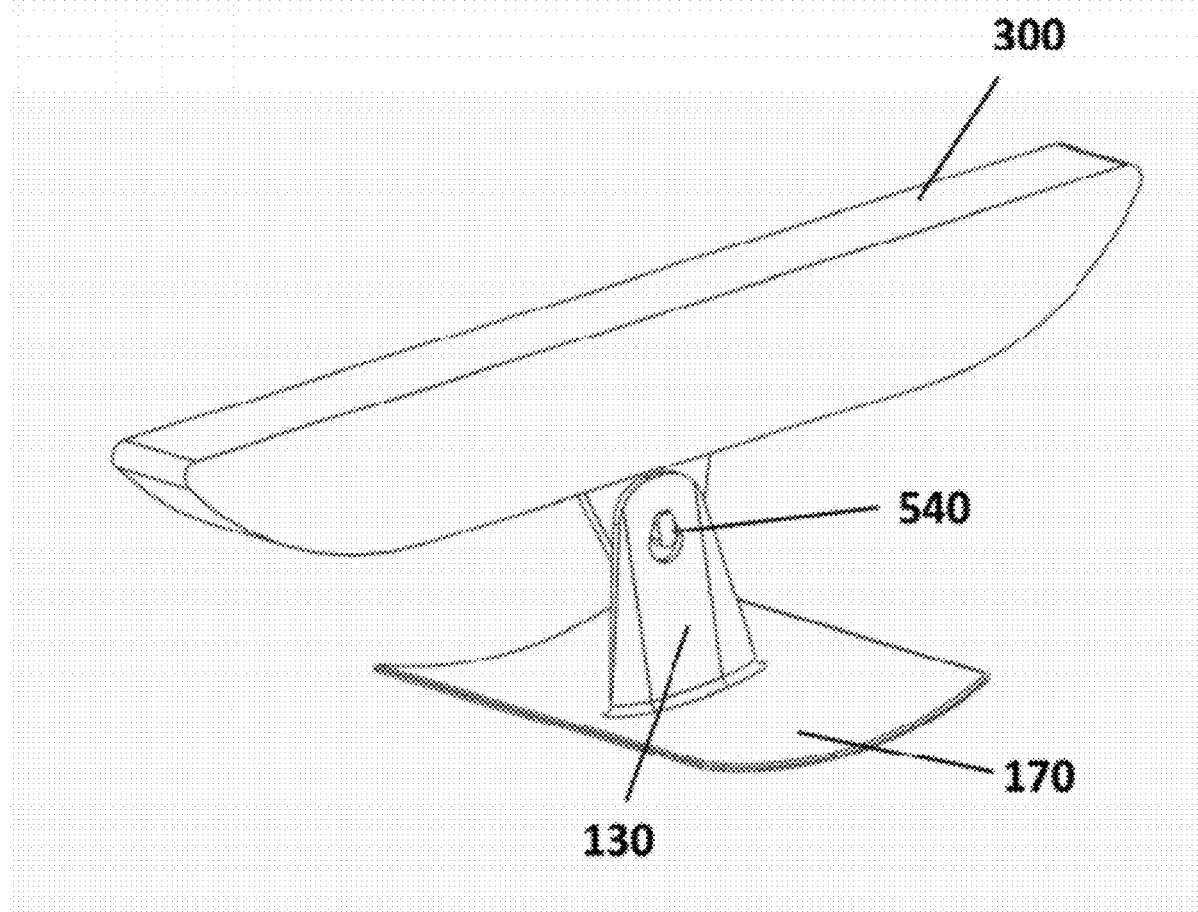

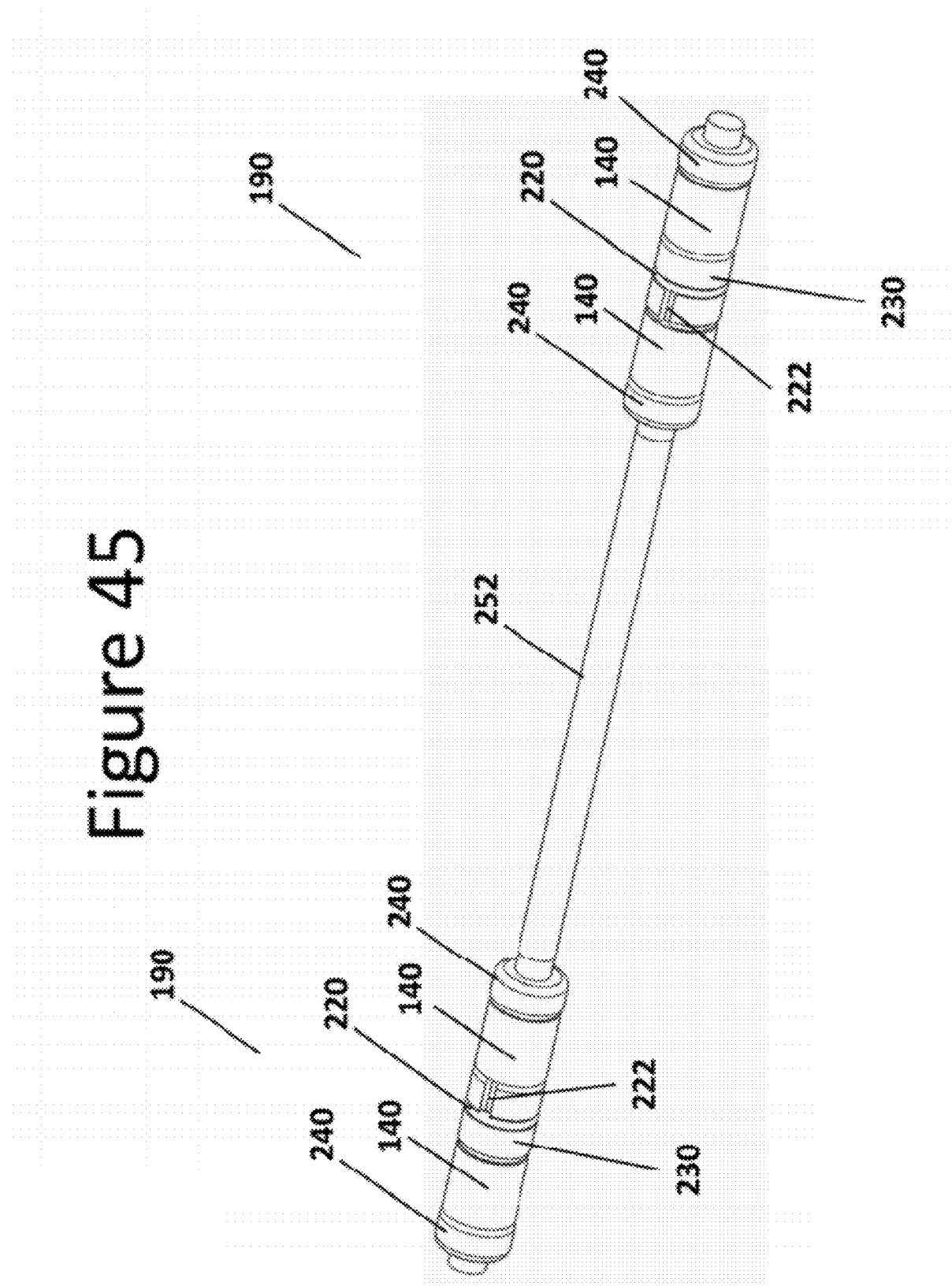

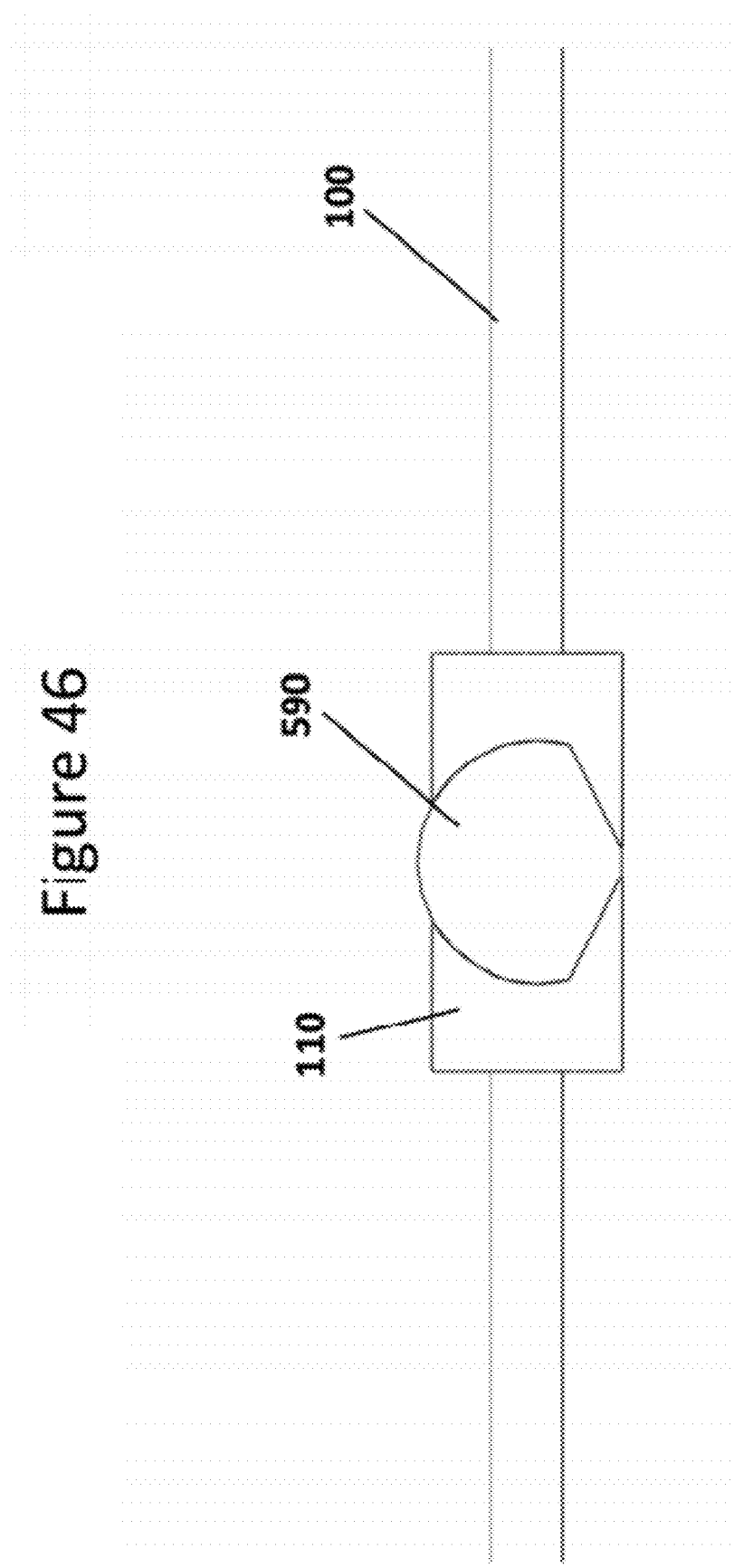

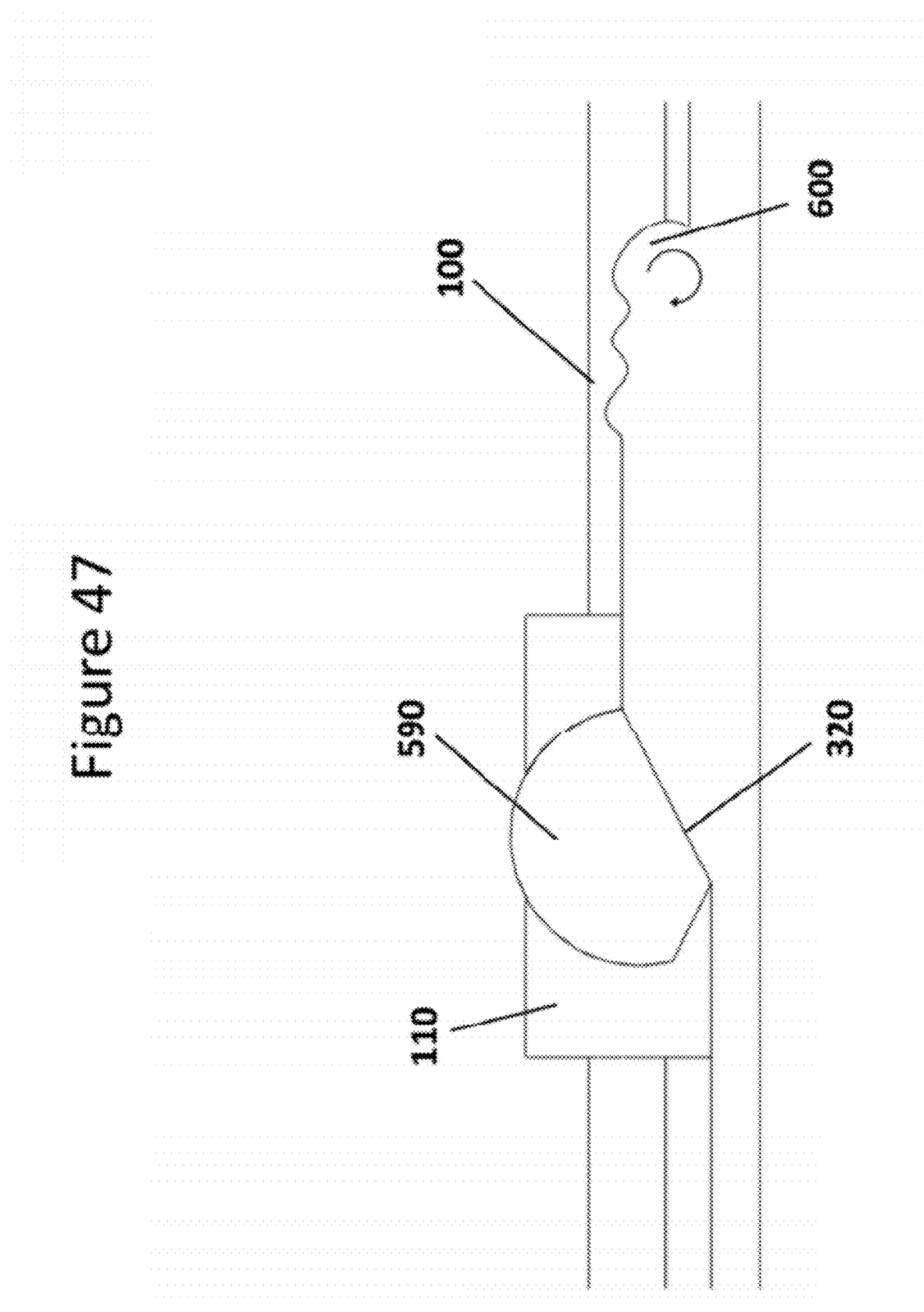

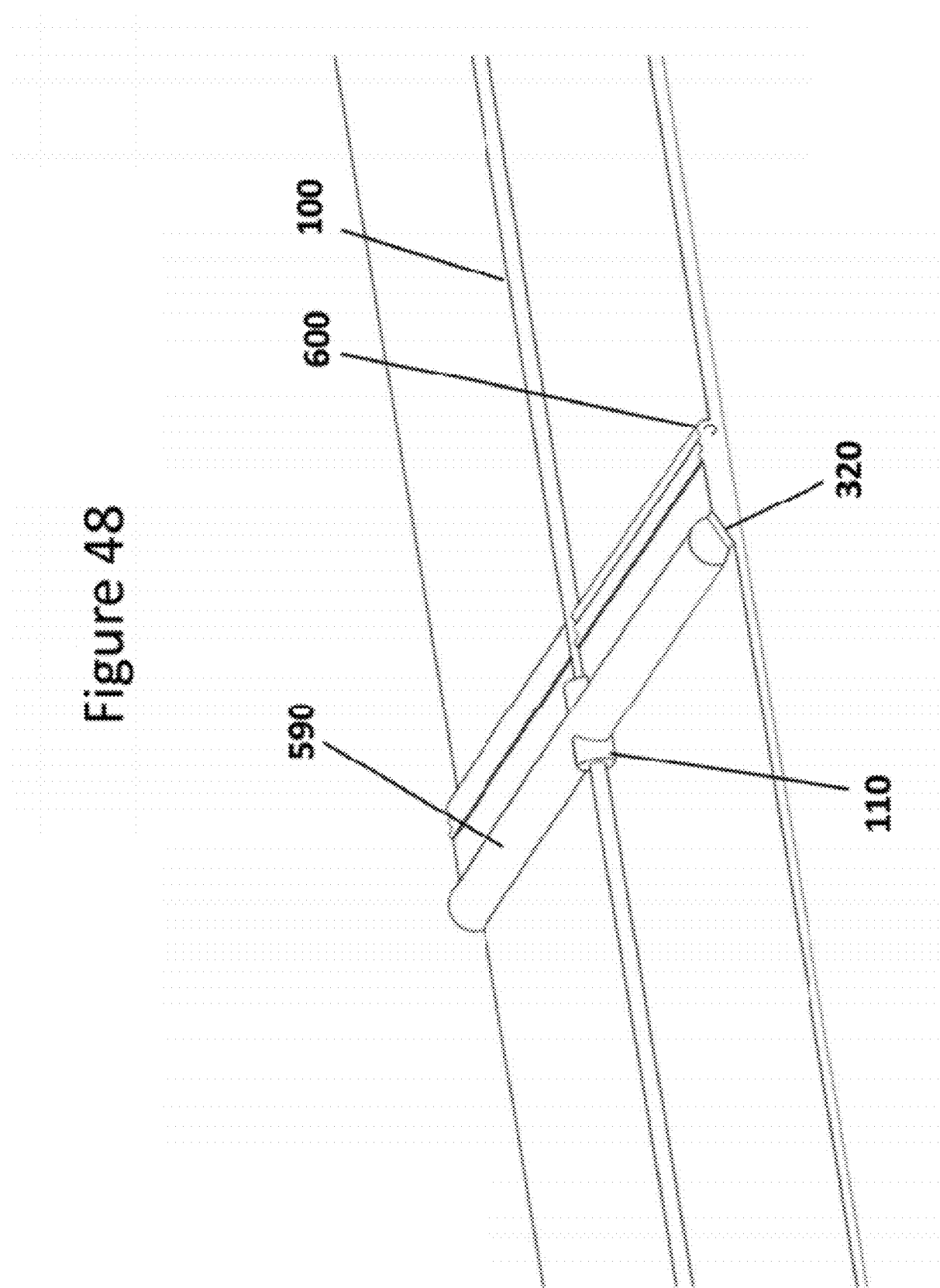

MAGNETICALLY COUPLED SYSTEM FOR MIXING

CROSS-REFERENCE TO RELATED APPLICATIONS

This application claims the benefit of U.S. Provisional Patent Application No. 61/447,004, filed Feb. 25, 2011, and U.S. Provisional Patent Application No. 61/575,644, filed Aug. 24, 2011, the disclosures of each of which are incorporated herein by reference.

BACKGROUND

The present invention relates generally to mixing systems for use in enclosed vessels, such as rigid or flexible enclosures, or open vessels, such as pond systems, which may serve as reactors, bioreactors or photobioreactors. Systems in accordance with the present invention may be used to cultivate algae and other microorganisms in water for purposes such as producing biofuels, bulk chemicals, pharmaceutical compounds or other products or treating wastewater.

High density, high pigment aqueous algae cultures require mixing to evenly distribute nutrients to microorganisms in the culture and to ensure that the microorganisms in the culture are cyclically exposed to light needed for photosynthesis. One of the key challenges for commercial-scale mixing systems is to minimize the use of energy and capital expense while providing optimal production conditions.

Large, open pond systems typically use large paddle wheel mixers to move water around a raceway, but paddle wheel mixers are inefficient and require significant energy inputs, which may be cost-prohibitive for use in cultivation of microorganisms for the production of biofuel or other commodities. In addition, paddle wheel mixers are designed to move water in a path of horizontal flow and do not effectively move algae in a vertical plane, which is needed to ensure even exposure of the algae to light at the surface of the aqueous culture.

In "Biotechnology of Algal Biomass Production: A Review of Systems for Outdoor Mass Culture," Journal of Applied Phycology 5: 593-604 (1993), Chaumont reviews mixing techniques proposed for use with algae cultures, including forcing culture through a slit in a board dragged through an open pond; "a mixing system consisting of a continuous flume containing arrays of foils similar in design to segments of airplane wings"; airlift; injectors; propellers; pump and gravity flow devices using natural energy sources; open pond loop "raceways" incorporating paddlewheel stirring devices; and sloped ponds and other cultivation units having parallel troughs or baffles, for example.

In "Photobioreactors for Mass Cultivation of Algae," Bioresource Technology 99: 4021-4028 (2008), Ugwu et al. note that inefficient stirring mechanisms in open cultivation systems yield poor mass transfer rates that result in low biomass productivity.

Vertical photobioreactor systems use pumps, blowers or compressed air to introduce rising air bubbles and produce turbulent fluid motion in the aqueous algal culture for the purpose of mixing. Horizontal photobioreactor systems typically use pumps to circulate the culture and create turbulence in the aqueous algae culture to provide mixing.

Ugwu et al. ("Photobioreactors for Mass Cultivation of Algae") describe the use of air-pump, bubble column and airlift systems to mix cultures in tubular and vertical-column photobioreactors.

The effects and performance of mixing in vessels such as bioreactors have also been investigated for numerous configurations of other mixing elements, such as the combination of radial impellers with axial up-pumping hydrofoils (Vrabel et al., "Mixing in Large-Scale Vessels Stirred With Multiple Radial or Radial and Axial Up-Pumping Impellers: Modelling and Measurements," Chemical Engineering Science, Vol. 55, No. 23: 5881-5896 (2000)); a rotating impeller in combination with glass tubes acting as baffle plates (Ogbanna et al., "A Novel Internally Illuminated Stirred Tank Photobioreactor for Large-Scale Cultivation of Photosynthetic Cells," Journal of Fermentation and Bioengineering, Vol. 82, No. 1:61-67 (1996)); up-pumping impellers (Nienow et al., "The Versatility of Up-Pumping Hydrofoil Agitators," Chemical Engineering Research and Design, Vol. 82, No. 9: 1073-1081 (2004)); axial and mixed dual-impeller systems (Bouaifi et al., "Power Consumption, Mixing Time and Homogenisation Energy in Dual-Impeller Agitated Gas-Liquid Reactors," Chemical Engineering and Processing, Vol. 40, No. 2: 87-95 (2001)); the combination of airlift with hydrofoil impellers (Chisti et al., "Oxygen Transfer and Mixing in Mechanically Agitated Airlift Bioreactors," Biochemical Engineering Journal, Vol. 10, No. 2: 143-153 (2002)); and turbines, down-pumping hydrofoils and up-pumping hydrofoils (Boon et al., "Comparing a Range of Impellers for 'Stirring as Foam Disruption'," Biochemical Engineering Journal, Vol. 10, No. 3: 183-195 (2002)).

In "A Simple Algal Production System Designed to Utilize the Flashing Light Effect," Biotechnology and Bioengineering, Vol. XXV: 2319-2335 (1983) and in "High Algal Production Rates Achieved in a Shallow Outdoor Flume," Biotechnology and Bioengineering, Vol. XXVIII: 191-197 (1986), Laws et al. describe gains in solar energy conversion efficiency and algae production yielded by emplacing arrays of foils similar in design to airplane wings to create vortices and systematic mixing in an algal culture flume.

Many of these methods provide mixing regimes for high-density algae cultures but consume too much energy to be cost effective in the production of biofuel, bulk chemicals or other commodities on an industrial scale. The required energy inputs for such methods and configurations exceed the energy yield that can be produced by the algae culture in the form of, for example, biofuel. Accordingly, a need exists for a mixing system that provides sufficient mixing and gas transfer for optimal production of biofuel and other materials while maintaining acceptable energy consumption in the context of operating costs for the reactor system and minimizing capital expense.

In addition, a need exists to provide effective mixing and gas transfer in vessels such as bioreactors and photobioreactors while maintaining structural integrity of the vessel, minimizing risk of contamination of the contents of the vessel, minimizing exposure of pumps and other mixing drive system components to corrosive agents in the vessel and facilitating ease of maintaining the drive system components. Various mixing apparatuses rely on the use of rotary impellers and similar elements that are not physically connected to a drive motor but instead are driven by magnetic coupling.

U.S. Pat. No. 7,824,904 (Dimanshteyn for "Photobioreactors for Production of Algae and Methods Therefor") discloses mixing a liquid microbial culture using a rotary or oscillatory system comprising one or more motors, one or more shafts connected to the one or more motors and a plurality of mixing blades attached to the one or more shafts.

U.S. Pat. Appl. Pub. No. 2009/0035856 (Galliher et al. for "Continuous Perfusion Bioreactor System") discloses vessels such as a disposable, collapsible bag having an integrated magnetically-driven rotating impeller that provides mixing for cell culture, cell containment, bioreactor and/or pharmaceutical manufacturing systems.

U.S. Pat. Appl. Pub. No. 2009/0130757 (Terentiev for "Bioreactor With Mixer and Sparger") discloses a bioreactor that comprises an impeller positioned within an interior compartment of the vessel that is rotated by way of a magnetic coupling.

U.S. Pat. Appl. Pub. No. 2011/0003366 (Zeikus for "Methods of Using Pneumatic Bioreactors") discloses a pneumatic bioreactor containing a fluid to be mixed that includes a floating impeller that rises in the fluid as gas bubbles carry it upward to the surface and falls when the gas is then vented, wherein the mixing speed is controlled with electromagnets in the vessel acting upon magnetic material in the impeller or its guides.

PCT Published Patent Application WO 2005/121310 (Johnson et al. for "Creation of Shear in a Reactor") discloses the use of a applying a magnetic field to a magnetically-activated element to generate shear in a liquid sample.

U.S. Pat. Appl. Pub. No. 2009/0219780 (Castillo et al. for "Mixing System Including a Flexible Bag, Specific Flexible Bag and Locating System for the Mixing System") discloses a mixing system comprising a flexible bag with a rotary magnetic impeller and an alignment facilitation device adapted to facilitate alignment between the magnetic impeller and a magnetic driver located external to the system.

In "Design, Construction and Testing of Pilot Scale Photobioreactor Subsystems," Master of Science (MS) Thesis, Ohio University, Mechanical Engineering (Engineering and Technology), 2008, Mears describes the work of Tsygankov (2001) involving a coaxial cylinder reactor in which two coaxial tubes are placed one inside the other with algae fluid located in the annular space between the surfaces of both tubes. Mears further describes the reactor of Tsygankov incorporating a ferromagnetic ring in the section containing the algae and applying a magnetic field to move the ring back and forth, mixing the algae liquid.

In "Microbioreactors for Bioprocess Development," Journal of the Association for Laboratory Automation, Vol. 12, No. 3: 143-151 (2007), Zhang et al. describe the use of a magnetic stir bar to mix a microbial solution in a cylindrical reactor chamber.

A need exists to incorporate a magnetic coupling drive system with a mixing configuration that is effective in a photobioreactor while maintaining the structural integrity of the photobioreactor and ability to service the components of the drive system without compromising the algae culture therein.

The above discussion includes both information known to the art prior to the filing date and information forming part of the present inventive disclosure. Inclusion of any statement in this section, whether as a characterization of a published reference or in a discussion of technical problems and their solutions, is not to be taken as an admission that such statement is prior art.

SUMMARY OF INVENTION

An object of this invention is a magnetically coupled mixing system adapted to provide vertical mixing in an open or enclosed vessel while advantageously maintaining low energy usage requirements.

A further object of this invention is a magnetically coupled mixing system adapted to provide gas transfer in an open or enclosed vessel while advantageously maintaining low energy usage requirements.

A further object of this invention is a magnetically coupled mixing system wherein components used to drive the mixing system are located outside a sealed mixing vessel, permitting access outside the sealed mixing vessel for greater ease of maintaining the drive components, while maintaining the integrity of the sealed mixing vessel.

Accordingly, this invention provides for a magnetically coupled mixing system comprising a mixing vessel; a liquid mixture disposed within the reactor vessel; a drive conduit; a drive element disposed within the drive conduit and adapted to move in a longitudinal direction within the drive conduit; a follower member having a first distal end and a second distal end, wherein the follower member is disposed around the perimeter of the drive conduit and is adapted to move longitudinally along the drive conduit; a magnetic follower element disposed within the follower member, wherein the magnetic follower element is adapted to couple magnetically with the drive element and is proximally disposed outside the drive conduit; a foil having a surface shaped or configured to provide hydrodynamic lift, wherein the foil is disposed at least partially in the liquid mixture; and a support member connecting the foil and the follower member.

This invention also provides for a magnetically coupled mixing system comprising a mixing vessel; a liquid disposed within the mixing vessel; a gas disposed within the mixing vessel; a drive conduit; a drive element disposed within the drive conduit and adapted to move in a longitudinal direction within the drive conduit; a follower member having a first distal end and a second distal end, wherein the follower member is disposed around the perimeter of at least a portion of the drive conduit and is adapted to move longitudinally along the drive conduit; a magnetic follower element disposed within the follower member, wherein the magnetic follower element is adapted to couple magnetically with the drive element and is proximally disposed outside the drive conduit; and a crossbar attached to the follower member, wherein the crossbar is at least partially disposed in the liquid, the crossbar mixes the liquid, the gas, or an interface between the liquid and the gas, the crossbar has a surface shaped or configured to generate a breaking wave front in the liquid, and the breaking wave front is generated by movement of the crossbar along a linear path in the mixing vessel.

This invention also provides for a magnetically coupled mixing system comprising drive fluid contained within the drive conduit and a pump in communication with the drive conduit, wherein the pump is adapted to move the drive fluid and the drive element within the drive conduit.

This invention also provides for a magnetically coupled mixing system wherein the drive fluid is air, water, mineral oil or polyethylene glycol.

This invention also provides for a magnetically coupled mixing system wherein the drive fluid contains corrosion-inhibiting agents.

This invention also provides for a magnetically coupled mixing system wherein the pump is a reversible flow pump.

This invention also provides for a magnetically coupled mixing system wherein the pump is a positive displacement pump or a velocity pump.

This invention also provides for a magnetically coupled mixing system wherein the pump is a diaphragm pump or a centrifugal pump.

This invention also provides for a magnetically coupled mixing system comprising a flow control valve.

This invention also provides for a magnetically coupled mixing system wherein the pump is located outside of the mixing vessel.

This invention also provides for a magnetically coupled mixing system wherein the mixing vessel is an enclosed vessel, an open vessel, a reactor, a bioreactor, a photobioreactor or an open pond. In the context of a photobioreactor comprising cells in a liquid suspension, the magnetic mixing system of the present invention employing a linearly moving foil provides gentle vertical mixing which allows for particle distribution and movement within a light field but without damaging cells. For situations wherein the cells are producing a target molecule, the cost of the energy consumed by the mixing system of the present invention is less than the value of the target molecule, with energy consumed and molecules produced averaged over the same time period. In a preferred embodiment, the energy cost is 10% or less of the value of the target molecules produced.

This invention also provides for a magnetically coupled mixing system wherein the liquid mixture comprises algae and water. This invention also provides for a magnetically coupled mixing system that may be used in other commercial processes that require low energy input and regular, gentle mixing in elongate reactors, including but not limited to pharmaceutical cell culture, food processing and waste water treatment. This invention also provides for a magnetically driven skimmer that can economically remove surface solids that accumulate in algal ponds and waste water. This invention also provides for a magnetically driven foil that may be used in a vapor phase to increase the efficiency of a solar still.

This invention also provides for a magnetically coupled mixing system wherein the drive conduit is disposed inside the reactor vessel.

This invention also provides for a magnetically coupled mixing system wherein the drive conduit is disposed at least partially within the liquid mixture.

This invention also provides for a magnetically coupled mixing system wherein the drive conduit is disposed outside the reactor vessel.

This invention also provides for a magnetically coupled mixing system comprising a blocking element disposed within the drive conduit, wherein the blocking element is adapted to restrict the movement of the drive element within a desired range within the drive conduit.

This invention also provides for a magnetically coupled mixing system comprising a longitudinal vane disposed on an inner surface of the drive conduit such that channels adopted to permit flow of the drive fluid are formed on the inner surface of the drive conduit, wherein the channels are bounded by the surface of the drive element, the surface of the longitudinal vane and the inner surface of the elongate tubular hollow member.

This invention also provides for a magnetically coupled mixing system comprising a longitudinal groove formed in an inner surface of the drive conduit such that a channel adapted to permit flow of the drive fluid is formed in the inner surface of the drive conduit, wherein the channel are bounded by the surface of the drive element and the surfaces of the groove formed in the inner surface of the drive conduit.

This invention also provides for a magnetically coupled mixing system wherein the drive element is ferromagnetic or magnetic.

This invention also provides for a magnetically coupled mixing system comprising materials that suppress corrosion or wear, wherein the materials coat the drive element.

This invention also provides for a magnetically coupled mixing system wherein the drive element is spherical or cylindrical.

This invention also provides for a magnetically coupled mixing system wherein the follower member comprises a hollow elongate tubular enclosure.

This invention also provides for a magnetically coupled mixing system wherein the magnetic follower element is adapted to move longitudinally within the follower member.

This invention also provides for a magnetically coupled mixing system comprising a flotation member and a support member connecting the flotation member with the follower member or the foil.

This invention also provides for a magnetically coupled mixing system wherein the flotation member is configured to provide surface mixing of the liquid mixture.

This invention also provides for a magnetically coupled mixing system wherein the flotation member comprises a pontoon.

This invention also provides for a magnetically coupled mixing system comprising a tracking member, wherein the tracking member is proximal to a wall of the mixing vessel and is adapted to prevent the foil and the flotation member from contacting the wall, wherein the support member connects the foil, the follower member and the tracking member.

This invention also provides for a magnetically coupled mixing system comprising a carrier member in which the magnetic follower element is contained, wherein the carrier member is proximally disposed outside the drive conduit.

This invention also provides for a magnetically coupled mixing system comprising a bumper element disposed within the follower member.

This invention also provides for a magnetically coupled mixing system comprising a flexible elongate tension member that connects the foil or support member to the follower member.

This invention also provides for a magnetically coupled mixing system wherein the foil is uncambered, has a quadrangular planform shape and is configured at an angle of attack sufficient to generate hydrodynamic lift and trailing vortices.

This invention also provides for a magnetically coupled mixing system wherein the foil comprises a cambered surface.

This invention also provides for a magnetically coupled mixing system wherein the foil is substantially vertically oriented and has a surface configured and angled to provide hydrodynamic lift.

This invention also provides for a magnetically coupled mixing system comprising an axle attached to a support member, wherein the foil is rotatably mounted on the axle.

This invention also provides for a magnetically coupled mixing system wherein the foil further comprises a weight or a cavity embedded in the foil proximal to a trailing edge of the foil.

This invention also provides for a magnetically coupled mixing system wherein the foil further comprises a steering element disposed on the surface of the foil proximal to a trailing edge of the foil.

This invention also provides for a magnetically coupled mixing system wherein the planform shape of the foil is bilaterally symmetric and is triangular or quadrangular.

This invention also provides for a magnetically coupled mixing system comprising a support member that is substantially horizontally oriented, wherein a top edge of the support member is cambered and is adapted to induce a hydraulic jump in the liquid mixture.

This invention also provides for a magnetically coupled mixing system comprising mixing structures attached to a horizontal support member, wherein the mixing structures are configured to stir the surface of the liquid mixture.

This invention also provides for a magnetically coupled mixing system comprising a flexible dredging member attached to the foil, the pontoon or a support member, wherein the flexible dredging member is at least partially suspended in the liquid mixture and is configured to induce vertical mixing of the liquid mixture.

This invention also provides for a magnetically coupled mixing system wherein the foil is pivotally attached to a support member, such that the angle of attack of the foil is variable and selectively adjustable.

This invention also provides for a magnetically coupled mixing system comprising a poppet valve disposed inside the drive element.

This invention also provides for a magnetically coupled mixing system comprising a bypass conduit connected to the drive conduit.

This invention also provides for a magnetically coupled mixing system comprising a foil disposed only in gas.

This invention also provides for a magnetically coupled mixing system comprising a gas sparging hose attached to the follower member, the follower element, the foil or the support member.

This invention also provides for a magnetically coupled mixing system comprising a Venturi tube formed in the support member, with one opening of the Venturi tube disposed above the surface of the liquid and the opposite opening of the Venturi tube disposed below the surface of the liquid.

This invention also provides for a magnetically coupled mixing system comprising a vertically-oriented foil attached to a horizontally-oriented foil.

This invention also provides for a magnetically coupled mixing system wherein the mixing system mixes only a portion of the depth of the liquid disposed within the mixing vessel.

This invention also provides for a magnetically coupled mixing system wherein the mixing system mixes only a portion of the length of the liquid disposed within the mixing vessel.

This invention also provides for a magnetically coupled mixing system comprising a mixing vessel; a liquid disposed within the mixing vessel; a foil having a surface shaped or configured to provide hydrodynamic lift, wherein the foil is disposed at least partially in the liquid, and wherein vertical mixing of the liquid is achieved by linear motion of the foil in the mixing vessel; a cable attached to the foil; and a reversible motor adapted to pull the cable.

This invention also provides for a magnetically coupled mixing system comprising a drive conduit; a follower member having a first distal end and a second distal end, wherein the follower member is disposed around the perimeter of at least a portion of the drive conduit and is adapted to move longitudinally along the drive conduit, and wherein the cable is attached to the foil or the follower member; and a support member connecting the foil and the follower member.

This invention also provides for a system for achieving vertical mixing within a liquid in a reactor comprising a foil moving by magnetic means in a linear direction.

This invention also provides for a method to achieve vertical mixing in a liquid in a reactor comprising the steps of moving a drive element in a linear direction within the reactor; magnetically coupling a follower element to the drive element; and coupling a foil to the follower element, such that the foil produces vertical mixing in the liquid in the reactor.

This invention also provides for a system for the production of a target molecule or accumulation of biomass comprising a suspension of cells in a liquid, wherein the cells are capable of producing a target molecule or accumulating biomass; and a foil moving by magnetic means in a linear direction in the liquid and producing vertical mixing of the suspension; wherein production of the target molecule or accumulation of biomass is greater in the presence of the moving foil than in the absence of the moving foil; and wherein the system is a bioreactor.

This invention also provides for a system for the production of a target molecule or accumulation of biomass comprising a suspension of cells in a liquid, wherein the cells are capable of producing a target molecule or accumulating biomass; and a foil moving by magnetic means in a linear direction in the liquid and producing vertical mixing of the suspension; wherein accumulation of biomass is greater in the presence of the moving foil than in the absence of the moving foil; and wherein the system is a bioreactor.

This invention also provides for a system for achieving vertical mixing within a fluid in a reactor comprising a foil moving by magnetic means in a linear direction.

This invention also provides for a method to achieve vertical mixing in a fluid in a reactor comprising the steps of moving a drive element in a linear direction within the reactor; magnetically coupling a follower element to the drive element; and coupling a foil to the follower element, such that the foil produces vertical mixing in the fluid in the reactor.

This invention also provides for a magnetically coupled mixing system comprising a mixing vessel; a fluid disposed within the mixing vessel; a drive conduit; a drive element disposed within the drive conduit and adapted to move in a longitudinal direction within the drive conduit; a follower member having a first distal end and a second distal end, wherein the follower member is disposed around the perimeter of at least a portion of the drive conduit and is adapted to move longitudinally along the drive conduit; a magnetic follower element disposed within the follower member, wherein the magnetic follower element is adapted to couple magnetically with the drive element and is proximally disposed outside the drive conduit; a foil having a surface shaped or configured to provide lift, wherein the foil is disposed at least partially in the fluid, and wherein vertical mixing of the fluid is achieved by linear motion of the foil in the mixing vessel; and a support member connecting the foil and the follower member.

This invention also provides for a magnetically coupled mixing system comprising a mixing vessel; a fluid disposed within the mixing vessel; a foil having a surface shaped or configured to provide lift, wherein the foil is disposed at least partially in the fluid, and wherein vertical mixing of the fluid is achieved by linear motion of the foil in the mixing vessel; a cable attached to the foil; and a reversible motor adapted to pull the cable.

This invention also provides for a magnetically coupled mixing system comprising a mixing vessel; a liquid disposed within the mixing vessel; a drive conduit; a drive element disposed within the drive conduit and adapted to move in a longitudinal direction within the drive conduit; and a magnetic follower element disposed around the perimeter of at least a portion of the drive conduit and adapted to move longitudinally along the drive conduit, wherein the magnetic follower element is adapted to couple magnetically with the drive element and is proximally disposed outside the drive conduit.

This invention also provides for a system for the production of a target molecule or accumulation of biomass comprising a suspension of cells in a liquid, wherein the cells are capable of producing a target molecule or accumulating biomass; and a foil moving by magnetic means in a linear direction in the liquid and producing vertical mixing of the suspension;

wherein the total cost of mixing per unit weight of the target molecule or biomass produced is lower using the foil to induce vertical mixing than using a paddlewheel mixer.

BRIEF DESCRIPTION OF DRAWINGS

These and other features, aspects and advantages of this invention will become better understood with regard to the following description, appended claims and accompanying drawings where:

FIG. 8 shows a sectional view of a drive element in accordance with certain embodiments of the present invention;

FIG. 9 shows a perspective view of a drive element in accordance with certain embodiments of the present invention;

FIGS. 33A and B show foils, flotation members, a drive system and support members in accordance with certain embodiments of the present invention;

FIGS. 34A-D show foils in accordance with certain embodiments of the present invention;

FIGS. 35A-D show flotation members, support members, foils, flexible dredging members and brushes in accordance with certain embodiments of the present invention;

FIG. 36 shows a foil, flotation member and support members that are rotatably connected in accordance with certain embodiments of the present invention;

FIG. 45 shows a perspective view of tethered chive elements in accordance with certain embodiments of the present invention;

FIG. 46 shows a side view of an embodiment of the present invention adapted to produce a breaking wave in shallow liquid;

FIG. 47 shows a side view of an embodiment of the present invention producing a breaking wave in shallow liquid; and FIG. 48 shows a perspective view of an embodiment of the present invention producing a breaking wave in shallow liquid.

DETAILED DESCRIPTION OF EMBODIMENTS

Mixer Drive System Design

FIGS. 1-4 show sectional, perspective and front views of a tubular follower member 120. In the exemplary embodiment, the tubular follower member 120 is disposed around a portion of a drive conduit 100, such that the follower member 120 slides along the surface of the drive conduit 100 in a longitudinal direction. The follower member 120 partially encloses a magnetic follower element 110, which is adapted to slide within the follower member 120 along the surface of the drive conduit 100 in a longitudinal direction. The distal end portions 192 of the follower member 120 are partially enclosed, thereby restricting the movement of the follower element 110 and providing surfaces against which the follower element 110 can exert force.

The follower member 120 and drive conduit 100 can be constructed from, for example, blow-molded or injection-molded thermoplastic, or any other material that is suitably rigid and light-weight.

Figure 1:
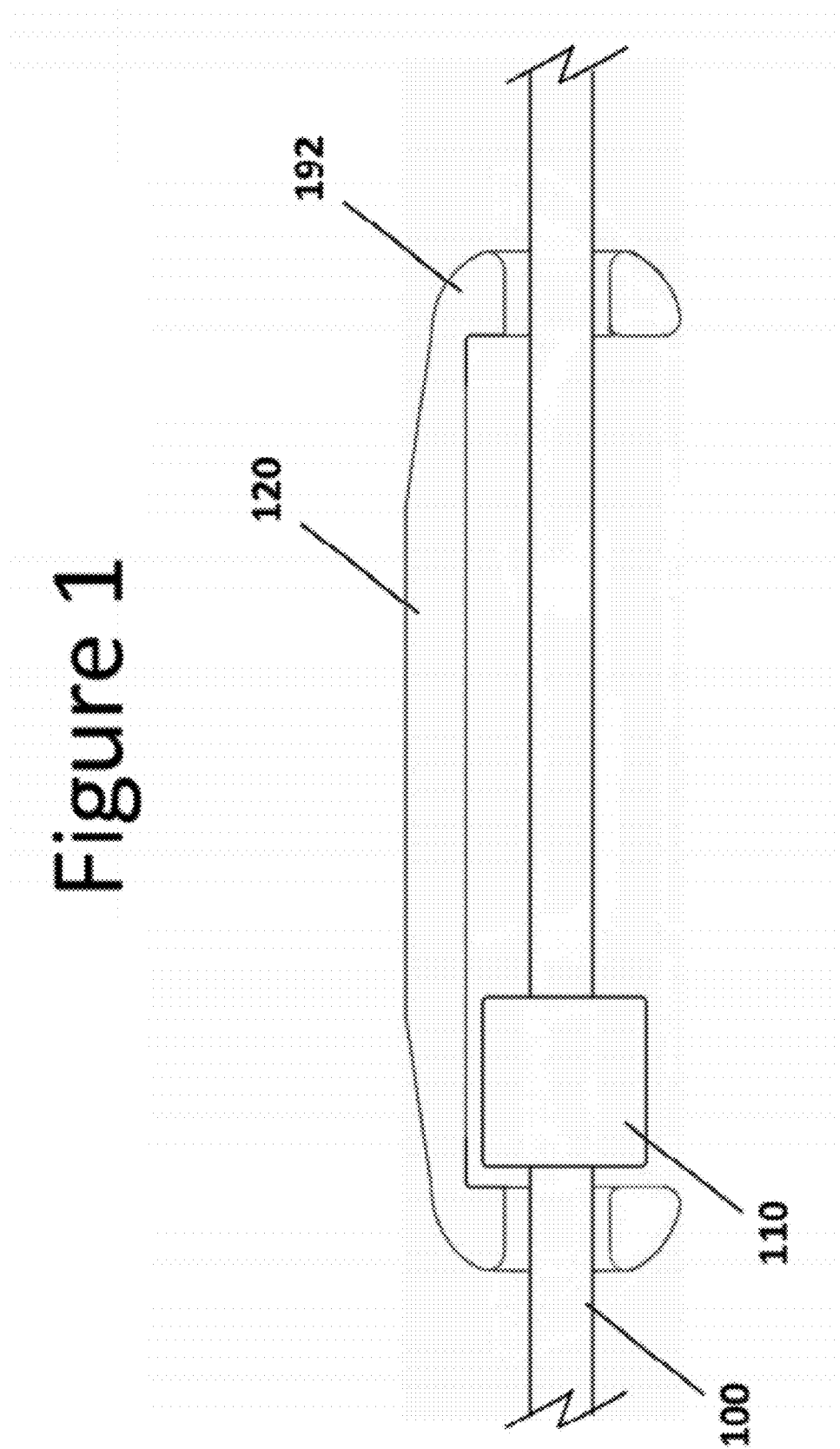
FIG. 1 shows a sectional view of a portion of a mixing system in accordance with certain embodiments of the present invention.
Figure 2:
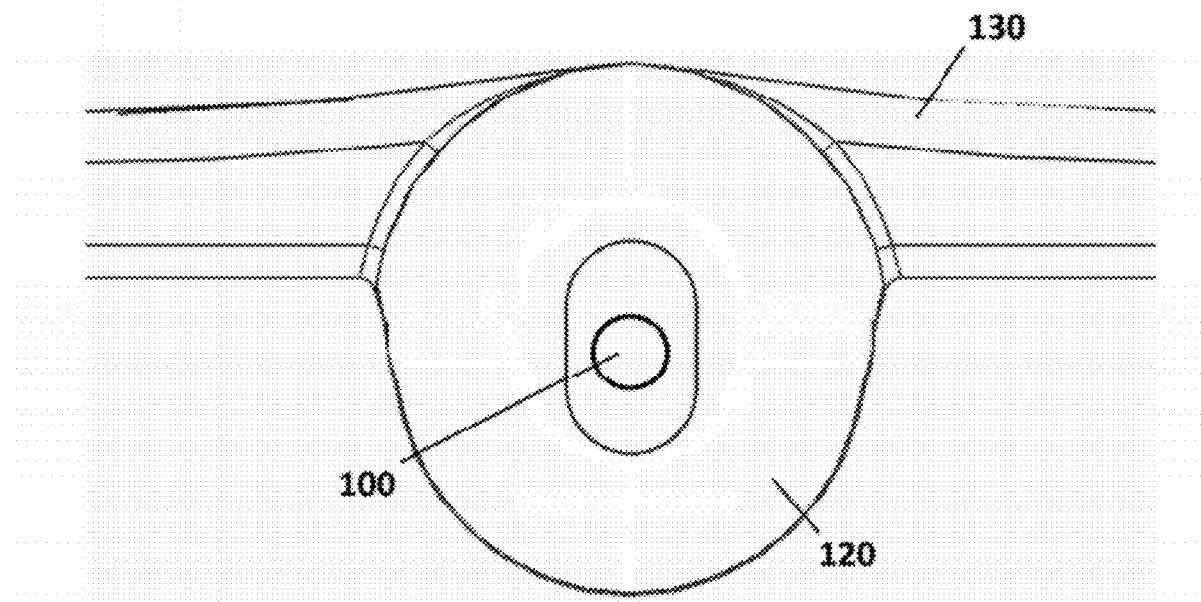
FIG. 2 shows an axial view of a portion of a mixing system in accordance with certain embodiments of the present invention.
Figure 3:
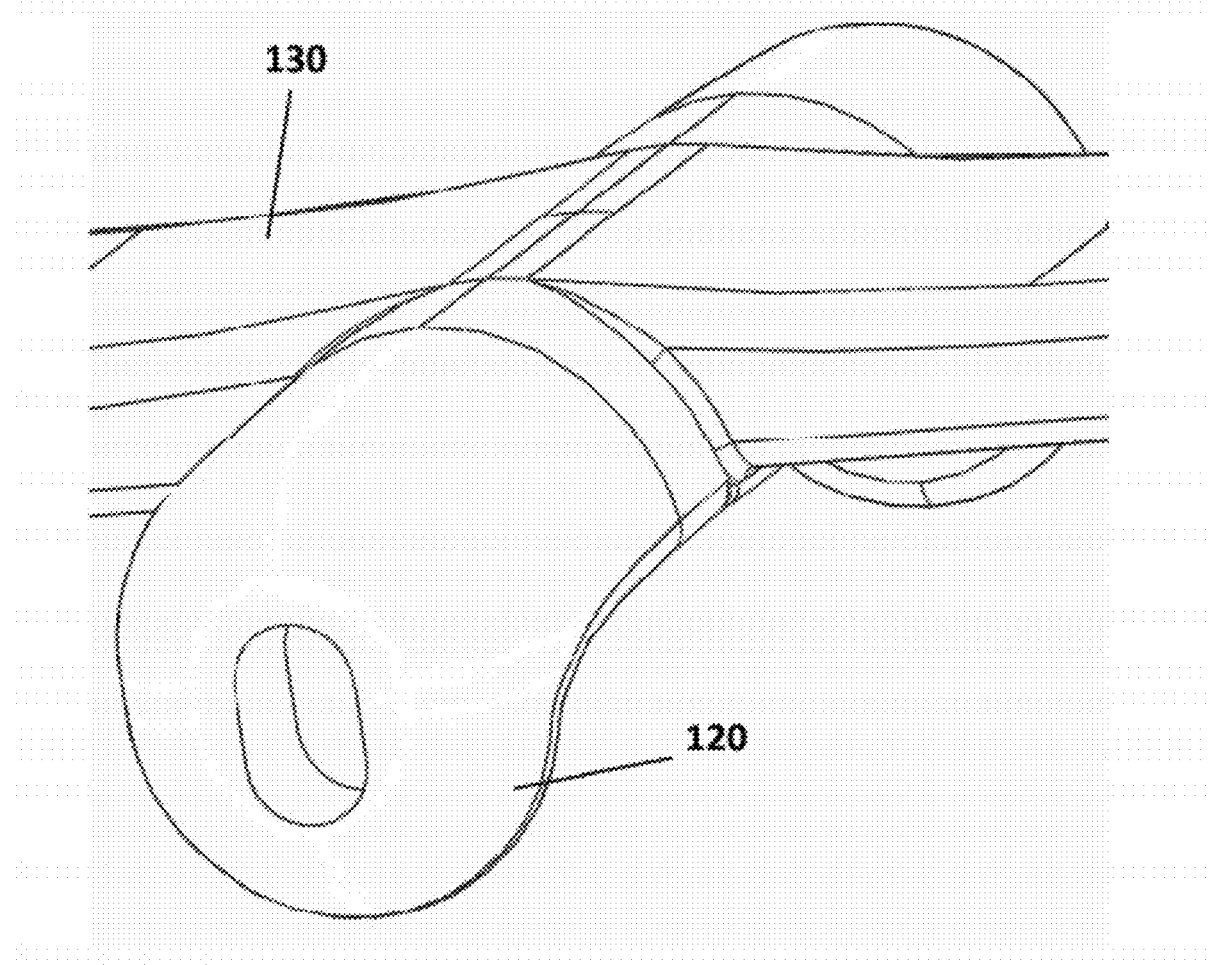
FIG. 3 shows a perspective view of a portion of a mixing system in accordance with certain embodiments of the present invention.
Figure 4:
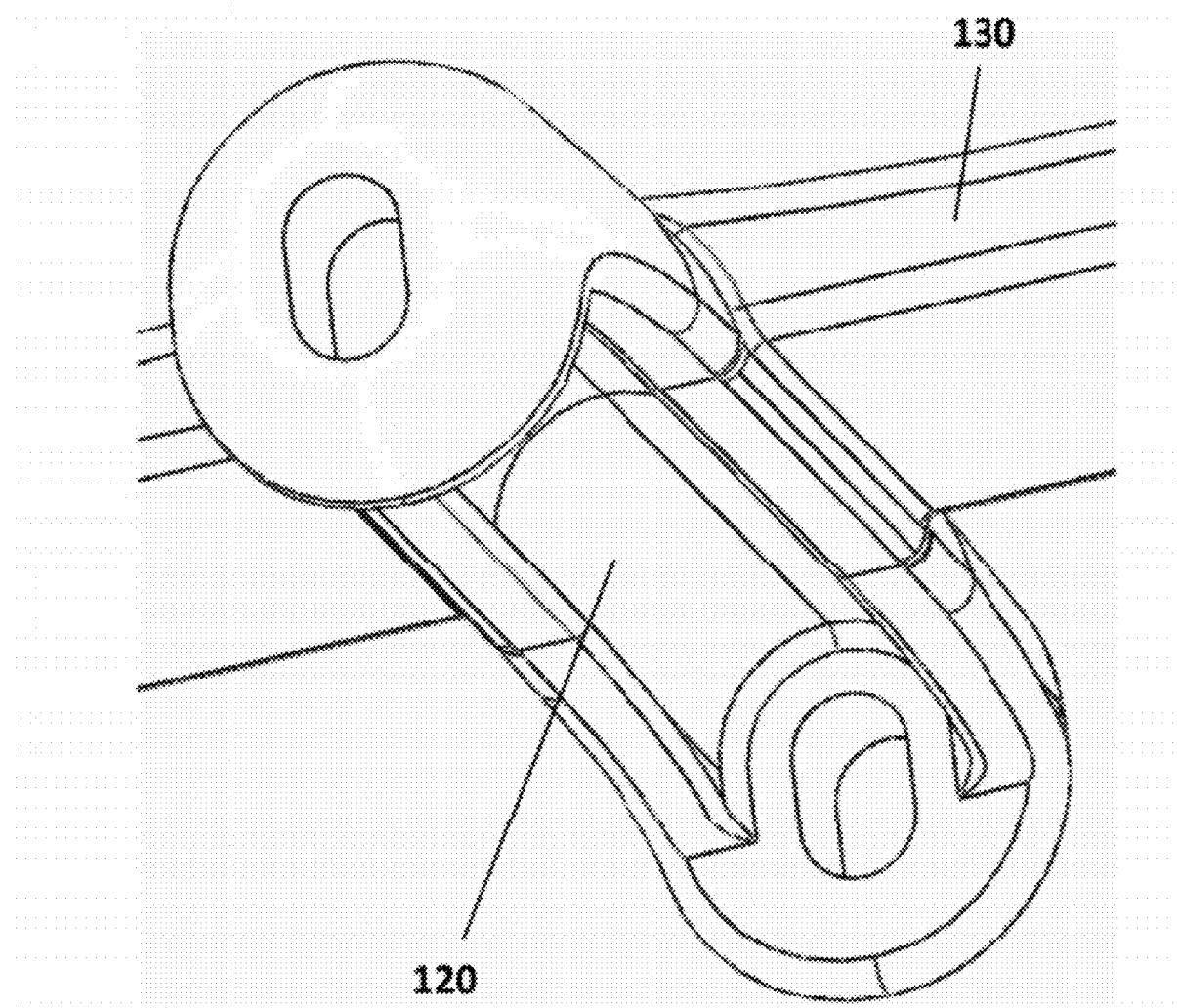
FIG. 4 shows a perspective view of a portion of a mixing system in accordance with certain embodiments of the present invention.
Figure 5A:
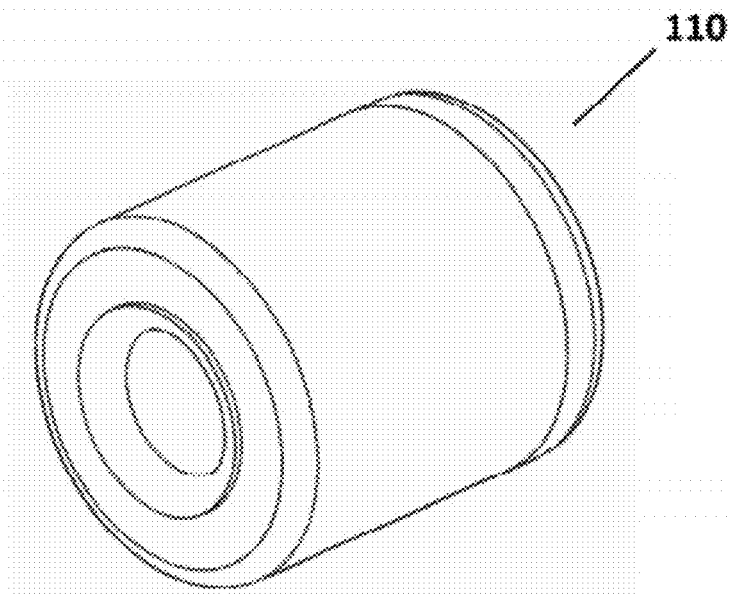
FIGS. 5A and B show a perspective and sectional view, respectively, of a follower element in accordance with certain embodiments of the present invention.
Figure 5B:
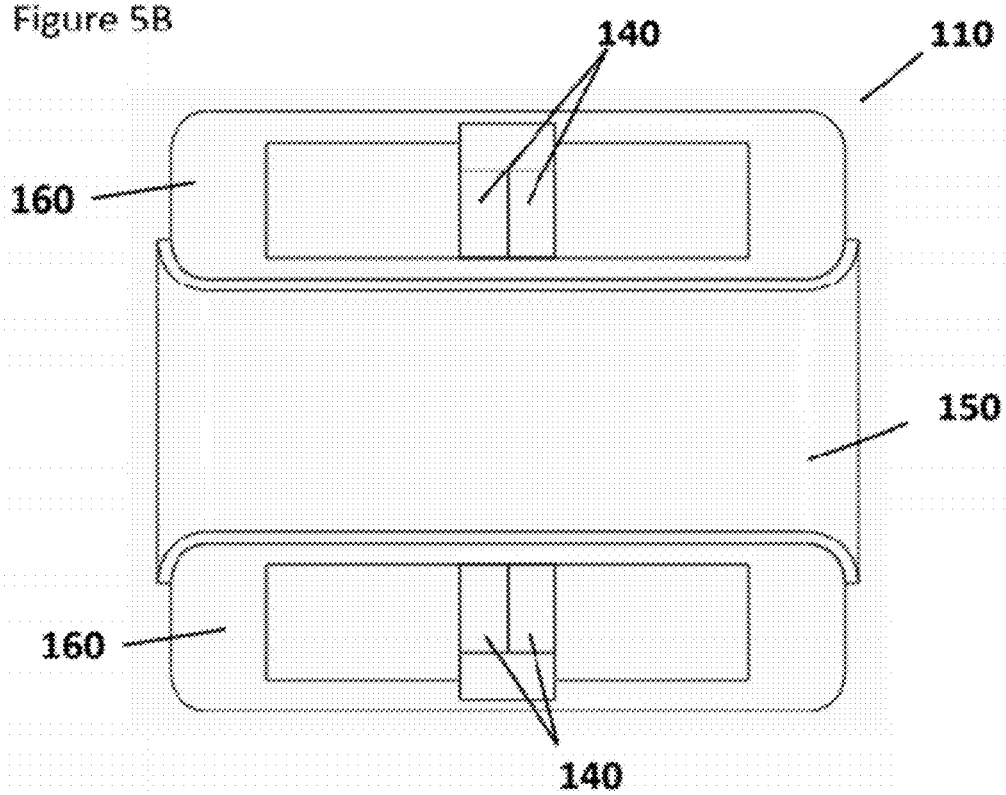

FIGS. 5A and B show perspective and sectional views of an exemplary follower element 110, comprising magnets 140, a bushing 150 and an enclosure 160. The annular axial cross-section of the bushing 150 enables the follower element 110 to slide axially along the drive conduit 100.

The bushing 150 can be constructed from, for example, stainless steel or any other material that is suitably resistant to wear and has a low coefficient of friction. The enclosure 160 can be constructed from, for example, polyethylene or any other material that is suitably durable and has a low coefficient of friction.

Figure 6:
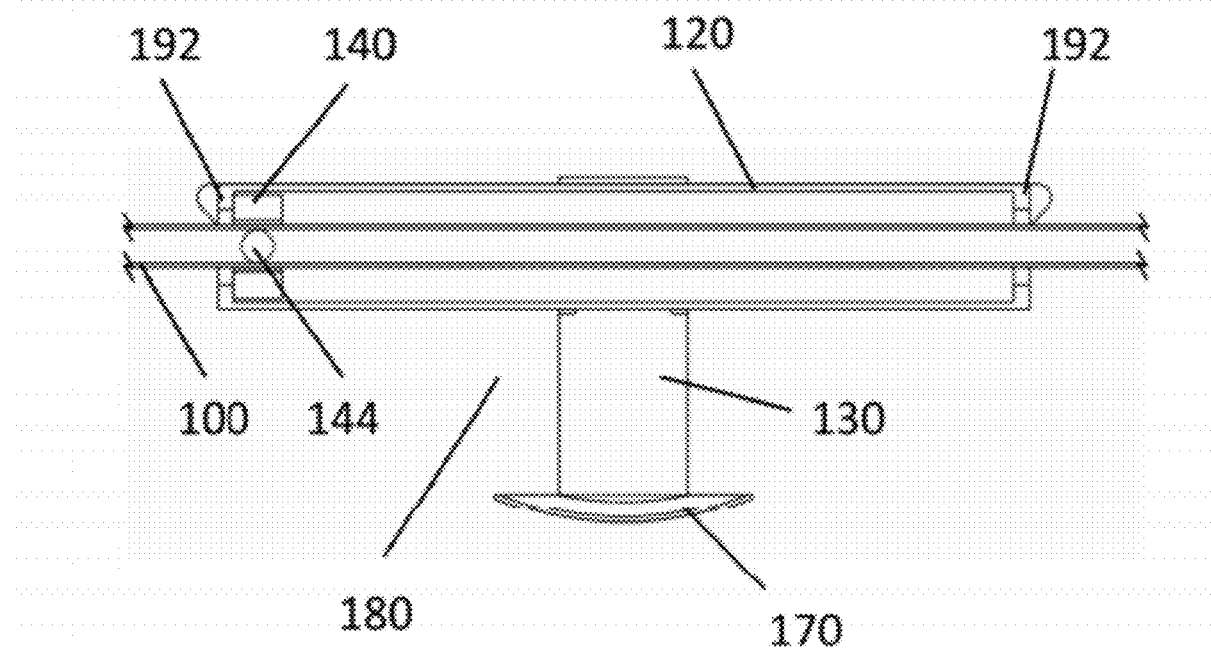
FIG. 6 shows a sectional view of a portion of a mixing system in accordance with certain embodiments of the present invention.
Figure 7A:
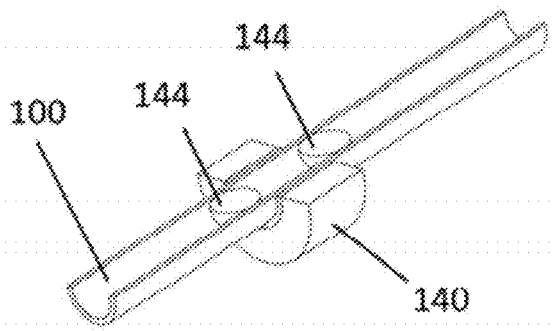
FIGS. 7A-H show sectional views of exemplary suitable configurations of drive elements and follower elements.
Figure 7B:
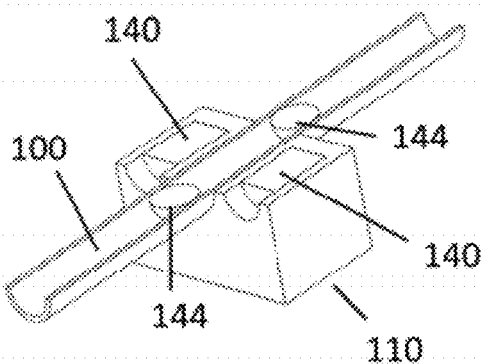
Figure 7C:
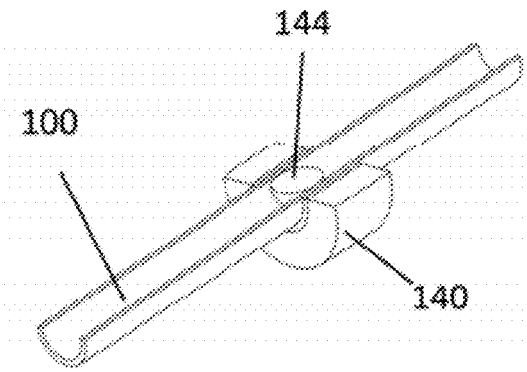
Figure 7D:
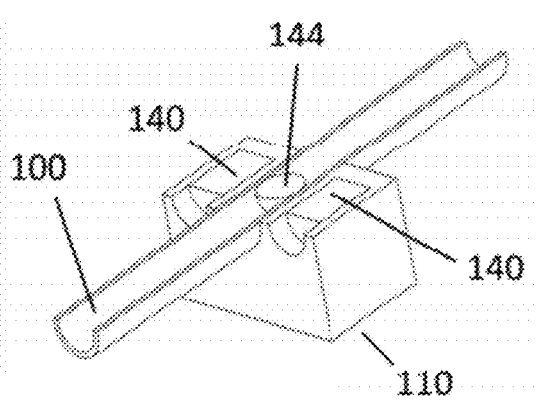
Figure 7E:
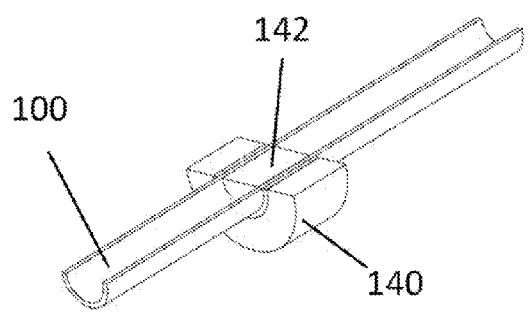
Figure 7F:
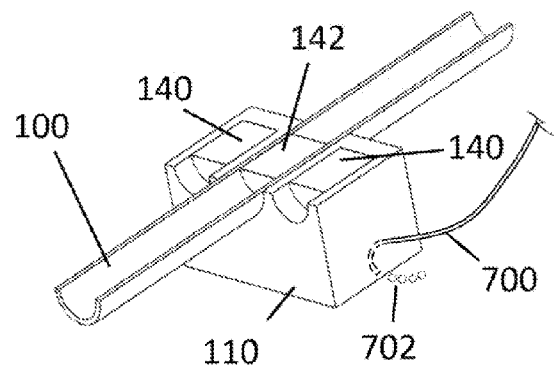
Figure 7G:
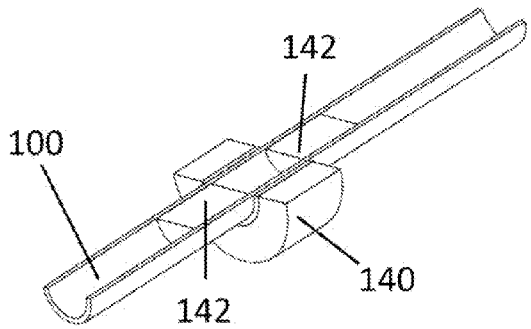
Figure 7H:
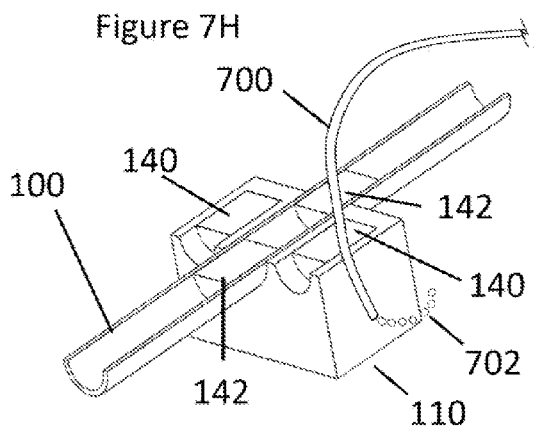

FIG. 6 illustrates a sectional view of a portion of an exemplary foil assembly 180 of the present invention. In certain embodiments, the drive system utilizes magnetic coupling between a drive magnet 142 or drive ferromagnet 144 contained within the drive conduit 100 and a follower magnet 140 disposed outside the drive conduit 100, within the follower member 120, wherein the magnetic coupling is used in conjunction with a motive force, such as a pneumatic force or a hydraulic force, to propel the foil assembly 180 through a mixing vessel.

In the exemplary embodiment, a tubular follower member 120 is disposed around a portion of a drive conduit 100, such that the follower member 120 slides along the surface of the drive conduit 100 in a longitudinal direction. The follower member 120 is connected to a hydrodynamic cambered foil 170 by a support member 130. The distal end portions 192 of the follower member 120 are partially enclosed.

In the exemplary embodiment, the follower magnet 140 is a ring magnet that encompasses the circumference of the exterior surface of the drive conduit 100. The follower magnet 140 is adapted to slide within the follower member 120 along the surface of the drive conduit 100 in a longitudinal direction. The partial enclosures of the end portions 192 of the follower member 120 restrict the movement of the follower magnet 140 relative to the follower member 120 and provide surfaces against which the follower magnet 140 can exert force.

The drive magnet 142 or drive ferromagnet 144 is disposed within the drive conduit 100 and is adapted to move longitudinally within the drive conduit 100 when motive force is applied to the drive magnet 142 or drive ferromagnet 144.

In operation, a motive force is applied to the drive magnet 142 or drive ferromagnet 144, which traverses the drive conduit 100 in a longitudinal direction. The follower magnet 140 is magnetically coupled with the drive magnet 142 or drive ferromagnet 144 and moves in unison with the drive magnet 142 or drive ferromagnet 144. When the follower magnet 140 comes into contact with the partial enclosure of either end portion 192 of the follower member 120, the momentum of the follower magnet 140 is transferred to the follower member 120, which is propelled by the follower magnet 140 and slides along the length of the drive conduit 100. The foil 170 is connected to, and moves with, the follower member 120, such that the foil 170 traverses through the mixing vessel and the liquid mixture contained therein in a linear path.

The direction in which motive force is applied to the drive magnet 142 or drive ferromagnet 144 can be reversed, inducing the drive magnet 142 or drive ferromagnet 144 to move in the opposite longitudinal direction. The follower magnet 140 is magnetically coupled with the drive magnet 142 or drive ferromagnet 144 and correspondingly changes direction of motion with the drive magnet 142 or drive ferromagnet 144. Immediately after the initial change of direction of motion, the follower magnet 140 disengages from contact with the partial enclosure of the end portion 192 of the follower member 120 and traverses the open interior portion of the follower member 120, during which the follower member 120 will remain stationary, or will not otherwise undergo motion attributable to the follower magnet 140. If movement of the follower magnet 140 is sustained, the follower magnet 140 subsequently comes into contact with the opposite partially enclosed end portion 192 of the follower member 120 and transfers momentum to the follower member 120. The follower member 120 and attached foil 170 consequently undergo a change of direction of motion.

In the exemplary embodiment, the distance between the position of the partially enclosed end portion 192 of the follower member 120 and the vertical centerline of the support member 130 creates a locus of force, or tow point, between the follower magnet 140 and follower member 120 that is forward of the foil 170 relative to the direction of motion of the foil assembly 180. When the direction of motion reverses, the tow point becomes the point of contact between the follower magnet 140 and the opposite end of the follower member 120, which is likewise forward of the foil 170 relative to the direction of motion of the foil assembly 180. This configuration enhances guidance and stability of the follower member 120 and the attached foil 170 by preventing yaw of the foil assembly 180 while the follower member 120 is in motion in either direction.

FIGS. 7A-H illustrate exemplary suitable drive magnets 142 or drive ferromagnets 144 and follower magnets 140. Each drive magnet 142 or drive ferromagnet 144 is disposed within a drive conduit 100 and is adapted to move within the drive conduit 100 in a longitudinal direction in response to a motive force applied to the drive magnet 142 or drive ferromagnet 144. The drive magnets 142 or drive ferromagnets 144 comprise, for example, one or more ferromagnetic ball bearings, one or more axially-magnetized cylindrical magnets, or one or more spherical magnets. One, of skill in the art will understand that the drive magnet 142 or drive ferromagnet 144 can be made of any material and have any shape suitable to promote magnetic coupling with the follower magnet 140 and range of motion within the drive conduit 100. In some embodiments, the drive magnet 142 or drive ferromagnet 144 comprises steel, a neodymium iron boron magnet or another rare earth magnet. In some embodiments, the drive magnet 142 or drive ferromagnet 144 is coated with felt or other materials that are suitable for suppressing corrosion or wear of the drive magnet 142 or drive ferromagnet 144 and other surfaces that come into contact with the drive magnet 142 or drive ferromagnet 144.

In certain embodiments, the drive conduit 100 is a tube having a circular cross section and is made of low density polyethylene, high density polyethylene, cross-linked polyethylene, polyvinyl chloride, copper, steel or any other suitable material. In some embodiments, the construction of the drive conduit 100 provides positive buoyancy to help maintain the position of the drive conduit 100 relative to the surface 320 of the liquid mixture.

The follower magnet 140 is disposed on or around the external surface of the drive conduit 100 in a manner that allows the follower magnet to move along the longitudinal axis of the drive conduit 100. An example of a suitable follower magnet 140 is one axially-magnetized ring magnet, wherein the ring magnet circumferentially encompasses a portion of the drive conduit 100. Another suitable configuration is a plurality of follower magnets 140 embedded in a follower element 110 in the form of a sliding sleeve. In some embodiments, the follower member 120 does not fully encircle the drive conduit 100. In some embodiments, the follower magnets 140 are disposed on opposite sides of the drive conduit 100 and are equidistant apart relative to the circumference of the drive conduit 100. One of skill in the art will understand that the follower magnet 140 may be made of any material and have any shape suitable to promote magnetic coupling with the drive magnet 142 or drive ferromagnet 144 and longitudinal range of motion along the exterior of the drive conduit 100. In some embodiments, the follower magnet 140 comprises a neodymium iron boron magnet or another rare earth magnet.

In the present invention, the gap between the surface of the drive magnet 142 or drive ferromagnet 144 and the interior surface of the drive conduit 100 is minimized in order to reduce hydraulic or pneumatic fluid flow around the drive magnet 142 or drive ferromagnet 144 and maximize motive force applied to the drive magnet 142 or drive ferromagnet 144 and the foil 170 for a selected flow rate of drive fluid. In certain embodiments comprising a pneumatic fluid used to apply motive force to the drive magnet 142 or drive ferromagnet 144, a low friction seal between the surface of the drive magnet 142 or drive ferromagnet 144 and the interior surface of the drive conduit 100 is utilized. The low friction seal can be created by, for example, dispersing oil along the length of the interior surface of the drive conduit 100 or by applying a ferromagnetic fluid to the surface of the drive magnet 142 or drive ferromagnet 144. In certain embodiments, felt or another suitable material or coating is adhered or applied to the surface of the drive magnet 142 or drive ferromagnet 144 to reduce friction between the drive magnet 142 or drive ferromagnet 144 and the inner surface of the drive conduit 100.

FIG. 8 shows a sectional view of a drive element 190 disposed within a drive conduit 100. The drive element comprises a drive magnet 142 or drive ferromagnet 144 embedded in a plug of closed cell foam 200, wherein the shape of the plug of closed cell foam 200 conforms to the inner surface of the drive conduit 100. The drive element 190 further comprises inserts of open cell foam 210 embedded within the plug of closed cell foam 200. The inserts of open cell foam 210 are positioned and adapted to expand and exert outward pressure on the plug of closed cell foam 200 in order to improve sealing and decrease empty space between the outer surface of the drive element 190 and the inner surface of the drive conduit 100.

Figure 10A:
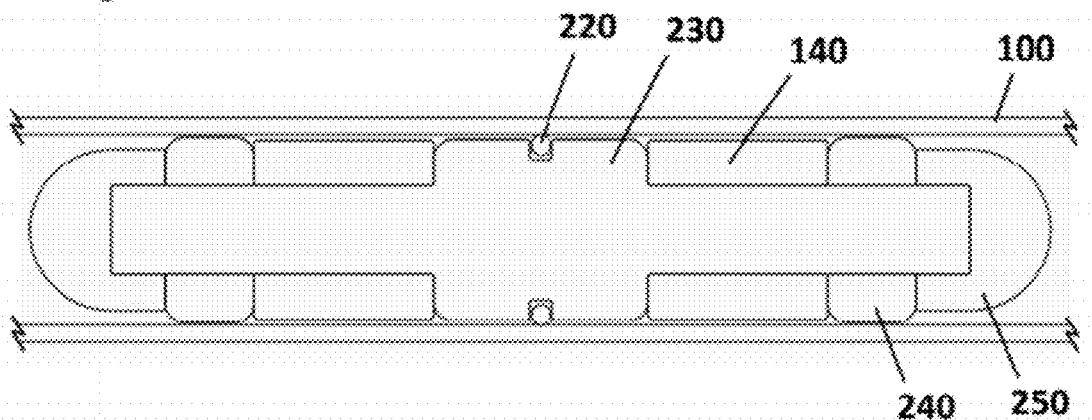
FIGS. 10A-C show sectional views of a drive element in accordance with certain embodiments of the present invention.
Figure 10B:
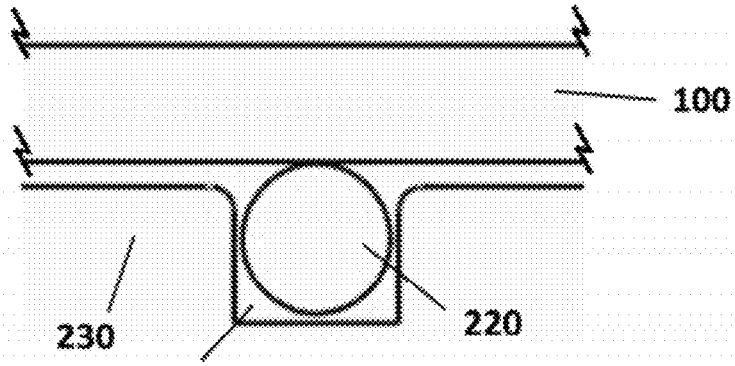
Figure 10C:
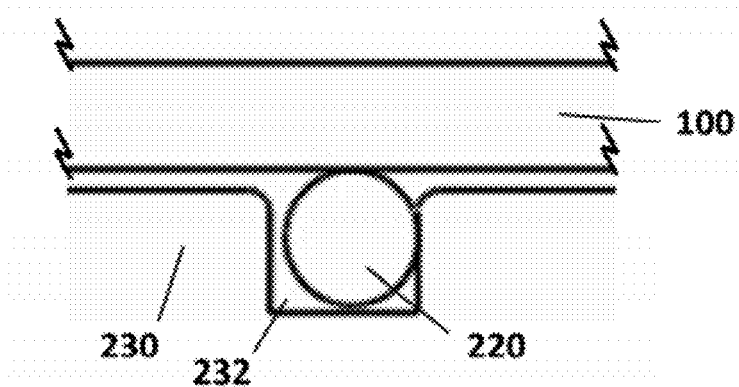

FIGS. 9 and 10A-C show another embodiment of a drive element 190, comprising a drive magnet 142 or drive ferromagnet 144, an o-ring 220, an insert 230, a ring 240 and an end cap 250. The o-ring 220 may be made of, for example, nitrile rubber. The insert 230 may be made of, for example, nylon 6-6. The ring 240 may be made of, for example, polytetrafluoroethylene. The end cap 250 may be made of, for example, nylon 6-6. The outside diameter of the o-ring 220 is slightly larger than the inside diameter of the drive conduit 100. The o-ring gland 232 in the insert 230 in which the o-ring 220 sits is wider than the diameter of the o-ring 220, and the inside diameter of the o-ring 220 is slightly larger than the diameter of the o-ring gland 232 in which the o-ring 220 sits, such that the o-ring 220 sits loosely in the o-ring gland 232. When the drive element 190 is disposed in the drive conduit 100, the o-ring 220 is squeezed against the inside wall of the drive conduit 100 but is free to move laterally in the o-ring gland 232 (FIG. 10B). Pneumatic motive force applied to the drive element 190 forces the o-ring 220 to move in the direction of the motive force until it contacts the wall of the o-ring gland 232, forming a floating seal between the o-ring 220, the wall of the o-ring gland 232 and the inner wall of the drive conduit 100 (FIG. 10C).

Figure 11A:
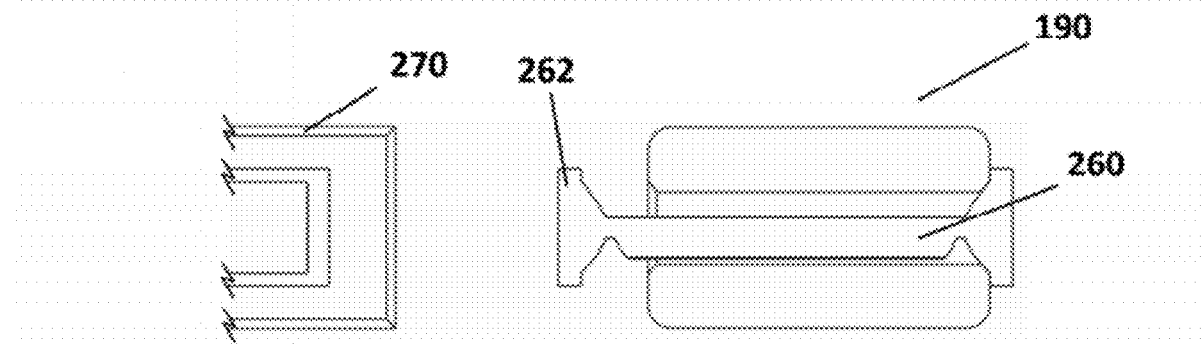
FIGS. 11A-C show sectional and perspective views of a drive element in accordance with certain embodiments of the present invention.
Figure 11B:
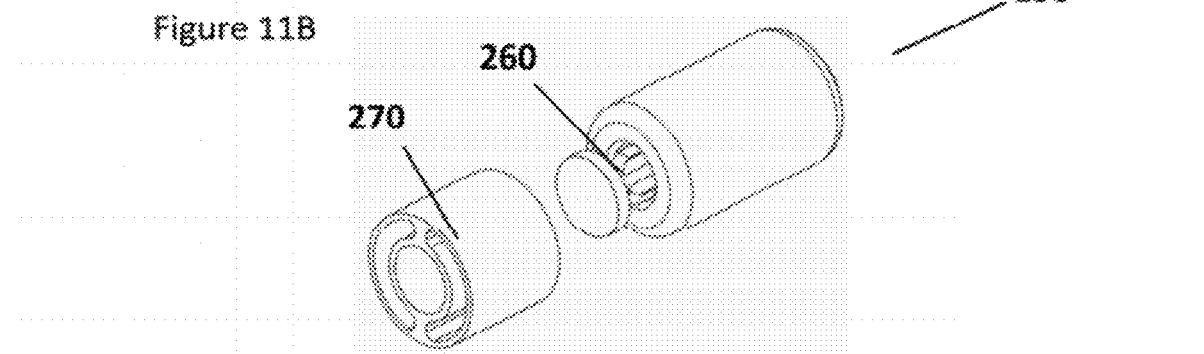
Figure 11C:
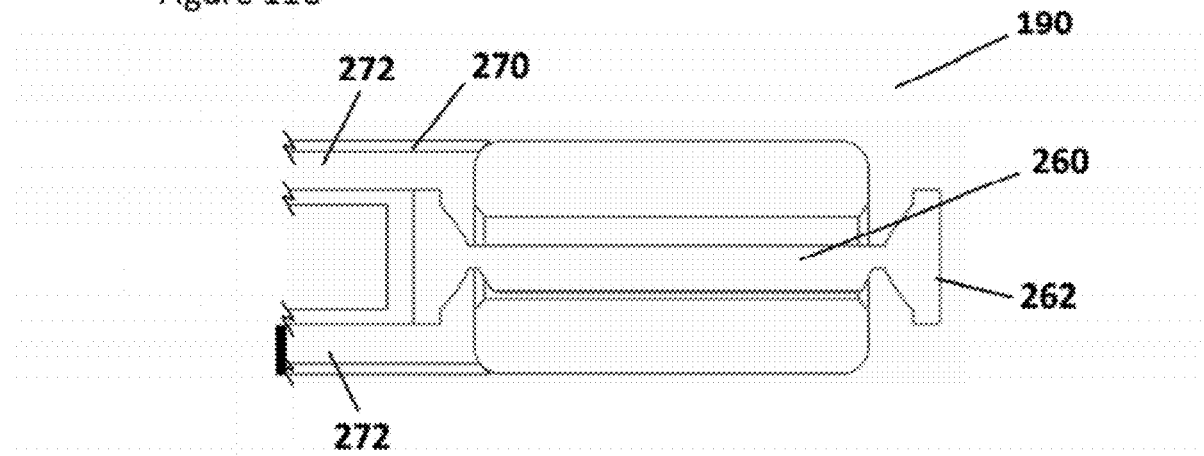
Figure 12A:
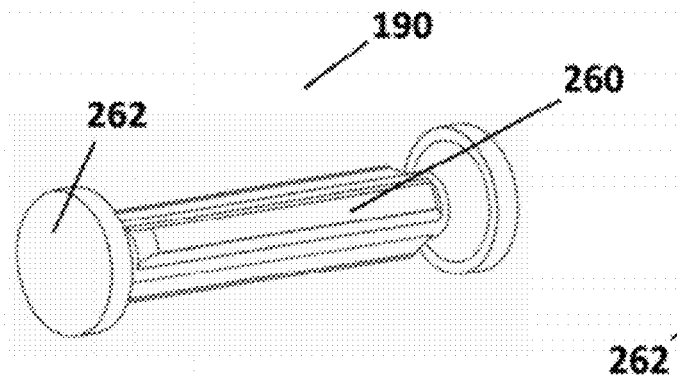
FIGS. 12A-D show sectional and perspective views of a drive element in accordance with certain embodiments of the present invention.
Figure 12B:
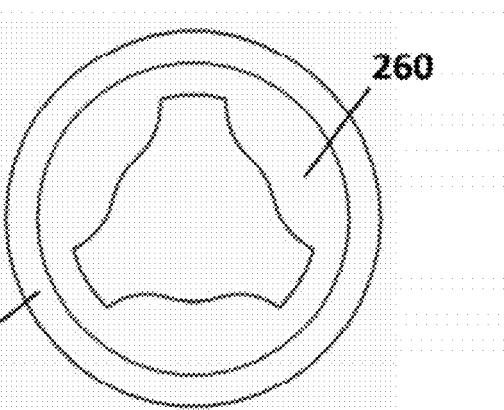
Figure 12C:
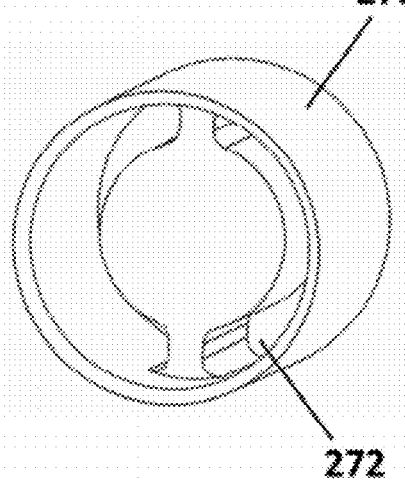
Figure 12D:
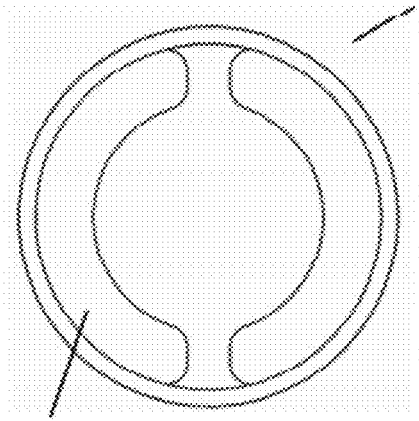

FIGS. 11A-C and 12A-D show a drive element 190 that incorporates a bypass adapted for use with a mixing system that incorporates a hydraulic form of motive force. The drive element 190 has an annular shape, and a plunger 260 is disposed at least partially within the drive element 190 such that the plunger 260 can slide laterally within the drive element 190. When the plunger 260 is positioned such that neither head 262 is in contact with the drive element 190, fluid can flow around the plunger 260 and through the annular opening in the drive element 190 (FIG. 11C).

A cap 270 may be sized and positioned within the drive conduit 100 such that the cap 270 restricts the lateral motion of the drive element 190. The cap 270 may be configured so as to hold the plunger 260 in the open position when the cap contacts the drive element 190, such that fluid flows through the annular opening in the drive element 190 and through corresponding channels 272 formed in the cap 270. If any blockage occurs in the drive system, the configuration shown in FIGS. 11A-C and 12A-D prevents excess fluid pressure from accumulating.

Figure 13:
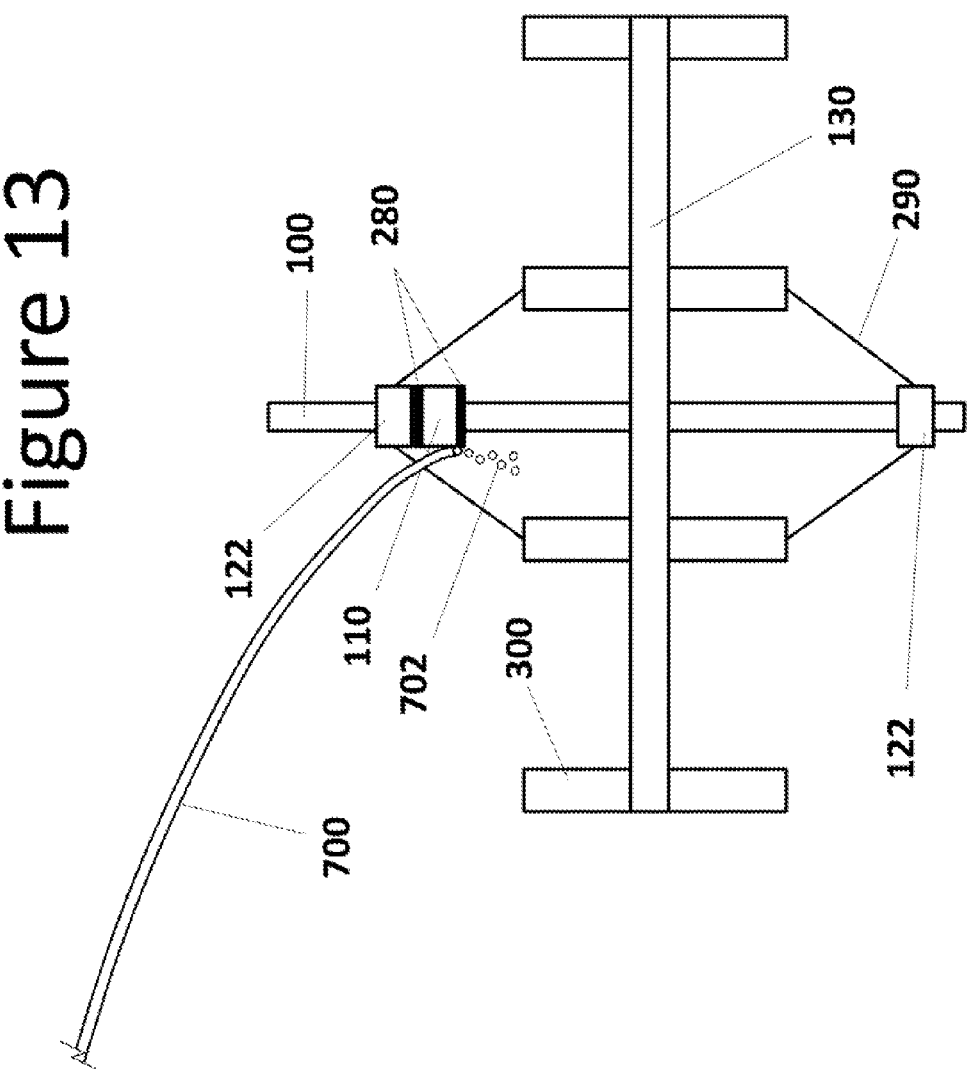
FIG. 13 shows a portion of a mixing system in accordance with certain embodiments of the present invention.

As illustrated in FIG. 13, the towing point for rigidly mounted foils 170 is shifted forward of the flotation members 300, which act as rudders to provide steering, when the direction of movement of the foil assembly 180 is reversed. The exemplary embodiment illustrated in FIG. 13 allows the tow point of the foil assembly 180 to slide to a stop beyond the flotation members 300 by allowing the follower element 110 to slide along the drive conduit 100 between end caps 122 that are mounted in fixed positions on the drive conduit 100. Pads 280 may be attached to the follower element 110 or end caps 122 to reduce the force of impact caused by acceleration of the foil assembly 180 during a reversal in the direction of motion. The impact force may also be reduced by incorporating an alternative attachment between the foil 170, flotation member 300 or support members 130 and the end caps 122. The attachment may incorporate flexible tension members 290 made of for example, 0.125 inch-diameter silicon rubber, under slight tension. The tow point in this exemplary embodiment also alternates as a steering element or stabilizing rudder when it is shifted aft of the foil 170.

Figure 14:
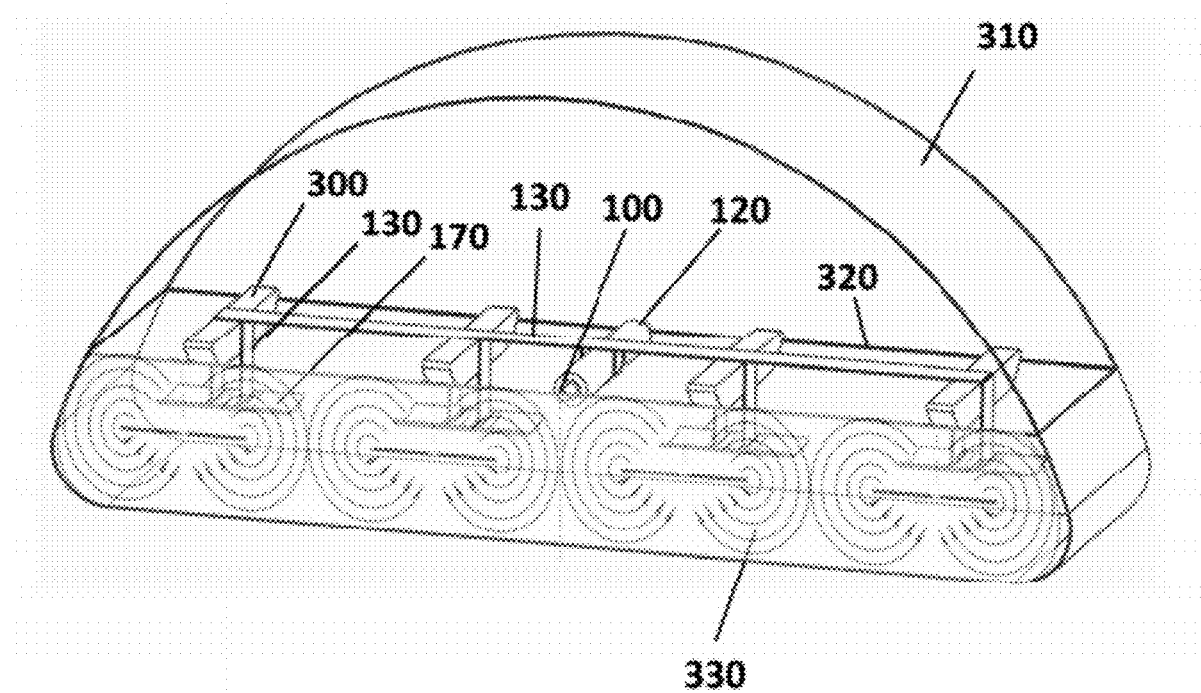
FIG. 14 shows a sectional perspective view of a mixing system and idealized fluid flow in accordance with certain embodiments of the present invention.
Figure 15:
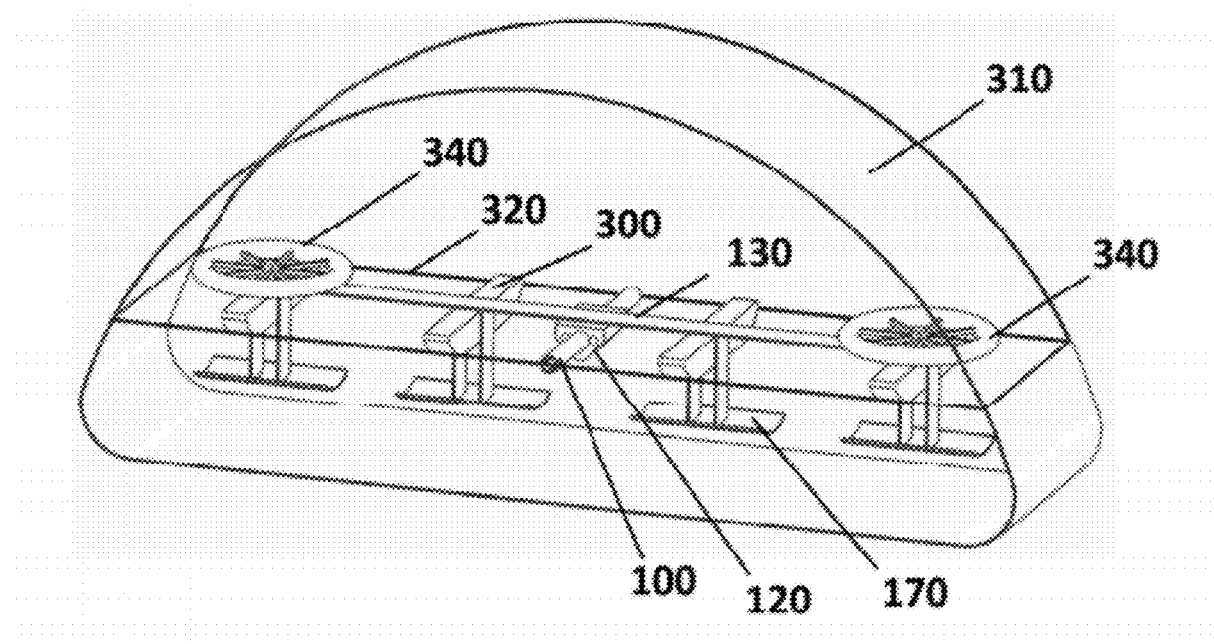
FIG. 15 shows a sectional perspective view of a mixing system in accordance with certain embodiments of the present invention.

FIGS. 14, 15, 16 and 17A-C illustrate alternative embodiments of mixing vessels containing liquid algae cultures and mixing systems in accordance with the present invention. In FIGS. 14 and 15, the drive conduit 100 is disposed in or above the surface 320 of the algae culture so that it floats in the photobioreactor 310. The drive conduit 100 may be made from, for example, high density polyethylene or any other suitable material that is inexpensive and is durable in saltwater, volatile compounds, sterilizing agents and moderate heat. In the exemplary embodiments, the follower element 120 contains follower magnets 140. Magnets of 0.5 inch diameter and 0.5 inch length can achieve a coupling force of four pounds with minimal lateral force acting on the drive magnet 142 or drive ferromagnet 144, which would be exhibited as friction between the drive magnet 142 or drive ferromagnet 144 and the inner wall surface of the drive conduit 100. The exemplary embodiments also incorporate horizontal support members 130 positioned above the surface 320 of the algae culture to reduce hydrodynamic drag, and vertical support members 130 connecting the flotation members 300 to the foils 170 that are adapted to minimize interference with fluid flow around the foils 170.

Figure 16:
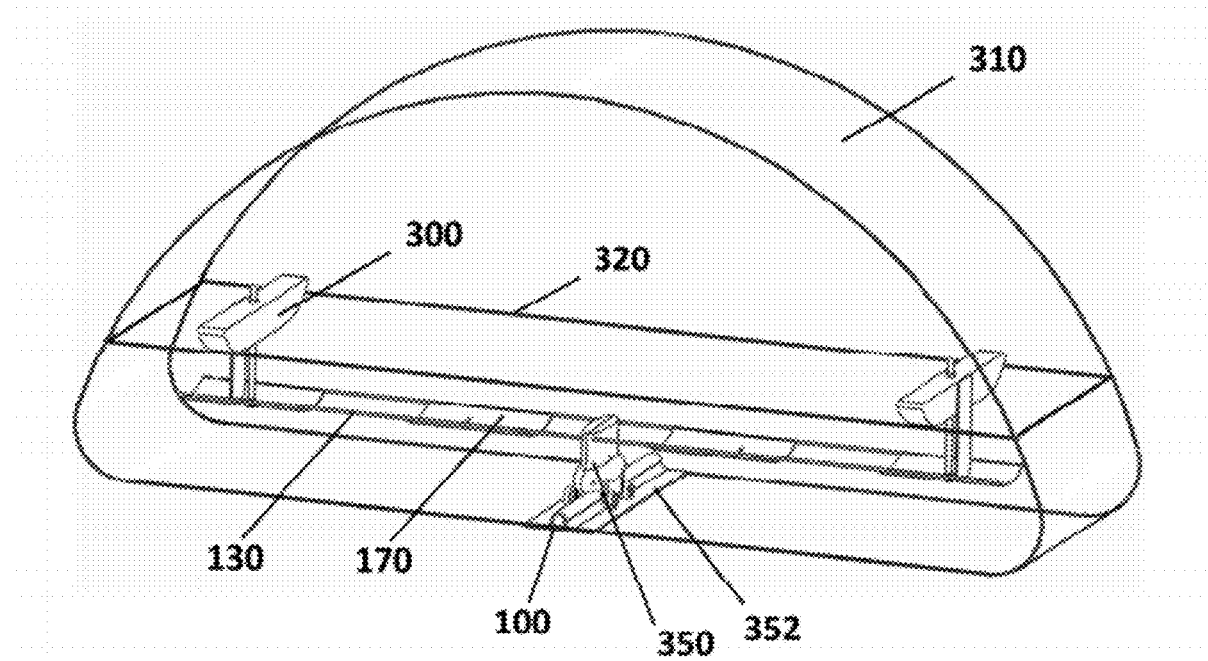
FIG. 16 shows a sectional perspective view of a mixing system in accordance with certain embodiments of the present invention.

In some embodiments, the drive conduit 100 is located outside the mixing vessel, and the drive element 190 contained therein is magnetically coupled to a foil assembly 180 disposed inside the mixing vessel. As shown in FIG. 16, the drive conduit 100 is disposed underneath the bottom surface of the photobioreactor 310. The film of the photobioreactor 310 lays over the drive conduit 100 and a track 352. The weight of the algae culture provides sufficient hydraulic pressure to fix the position of the drive conduit 100 and the track 352. A wheeled carrier 350 inside the photobioreactor 310 longitudinally traverses the track 352 and carries a follower magnet 140 that is magnetically coupled with a drive magnet 142 or drive ferromagnet 144 disposed within the drive conduit 100. An array of foils 170 are attached to the wheeled carrier 350. In some embodiments, the drive conduit 100 and the track 352 are welded or otherwise fixed to the film of the bioreactor 310.

Sufficient vertical and horizontal clearances between the wheeled carrier 350 and the track 352 are maintained to accommodate for the conformation of the film around the track 352. In the exemplary embodiment, a set of 3, 0.5 inch long follower magnets 140 provides 2 pounds of coupling force in the axial direction, which is sufficient to maintain coupling during sudden decelerations of the drive element 190 when stopped or started at the ends of the photobioreactor 310. This arrangement of follower magnets 140 also provides a torque and downward attraction force of approximately 4 pounds that prevents the wheeled carrier 350 from separating from the track 352.

The embodiments illustrated in FIGS. 14 and 15 eliminate the need to lay the film of the photobioreactor 310 carefully over the drive conduit 100 in the embodiment of FIG. 16 in order to avoid wrinkles that might structurally compromise the film of the photobioreactor 310 and the need to have a flat track 352 underneath the photobioreactor 310. In the embodiments of FIGS. 14 and 15, there is no wheeled carrier 350 rolling on the floor of the photobioreactor 310, so the thin film of the photobioreactor 310 is not exposed to continual mechanical stress on its surface, which eventually may lead to failure of the film.

Photobioreactors 310 also may deflect horizontally over lengths of, for example, 50 feet. With the exemplary embodiment illustrated in FIG. 16, deflection of more than a few inches may cause a foil 170 to impact the film on the side of a photobioreactor 310 and potentially tear the film, if no guard mechanism is in place, and if the drive conduit 100 and the track 350 are not fixed to an inside surface of the bioreactor 310. In the embodiment illustrated in FIG. 15, if the photobioreactor 310 curves excessively, the wall of the photobioreactor 310 would push the tracking member 340 above the surface 320 of the algae culture and displace the foil assembly 180 laterally, since the drive conduit 100 would offer minimal bending resistance. The tracking members 340 thereby guard against accidental contact between the foils 170 and the film on the sides of the photobioreactor 310.

Figure 17A:
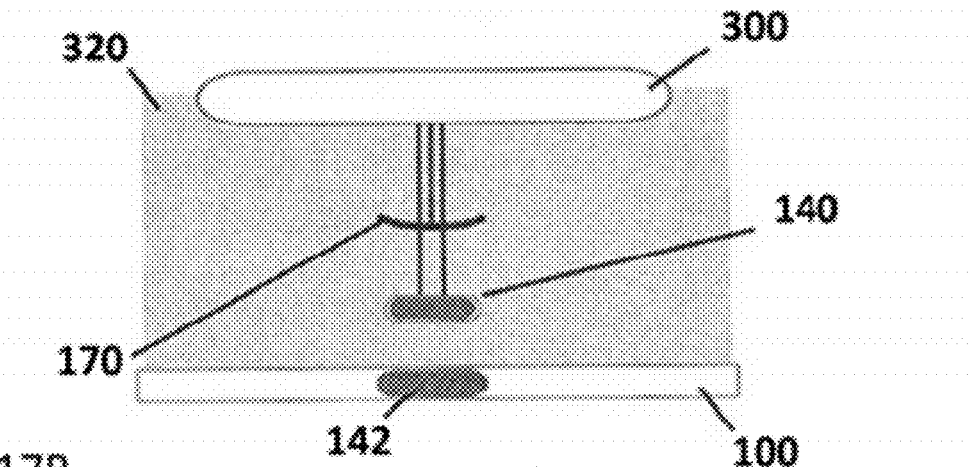
FIGS. 17A-C show side and front views of portions of mixing systems in accordance with certain embodiments of the present invention.
Figure 17B:
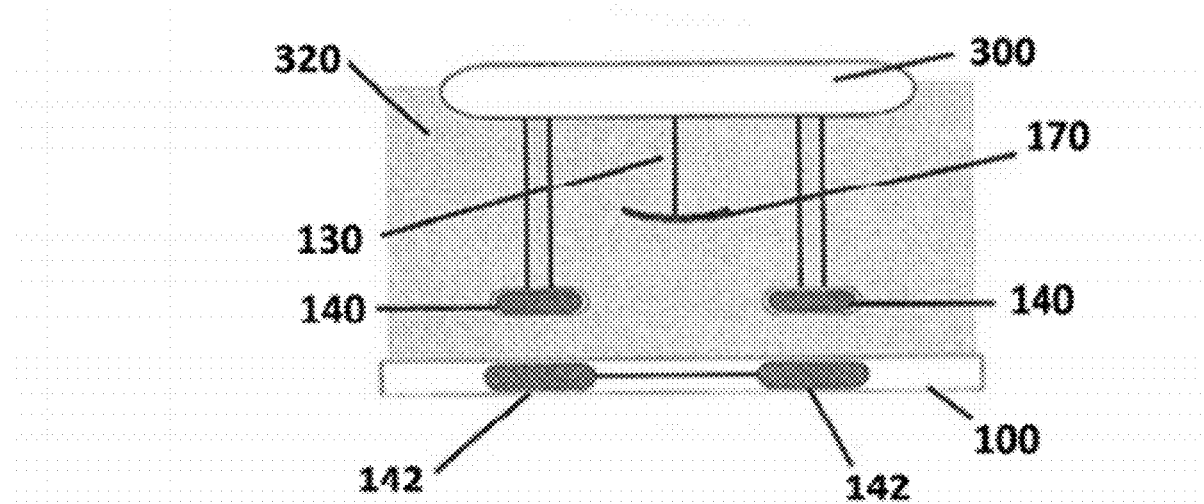
Figure 17C:
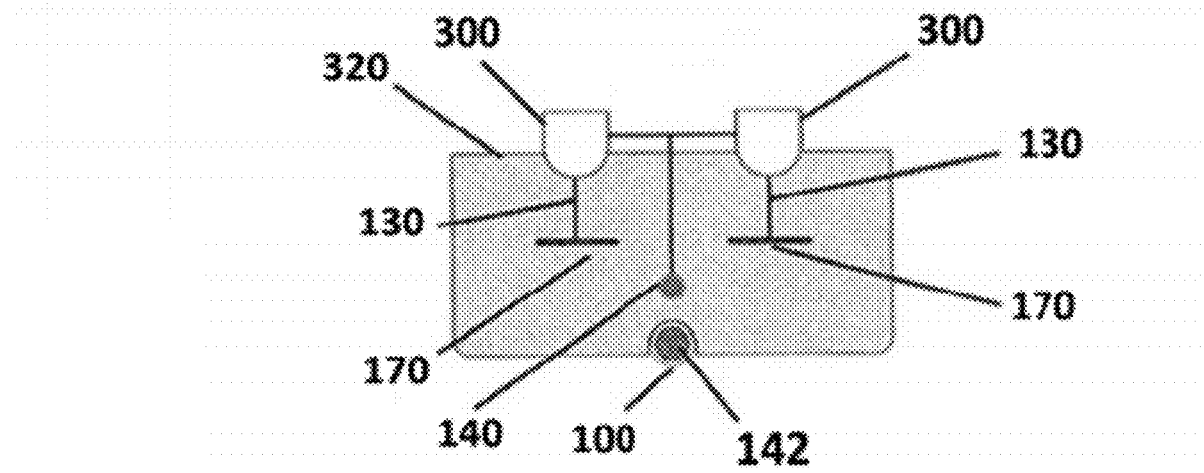

FIGS. 17A-C illustrate exemplary embodiments having a drive conduit 100 positioned underneath, or on any side of, a photobioreactor 310. One or more drive magnets 142 or drive ferromagnets 144 are contained in the drive conduit 100. One or more follower magnets 140 are attached to a flotation member 300 by support members 130 and are magnetically coupled with the drive magnets 142 or drive ferromagnets 144.

Motive Force System

The present invention utilizes a pump 420 to provide motive force to the drive elements 190 in an array of mixing vessels, such as photobioreactors 310. In some embodiments, one pump 420 can drive mixing in multiple vessels.

The pump 420 moves drive fluid through the drive conduit 100. The drive fluid may be, for example, air, water, mineral oil or polyethylene glycol, and the drive fluid may be suffused with agents that inhibit corrosion. In some embodiments, a drive fluid of low density is selected for use in the drive conduit 100 to promote positive buoyancy of the drive conduit 100, in particular if the drive conduit 100 is constructed of materials having high density, such as steel or iron.

Figure 22:
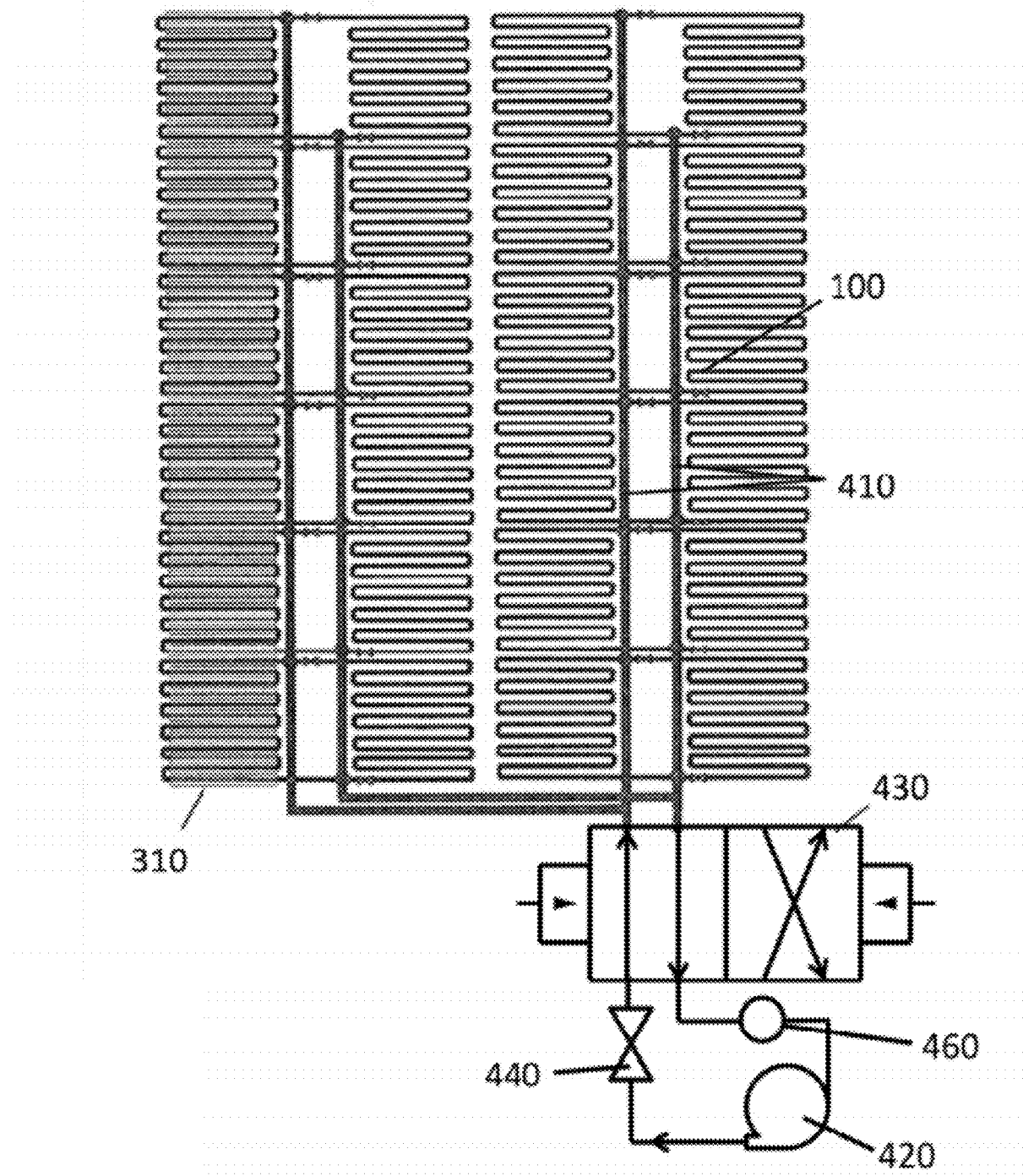
FIG. 22 shows an embodiment of a hydraulic mixing system in accordance with certain embodiments of the present invention.
Figure 24:
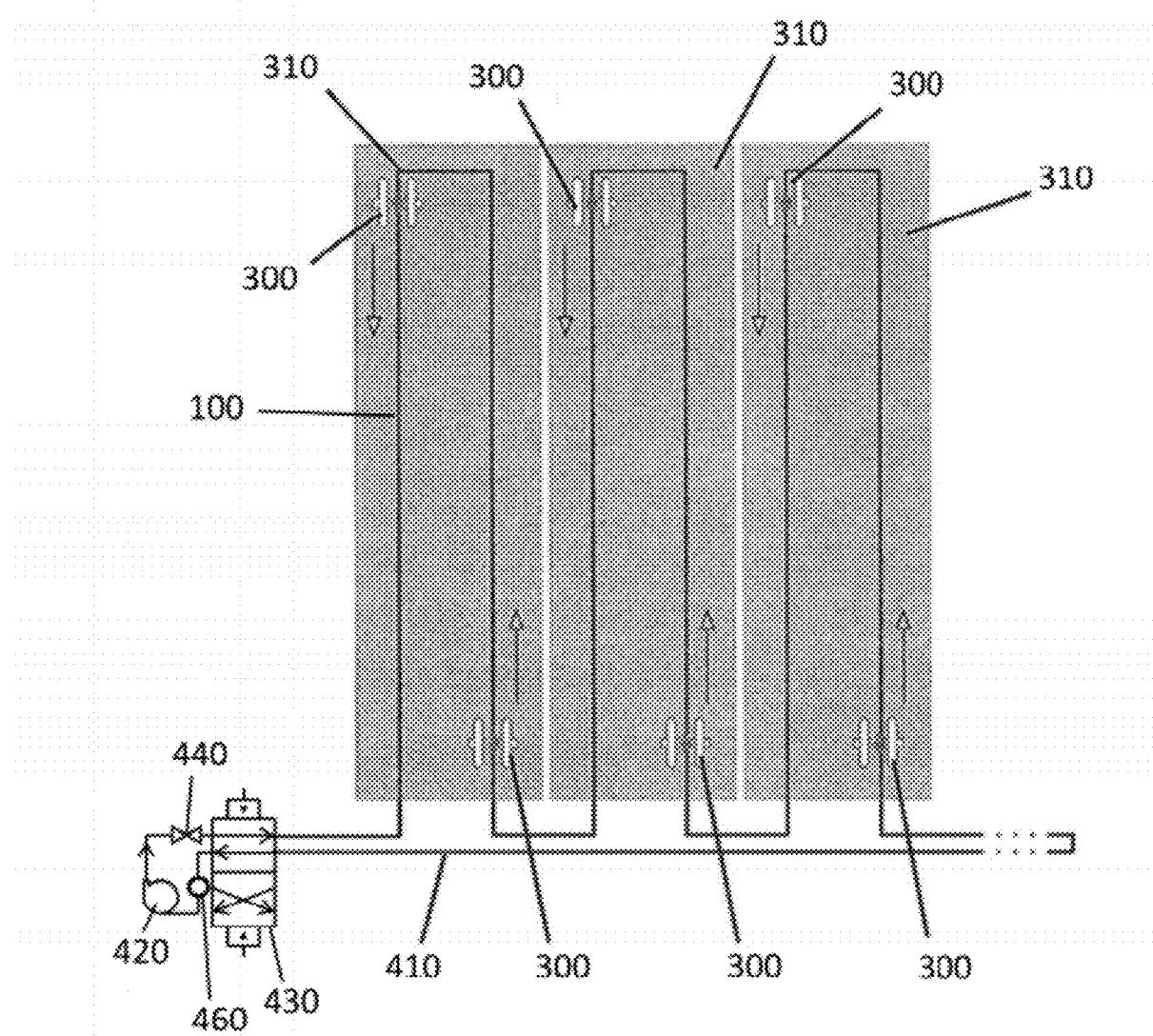
FIG. 24 shows a planform schematic view of a mixing system in accordance with certain embodiments of the present invention.

FIGS. 22 and 24 show exemplary embodiments in Which a drive conduit 100 served by a single pump 420 and a switching valve 430 is routed through multiple photobioreactors 310 in a serpentine configuration. One or more drive elements 190, follower elements 110 and foil assemblies 180 can be disposed inside each photobioreactor 310. In the exemplary embodiment, the pump 420 and switching valve 430 are located outside the photobioreactors 310 and the drive system is closed.

FIG. 22 illustrates an exemplary hydraulic mixing system in which one pump 420 drives mixing in four rows of at least 70 photobioreactors 310 per row. Each row of photobioreactors 310 is partitioned into groups of 12 photobioreactors 310 through which a single drive conduit 100 of 0.5 inch diameter passes. Flow is distributed to the rows of photobioreactors 310 via the drive conduits 100 using a two inch diameter pipe 410. A pump 420 pushes water through the pipes 410 and drive conduits 100 to drive one or more drive elements 190 in the drive conduits 100 in each photobioreactor 310. The drive elements 190 are magnetically coupled to foil assemblies 180, which comprise follower elements 110, follower members 120, foils 170 and connecting support members 130.

The exemplary hydraulic mixing system of FIG. 22 comprises a pump 420 rated at one horsepower, 48 gallons per minute and 200 foot head (approximately 100 pounds per square inch). The exemplary hydraulic mixing system further comprises a four-way air piloted valve 430 adapted to switch the direction of hydraulic flow, a flow control valve 440, a flow meter 450 and an air bleed tank 460. The hydraulic pressure in the pipe 410 is approximately 30 pounds per square inch.

The exemplary hydraulic mixing system of FIG. 22 moves the drive elements 190 and foil assemblies 180 at a constant speed for a preselected length of time. In some embodiments, a length of time greater than 30 seconds is expected to be sufficient for the drive elements 190 and foil assemblies 180 to traverse the full length of a photobioreactor 310. Mechanical stops (not shown) at the ends of each photobioreactor 310 restrict the movement of the drive elements 190 and foil assemblies 180 while hydraulic flow continues for a short period of time to enable the drive elements 190 and foil assemblies 180 to reach the end of each photobioreactor 310. In some embodiments, the short period of time is five to ten seconds.

In the exemplary hydraulic mixing system, the four-way air piloted valve 430 subsequently is activated to reverse the hydraulic flow throughout the drive conduit 100. The activation of this valve 430 preferably occurs slowly enough to avoid dislodging the magnetic coupling between the drive elements 190 and follower elements 110. In some embodiments, the length of time for activation of the valve 430 is greater than 100 milliseconds.

In alternative embodiments, a reversible positive displacement pump 420 with a variable frequency drive is used and the four-way air piloted valve 430 is omitted. The hydraulic flow through the system is controlled to a specified rate.

Energy usage can be reduced by reducing the cross-sectional area of the drive conduit 100 or changing the drive fluid to air. Reducing the cross-sectional area of the drive conduit 100 requires closer tolerances between the drive element 190 and follower element 110 so that smaller magnets can be used. Changing the drive fluid to air requires using a sealing fluid around the drive magnet 142 or drive ferromagnet 144 to avoid wasting energy.

Figure 23:
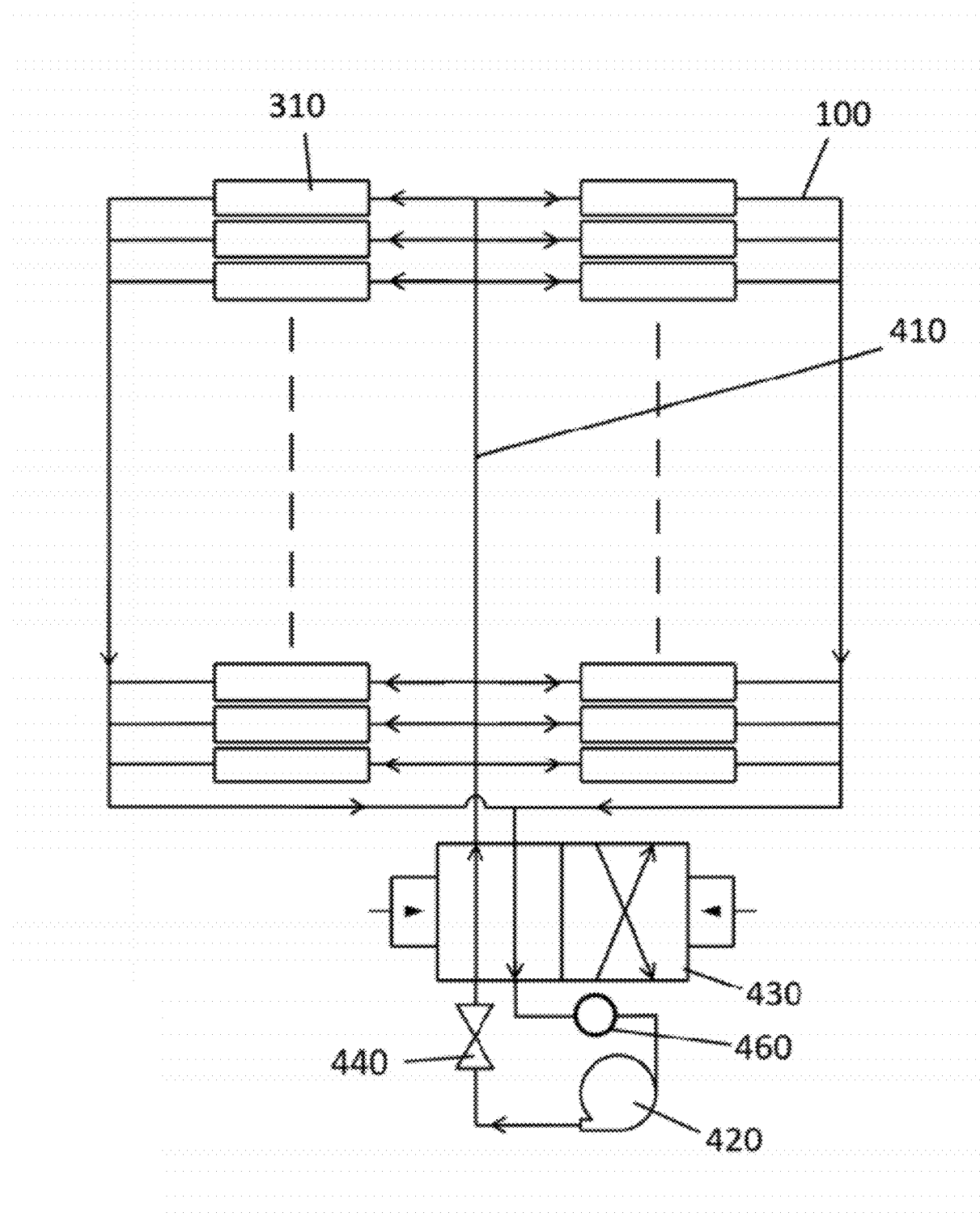
FIG. 23 shows an embodiment of a pneumatic mixing system in accordance with certain embodiments of the present invention.

FIG. 23 illustrates an exemplary pneumatic mixing system in which one pump 420 drives mixing in 240 photobioreactors 310 connected in parallel. Drive conduits 100 of 0.5 inch diameter pass through each row of photobioreactors 310. Flow is distributed to the rows of photobioreactors 310 via the drive conduits 100 using a two inch diameter pipe 410. A pump 420 pushes air through the pipe 410 and drive conduits 100 to drive one or more drive elements 190 in the drive conduits 100 in each photobioreactor 310. The drive elements 190 are magnetically coupled to foil assemblies 180, which comprise follower elements 110, follower members 120, foils 170 and connecting support members 130.

In some embodiments, a system of the present invention incorporates multiple drive elements 190 and foil assemblies 180 in one mixing vessel. The foil assemblies 180 are disposed on the drive conduit 100 at selected distance intervals and are driven by the same motive system. The foil assemblies 180 may be configured and spaced to provide mixing over the full length of the mixing vessel, wherein each foil assembly 180 provides mixing for a selected portion of the mixing vessel. One of ordinary skill will appreciate that the lowest energy consumption required to achieve a desired degree of vertical mixing in a photobioreactor 310 can be determined by varying the number and configuration of foil assemblies 180 that are used in the photobioreactor 310.

FIG. 24 illustrates an embodiment in which multiple photobioreactors 310 are serviced by one pump 420 and one drive conduit 100. The photobioreactors 310 are connected in series. In this embodiment, multiple foil assemblies 180 are disposed inside each photobioreactor 310 and are configured to traverse the length of the bioreactor in opposite directions.

Figure 25:
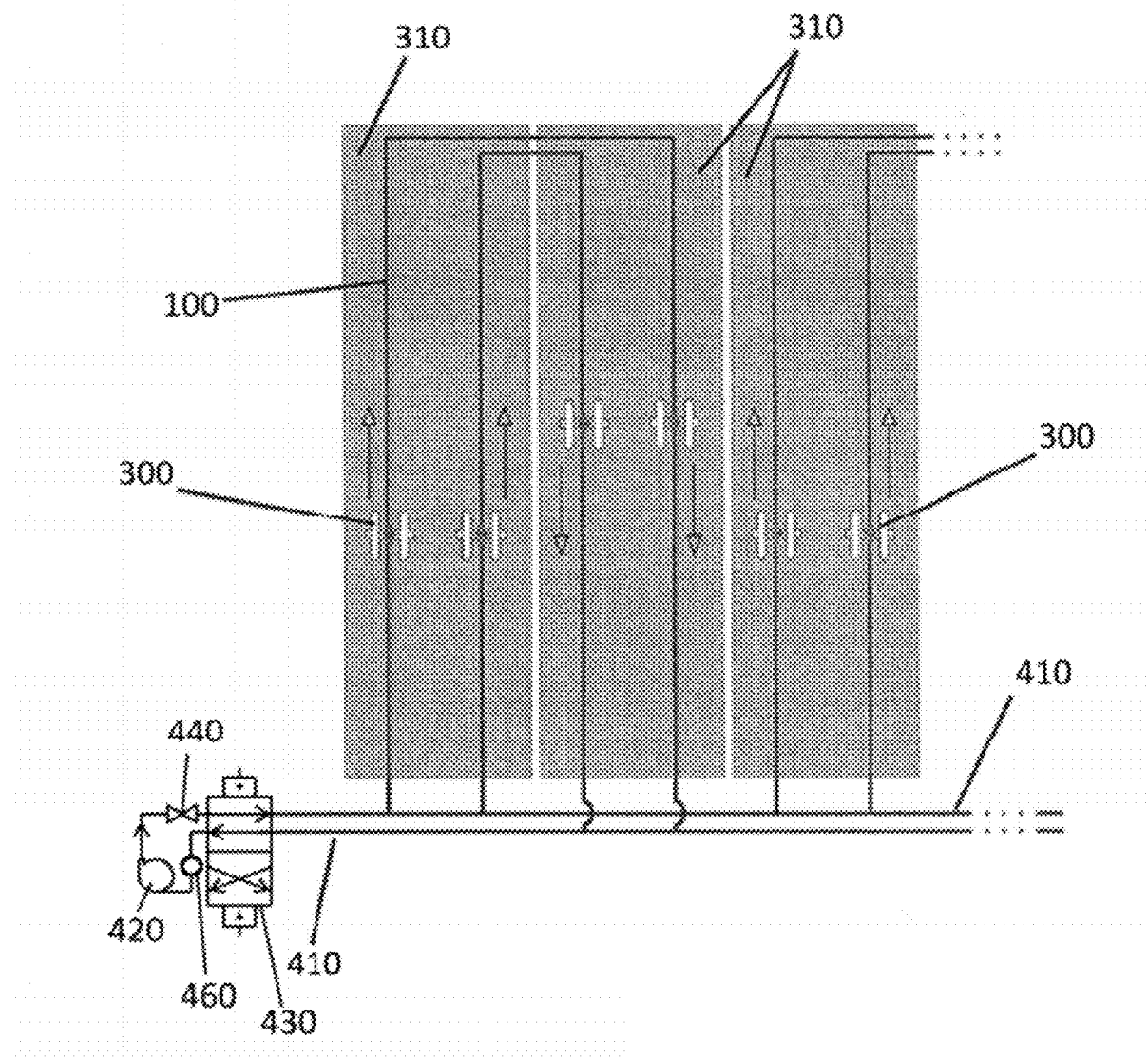
FIG. 25 shows a planform schematic view of a mixing system in accordance with certain embodiments of the present invention.

FIG. 25 illustrates an embodiment in which multiple photobioreactors 310 are serviced by one pump 420 and multiple drive conduits 100 that are fed by a header pipe 410. Pairs of photobioreactors 310 are connected in parallel, and the photobioreactors 310 in each pair are connected in series. In this embodiment, multiple foil assemblies 180 are disposed inside each photobioreactor 310 and are configured to traverse the length of the bioreactor in the same direction.

In embodiments of the present invention that utilize pneumatic force to move foil assemblies 180, multiple foil assemblies 180 may be disposed inside each photobioreactor 310, while multiple photobioreactors will be connected in parallel, instead of in series. As shown in FIG. 45, multiple drive elements 190 are tethered by a connector 252, which may be any flexible or rigid elongate member made of, for example, plastic, nylon or elastomer, that physically connects the drive elements 190. Unidirectional floating seal grooves 222 are formed in the drive elements 190 positioned at the distal end of each chain of drive elements 190. When pneumatic motive force is applied, the unidirectional floating seal groove 222 formed in the drive element 190 in the upstream position allows gas to slip underneath the o-ring 220 and prevent the formation of a seal. A seal is instead formed by the o-ring 220 present in the downsteam drive element 190. The downstream drive element 190 moves in the direction of the pneumatic motive force and pulls the upstream drive element 190 in the same direction. If the chain of drive elements 190 includes three or more drive elements 190, then only the drive element 190 at the upstream end of the chain and the drive element 190 at the downstream end of the chain have o-rungs 220, so that no seals are formed by the drive elements 190 positioned in the interior of the chain.

In embodiments of the present invention that utilize hydraulic force to move foil assemblies 180, a disadvantage of servicing multiple vessels in series using one pump 420 is that an increased pressure drop caused by a decreased rate of mixing in one vessel, such as due to a stopped drive element 190, affects mixing speed in all other vessels in the array. In some embodiments, a system of the present invention comprises a positive displacement pump 420, such as a vane pump, for the purpose of rendering flow rate through the pump 420 independent of pressure variations and providing consistent mixing speed in the array of vessels.

Figure 18:
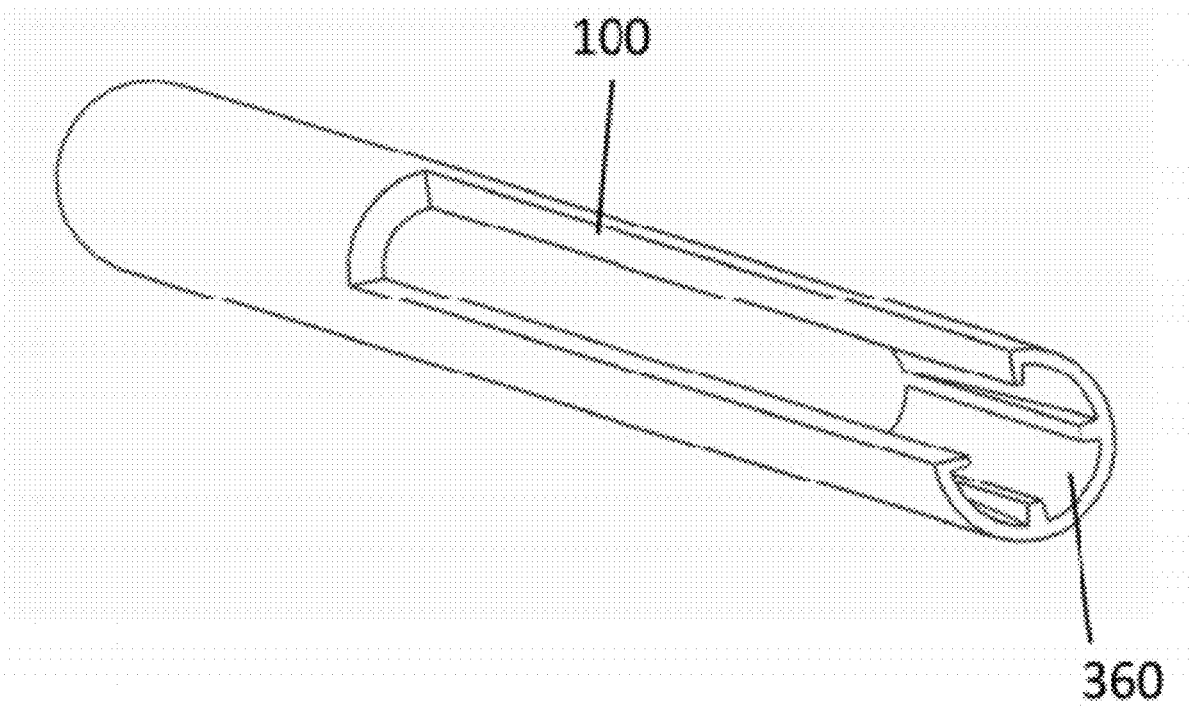
FIG. 18 shows a sectional perspective view of an embodiment of a drive conduit.

Operating pressure in a system of the present invention utilizing hydraulic force is approximately 32 pounds per square inch, while maximum pressure induced by stoppages of the drive elements 190 in twelve mixing vessels may be as high as 360 pounds per square inch. A large pump motor 420 may generate sufficient torque to maintain constant mixing speed under temporary large pressure drops in the mixing system but will not operate efficiently under smaller pressure drops that are typical during normal operation of the mixing system, when no drive elements 190 are stopped. With reference to FIG. 18, in some embodiments, the conduit used in a system of the present invention allows flow past a stopped drive element 190 and reduces the pressure drop, which reduces the size of the pump motor 420 needed for the system, by incorporating a small channel 360 between the surface of the drive element 190 and the inner surface of the drive conduit 100. The channel 360 is sufficiently small to maintain motive force in the form of pressure from a drive fluid applied to the drive element 190 under normal operation, and the change in outside diameter of the drive conduit 100 is sufficiently small to avoid interference with a follower element 110. If channels 360 are formed in the inner surface of the drive conduit 100 and the outside diameter of the drive conduit 100 is unchanged, a higher schedule drive conduit 100 must be selected to compensate for the loss of pressure capability in the drive conduit 100.

Figure 19A:
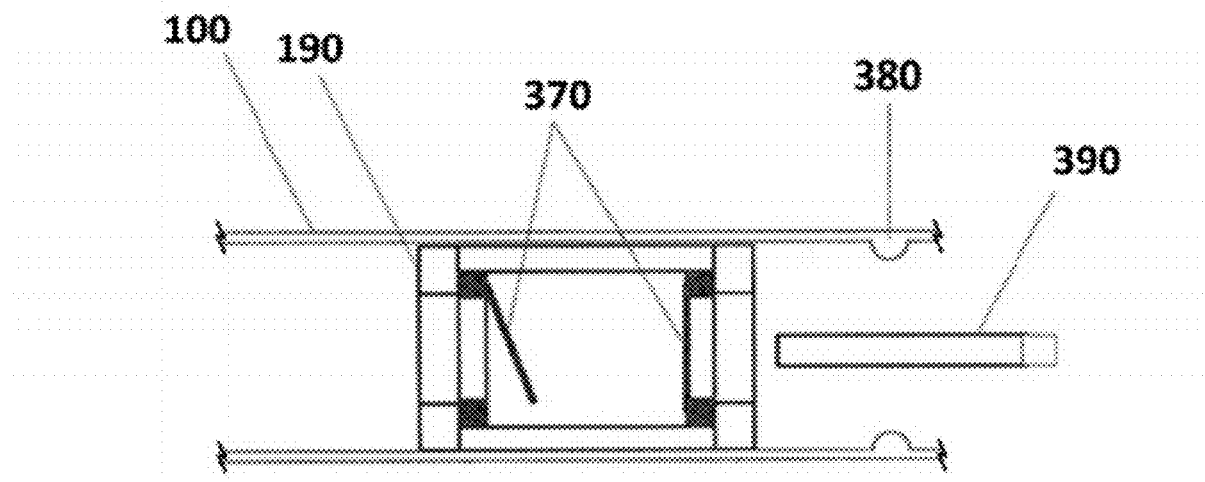
FIGS. 19A and B show sectional views of a drive element in accordance with certain embodiments of the present invention.
Figure 19B:
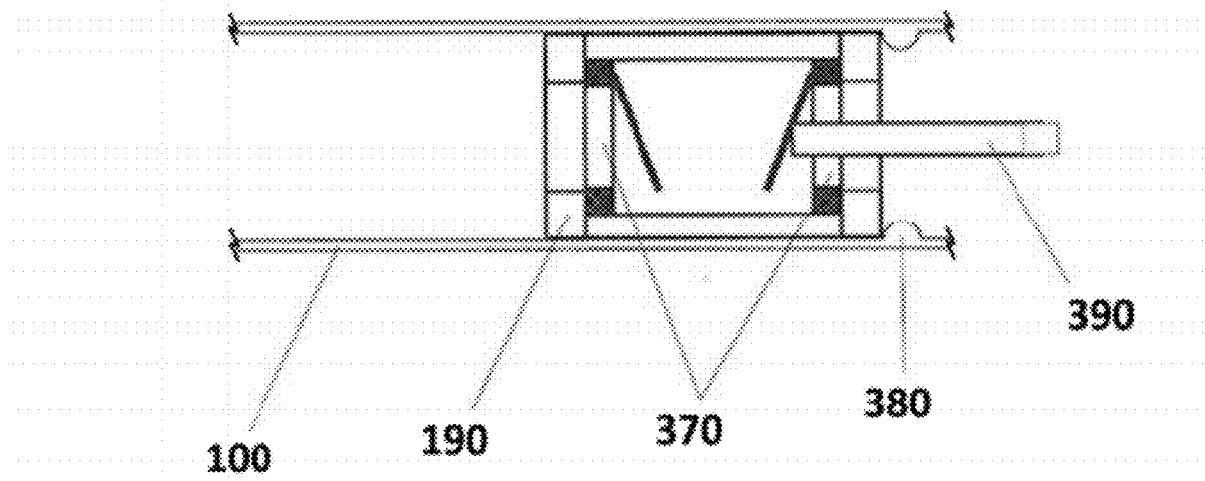
Figure 20A:
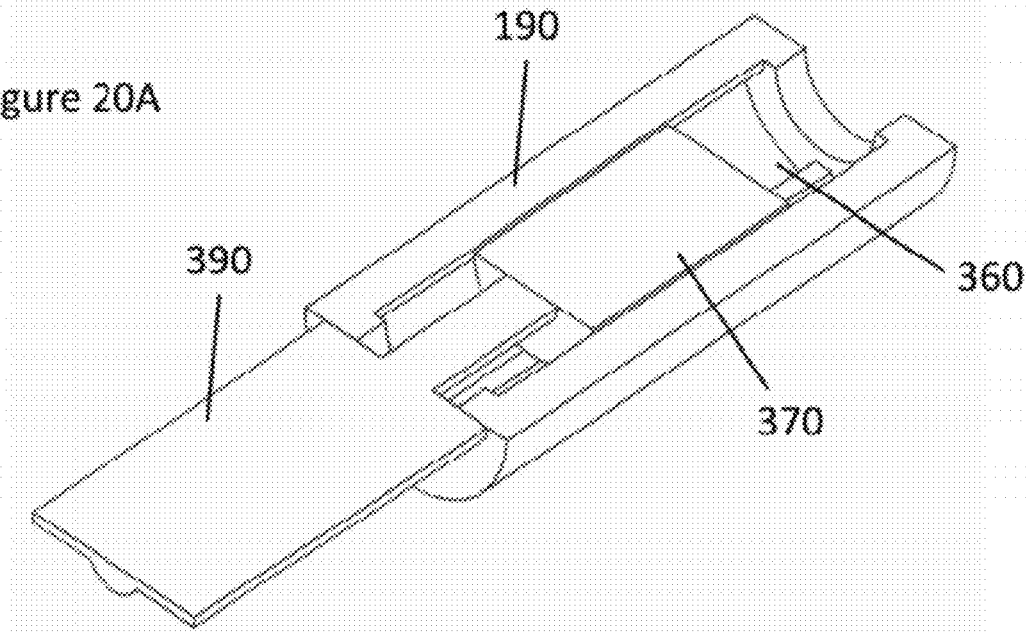
FIGS. 20A and B show sectional and end views of a drive element in accordance with certain embodiments of the present invention.
Figure 20B:
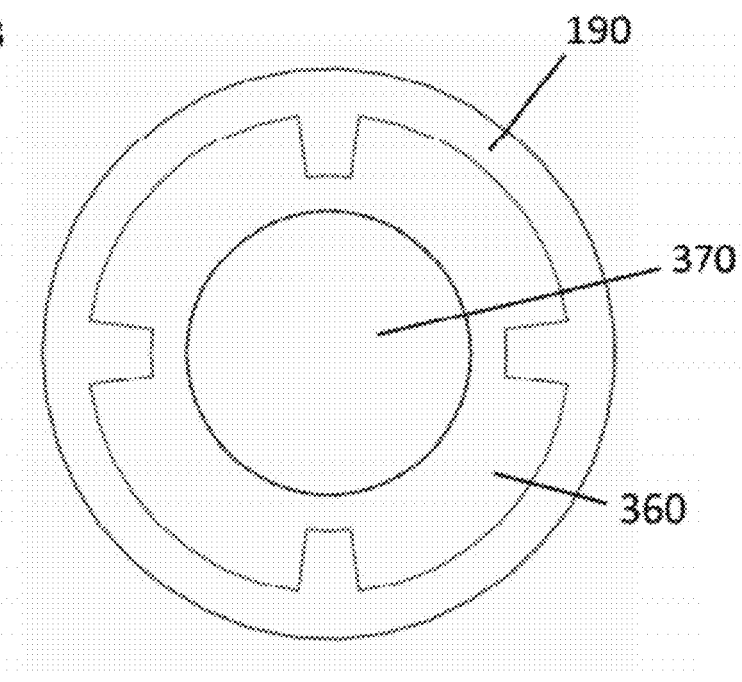

As illustrated in FIGS. 19A and B and FIGS. 20A and B, in some embodiments, the drive element 190 incorporates a poppet valve 370. If a misaligned or otherwise impeded drive element 190 creates a blockage in the drive conduit 100, the poppet valve 370 is adapted to allow drive fluid to flow through the drive element 190 and provides an alternative means of releasing pressure. In some embodiments, the internal surface of the drive conduit 100 incorporates drive stops 380 that restrict the motion of the drive element 190 in a longitudinal direction within the drive conduit 100. In some embodiments, a valve opening pin 390 is adapted to actuate the poppet valve 370.

Figure 21A:
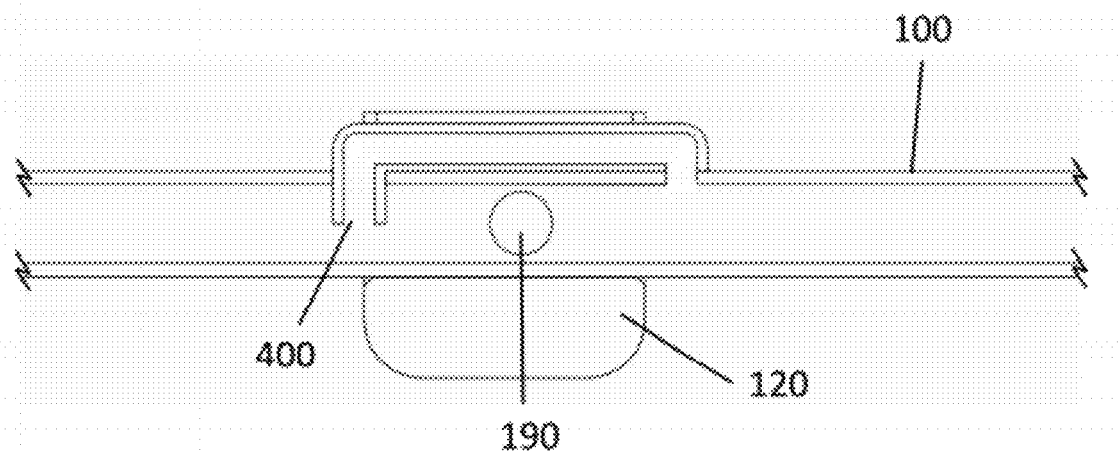
FIGS. 21A and B show sectional and end views of a follower member and bypass conduit in accordance with certain embodiments of the present invention.
Figure 21B:
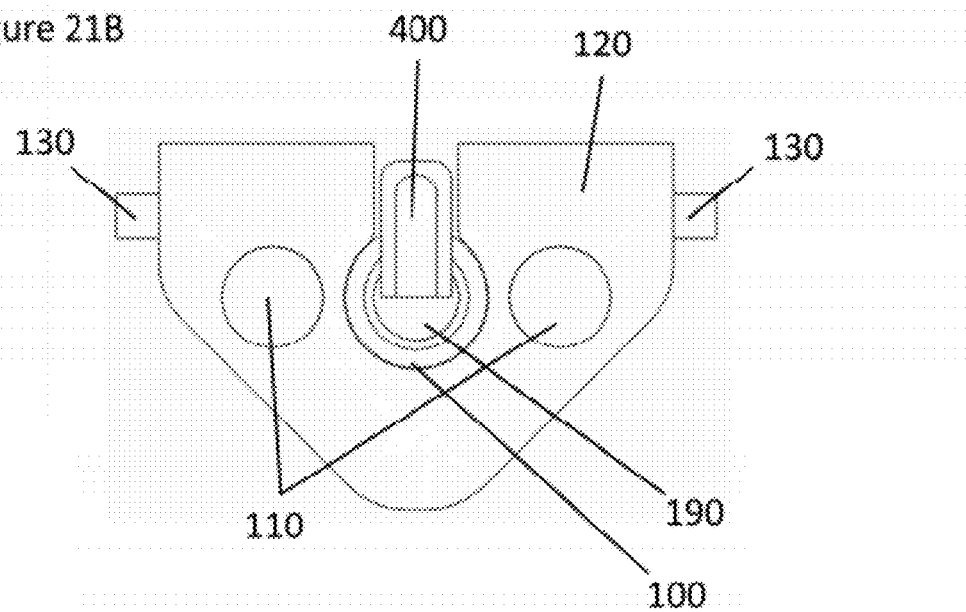

As illustrated in FIGS. 21A and B, some embodiments comprise a bypass conduit 400 that is formed in the drive conduit 100. The bypass conduit 400 is adapted to relieve fluid pressure by diverting the flow of drive fluid in the event that a blockage occurs in the drive conduit 100 between the inlet and outlet of the bypass conduit 400. In some embodiments, the follower member 120 is shaped to accommodate the placement of the bypass conduit 112.

Figure 26:
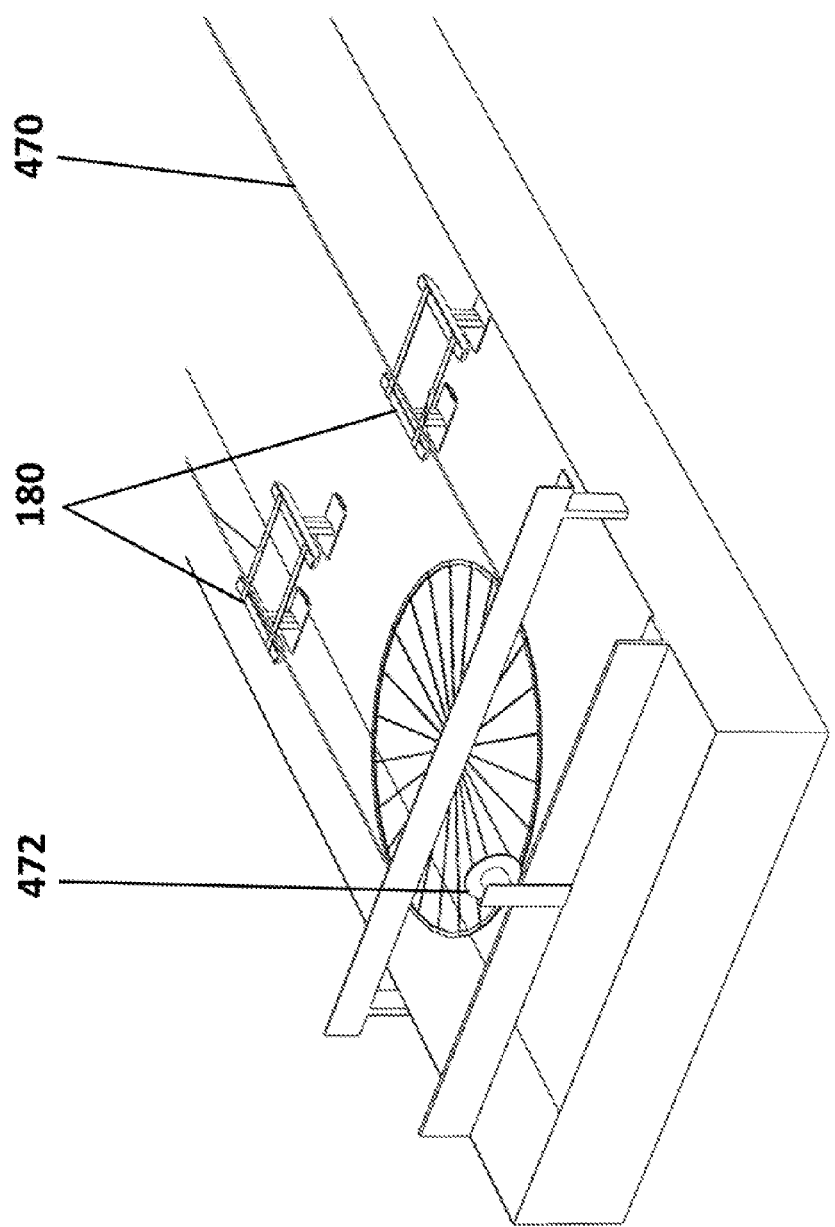
FIG. 26 shows a cable driven mixing system in accordance with certain embodiments of the present invention.
Figure 27:
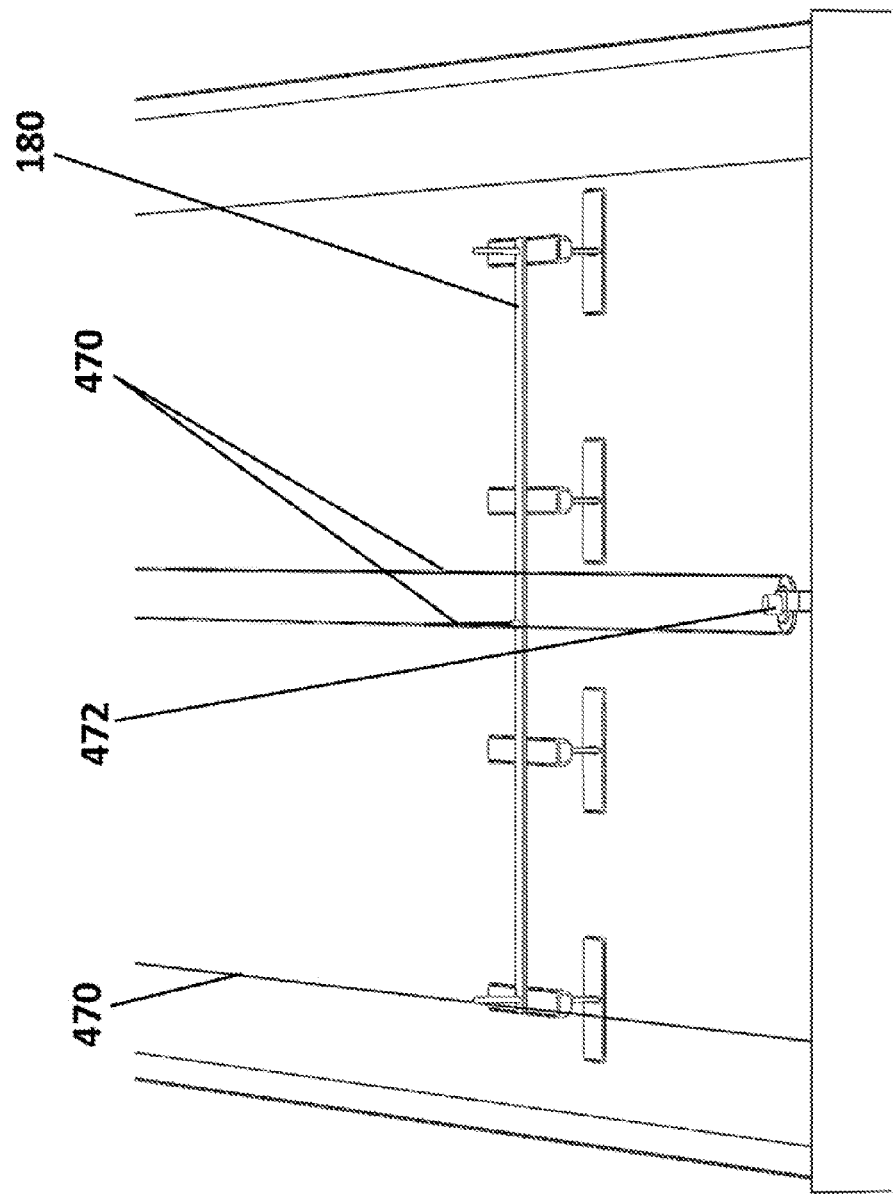
FIG. 27 shows a cable driven mixing system in accordance with certain embodiments of the present invention.
Figure 28:
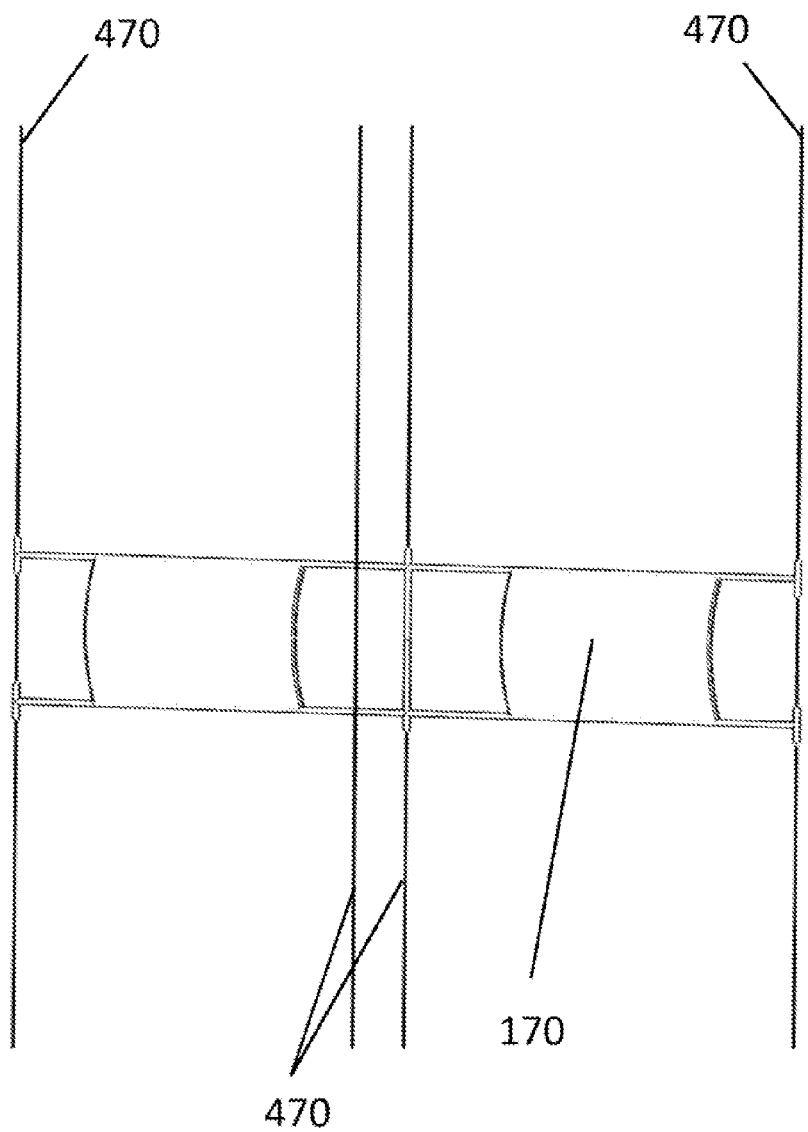
FIG. 28 shows an embodiment of a foil in accordance with certain embodiments of the present invention.

As illustrated in FIGS. 26, 27 and 28, in some embodiments the motive system is a cable connected system. A cable 470 attaches to a foil 170 and/or to flotation members 300 in a foil assembly 180. The cable 470 is pulled by a motor 472 that is configured to pull the cable 470 in more than one direction. The foil 170 is moved by actuating the motor 472 to pull the cable 470, and the cable 470 is wound on a spool 474 at either end of the mixing vessel depending on the direction of travel.

Foil Design

A system in accordance with certain embodiments of the present invention comprises a surface, or foil 170, that is shaped to provide hydrodynamic lift, wherein the foil 170 can be moved through an aqueous culture of algae to efficiently generate a vertical movement of algae. FIGS. 14, 15, 16 and 28 illustrate exemplary foils 170 used in a mixing system of the present invention. It is desirable to induce flow with the lowest velocity needed to provide satisfactory mixing while minimizing energy consumption. Net vertical flow of the aqueous culture in the mixing vessel is zero. In the lowest energy case, upward and downward velocities are equal and act over equal areas.

FIG. 14 illustrates idealized vertical fluid motion in trailing vortices 330 generated by foils 170 in a photobioreactor 310. The trailing vortices 330 remain stationary in the middle of the photobioreactor 310 due to net cancelation of induced velocity from image vortices (not shown) that are created at the top and bottom of the aqueous culture. Generating trailing vortices 330 in the center of the photobioreactor 310 may maximize the mixing length, or vertical particle displacement, over which the vortices 330 can transport flow. Trailing vortices 330 in the center of the photobioreactor 310 form a stable arrangement and tend not to migrate in location. In contrast, pairs of counterrotating vortices 330 move vertically in unbounded flows or move laterally near a horizontal surface.

In the exemplary embodiment, foils 170 distributed along the span of a photobioreactor 310 provide a regular arrangement of mixing vortices 330 that minimize the presence of dead zones with no mixing. Such mixing is sufficient to sustain algae cultures over extended periods of time. Aqueous algae cultures can die from anoxia due to reduced gas exchange and sedimentation of the algae if mixing is stopped for a period of several hours.

A foil assembly 180 generally may be moved at a higher speed with downwardly concave foils 170, instead of upwardly concave foils 170. However, downwardly concave foils 170 produce trailing vortices 330 that induce sedimentation of algae in regions away from the foils 170, while upwardly concave foils 170 produce trailing vortices 330 that rotate in the opposite direction and induce sedimentation of algae in the region underneath the foil 170. Additional mixing and resuspension of settled algae may be facilitated to a greater extent by a pattern of sedimentation underneath the foil 170 rather than sedimentation away from the edges of the foil 170.

The migratory speed of trailing vortices 330 can be predicted by determining the velocity a vortex 330 will induce on its neighbor, according to potential flow theory and in situations with surfaces, including the effect of image vortices. For a vortex 330 near a single horizontal surface, such as the bottom of the photobioreactor 310, the image vortex (not shown), which is a vortex 330 with opposite rotation placed equidistant but on the opposite side of the horizontal surface, will induce the actual vortex 330 to move laterally with a certain speed. When the actual vortex 330 is bounded on the opposite side by a second horizontal surface, which is the top surface 320 of the liquid mixture in exemplary embodiments of the present invention, the image vortex from this surface 320 will induce a directed motion countering the induced motion from the lower surface. If the vortex 330 is centered between these two surfaces, then the induced effect cancels completely and the vortex 330 remains stationary. The stability of the vortex 330 position allows for subsequent passes of a foil 170 to reinforce the strength of the vortex 330.

The trailing vortices 330 decay slowly and are continually reinforced as the foils 170 longitudinally traverse the photobioreactor 310 in either direction, allowing the foils 170 to effectively mix a large area of aqueous culture in the vessel compared to the planform area of each foil 170. This efficiency reduces the amount of equipment needed for mixing and capital costs.

The preferred placement of the foil 170 is middepth in the aqueous culture, with the span of the foil 170, and the lateral spacing between foils 170, equal to the depth of the culture. This placement produces a stable configuration of trailing vortices 330.

The trailing vortices 330 are strengthened by increasing the lift generated by the foil 170. Lift is controlled by the planform area, angle of attack, camber and speed of the foil 170. The trailing vortices 330 are also reinforced by multiple passages of each foil 170, which can be increased by increasing foil 170 speed for a photobioreactor 310 of a fixed length or by employing multiple foil assemblies 180 along the length of one photobioreactor 310. Foils 170 can be spaced equidistant along the transverse axis of the photobioreactor 310 to reduce the tine over which a trailing vortex 310 will decay before reinforcement and thereby achieve desired recirculation with uniformity and low power requirements.

Figure 29:
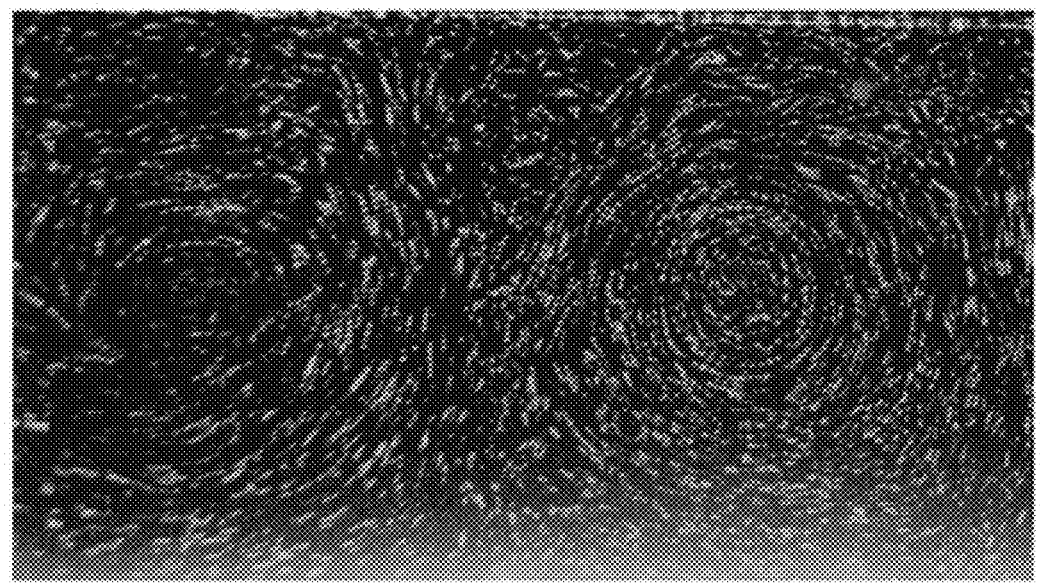
FIG. 29 shows trailing vortices and vertical mixing generated by horizontal movement of a foil in a mixing system in accordance with certain embodiments of the present invention.

FIG. 29 illustrates measurements of a trailing vortex 330 pair generated by a single foil 170 in an algae culture having a depth of eight inches. The particle traces shown cover the depth of a photobioreactor 310, eight inches, and show the flow pattern of the particles after the passage of one foil 170. Movement of the foil 170 (not shown) is in a plane perpendicular to the plane of the image. The trailing vortices 330 were generated by the distal ends of a foil 170 designed to produce similar recirculation times in the aqueous culture when the foil 170 longitudinally traverses the photobioreactor 310 at mid-depth in the algae culture. The foil 170 shape is symmetric and cambered to generate a vortex 330 system with rotations that are independent of the direction of traverse. The trailing vortices 330 were measured through laser diagnostics. The particles are neutrally buoyant and were illuminated with a laser light sheet. Four consecutive exposures are superimposed in this image to show the movement of the particles over intervals of 66.7 milliseconds. Total plotted time for each particle is therefore 4×66.7 milliseconds=0.26 seconds.

Figure 30:
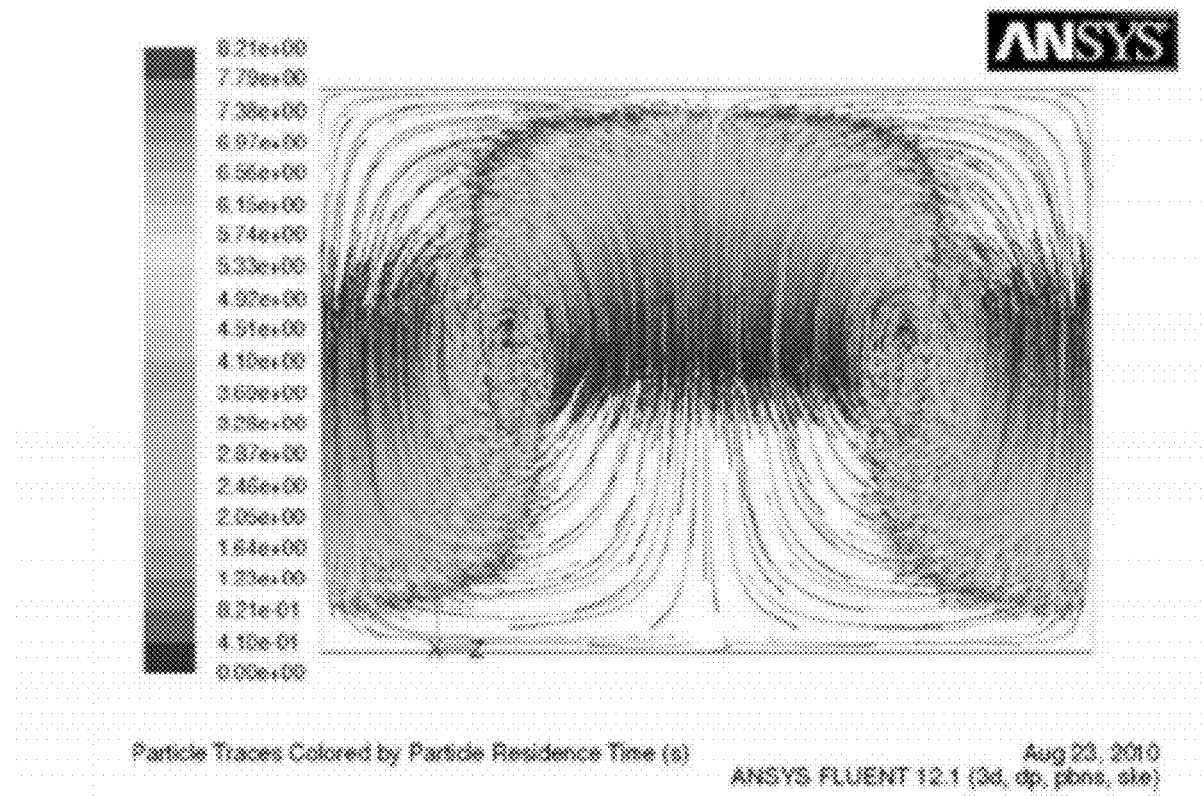
FIG. 30 shows a computational simulation of trailing vortices and vertical mixing generated by horizontal movement of a foil in a mixing system in accordance with certain embodiments of the present invention.

FIG. 30 illustrates a computational simulation of trailing vortices 330 generated by a foil 170 passing through an algae culture with a depth of eight inches. This image provides the same view of particle traces shown in FIG. 29. Each trace in FIG. 30 represents a total travel time of 8.21 seconds per particle. Particles in this simulation are nonuniformly distributed at an initial time measurement, with most of the particles being located at mid-depth in the algae culture in a photobioreactor 310 at time=0 seconds. For a given position along the length of the algae culture in the photobioreactor 310, the vortices 300 decay over time and must be reinforced or regenerated by the periodic passage of the foil 170. The maximum time to reinforce trailing vortices 330 is roughly 30 seconds between passages for a foil 170 travelling at 0.5 meters per second.

Figure 31:
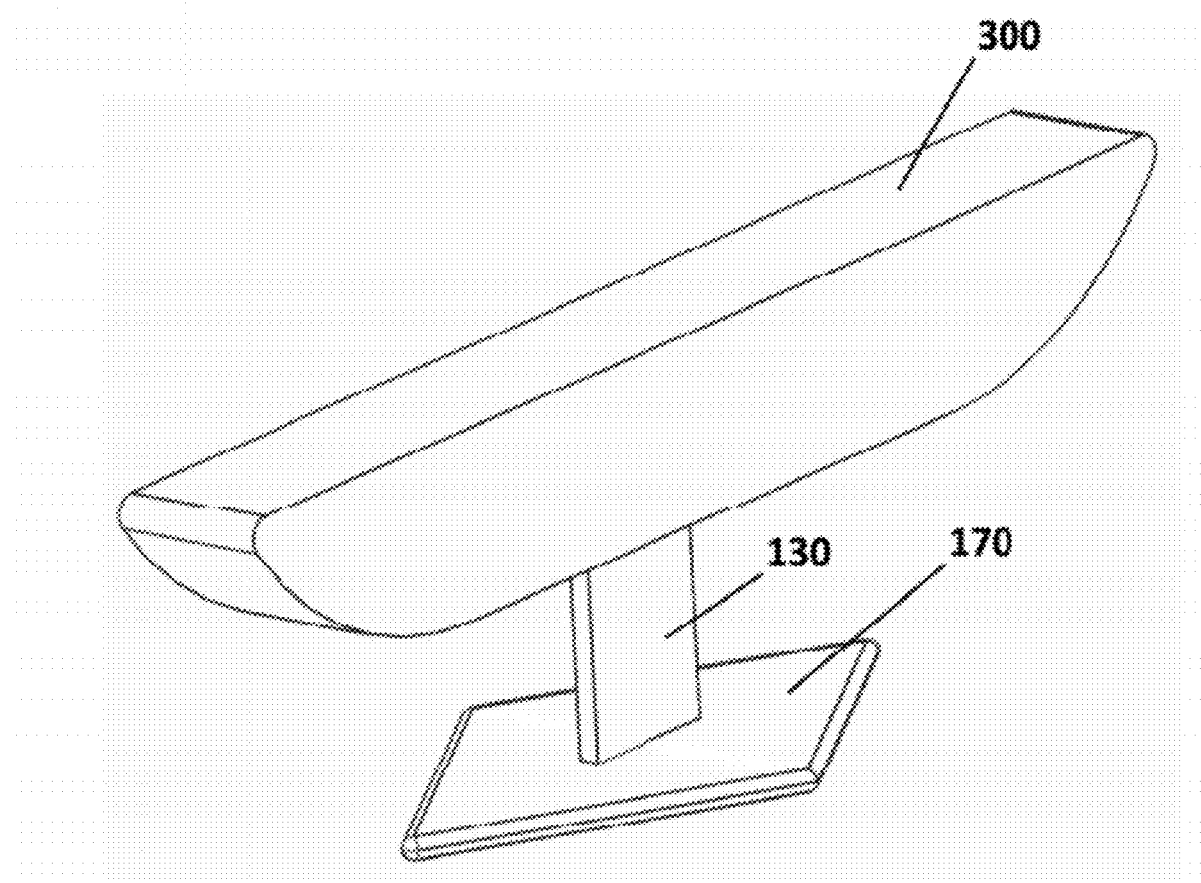
FIG. 31 shows a foil and a flotation member in accordance with certain embodiments of the present invention.

In some embodiments, the foil assembly 180 comprises a symmetric, cambered foil 170. One of skill in the art will recognize that other configurations are also suitable to produce effective mixing and generate trailing vortices 330. Trailing vortices 330 can be generated by hydrodynamic drag on flat foils 170 that have no camber and are held at a constant angle of attack as the foils 170 traverse a photobioreactor 310. FIG. 31 illustrates a foil 170 with a quadrangular planform shape that can produce hydrodynamic lift.

Figure 32A:
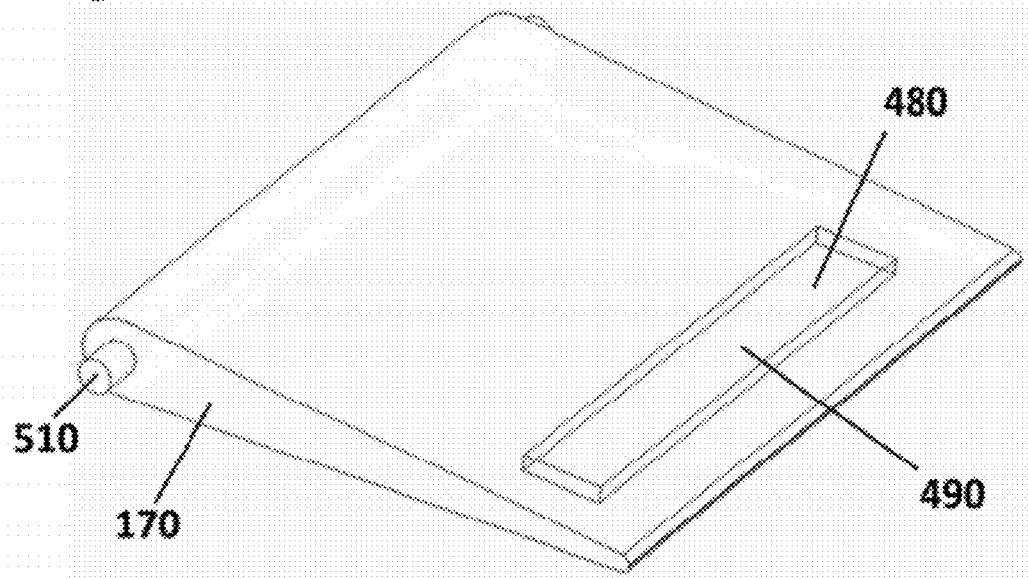
FIGS. 32A and B show foils in accordance with certain embodiments of the present invention.
Figure 32B:
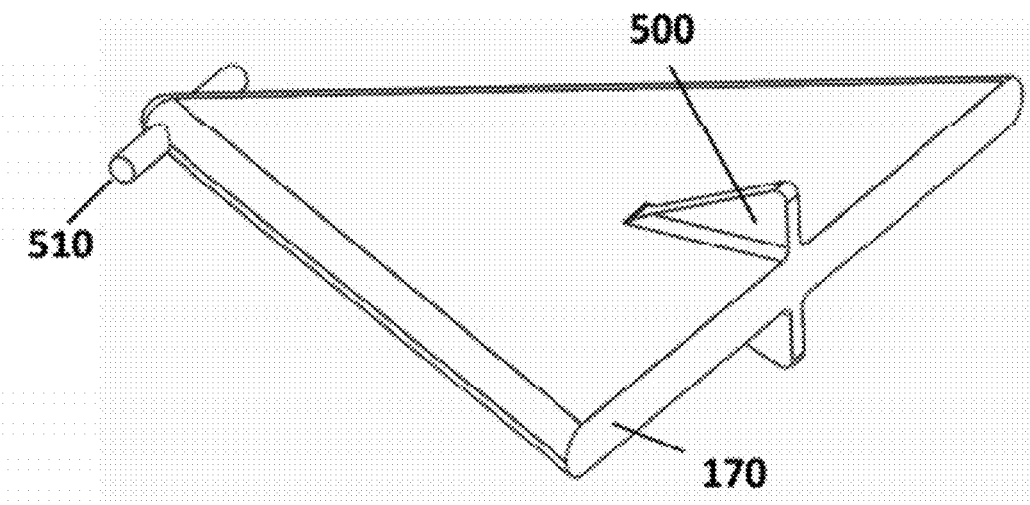

FIGS. 32A and B illustrate exemplary foils 170 that are mounted on axles 510 connected to the foil assembly 180 and are adapted to swivel or pivot to an inclined orientation. The angle of attack, or pitch, of the foil 170 may be maintained by differential weighting along the chord of the foil 170. Triangular and quadrangular planform shapes are suitable for foils 170 of these embodiments. Differential weighting between the sum of the hydrodynamic lift and the weight of the foil 170 may be adjusted by incorporating a weight 480, or an interstitial space 490, embedded in the foil 170. The angle of attack and the amount of circulation generated may thereby be varied and adjusted.

With respect to foils 170 that incorporate embedded weights 480, care must be taken to ensure that the trailing edges of foils 170 with long chords do not scrape the bottom of the mixing vessel during a reversal in travel direction of the foil 170, as the foil 170 swings underneath the axle 510. With a buoyant trailing edge incorporating an interstitial space 490, this is avoided since the trailing edge of the foil 170 would swing over the axle 510.

With reference to FIGS. 32A and B, foils 170 that swivel preferably incorporate a rudder 500 to prevent yaw while avoiding the need to pull the foil 170 from a shifting forward location.

FIGS. 33A and B illustrate an embodiment comprising foils 170 positioned in a vertical orientation. Trailing vortices 330 can be generated by vertical foils 170 that are oriented at slight angles to the direction of the foil 170 movement. In some embodiments, the vertical foils 170 have a triangular planform shape.

In some embodiments, foils 170 are made from molded plastic, fiberglass, sintered nylon, glass-reinforced plastic, or any other material that is suitable to provide rigidity, durability, and positive or neutral buoyancy.

FIGS. 34A-D illustrate an embodiment comprising vertically-oriented foils 170 that are designed increase the extent of mixing directly beneath a horizontally-oriented, upwardly concave foil 170 in region where settling may occur. The two vertically-oriented foils 170 are set in opposition to yield net zero horizontal lift. The two vertically-oriented foils 170 create a set of trailing vortices 330 that impinge on the liquid culture directly beneath the vertically-oriented foils 170 and create a high shear zone that promotes mixing and reduces sedimentation beneath the foils 170.

FIGS. 35A and B illustrate the use of a chain 520 or other suitable flexible dredging member to reduce sedimentation in the aqueous culture. In this exemplary embodiment, a chain 520 is attached to, and suspended from, the foil 170 and drags through the space beneath the foil 170 where sediment accumulates.

If sedimentation is a more severe problem than the need for vertical mixing, foils 170 can be omitted from the foil assembly 180 and a uniform brush 530 can be attached to the foil assembly 180 instead, as illustrated in FIGS. 35C and D. The density of the brush 530 bristles must be sparse enough to avoid excessive hydrodynamic drag forces. Sufficient downward force must be applied to the brush 530 by, for example, utilizing the weight of the support to scrape settled algae from the bottom of the mixing vessel.

As illustrated in FIG. 36, a foil 170 can be rotatably attached to a vertical support member 130 at a pivot point 540. When the foil 170 is traversing the photobioreactor 310, the opposing force exerted by the algae culture causes the foil 170 to rotate away from the direction of travel, thereby tilting the foil 170 and holding the foil 170 at an angle of attack. This effect creates hydrodynamic drag and turbulence at the trailing edge of the foil 170, which enhances mixing. When the foil 170 reverses direction, the foil 170 swings in the opposite direction in a pendulum fashion and correspondingly creates turbulence and mixing in the same manner.

Supporting Structure

There are several ways to maintain the foil 170 at a constant pitch and with minimal roll. In an exemplary embodiment illustrated in FIG. 28, the foil 170 is attached to tensioned guidelines 470. Thin rods are attached to the leading and trailing edges of the foil 170.

In embodiments shown in FIG. 31 and FIGS. 35-D, the foil 170 is attached to a flotation member 300, such as, for example, a pontoon, which reduces frictional losses. The wave pattern generated by the leading end of the flotation member 300 additionally increases mixing at the surface 320 of the algae culture to enhance gas exchange, light penetration and photosynthesis. Counter-rotating longitudinal vortices 330 near the surface 320 are also generated in the wake of the flotation member 300 and can be enhanced by specific hull designs. The width and lateral weight distribution of the flotation member 300 control roll, which is essential to maintain the foil 170 at a constant depth, while the length of flotation member 300 controls pitching and thus the angle of attack of the foil 170.

Figure 37A:
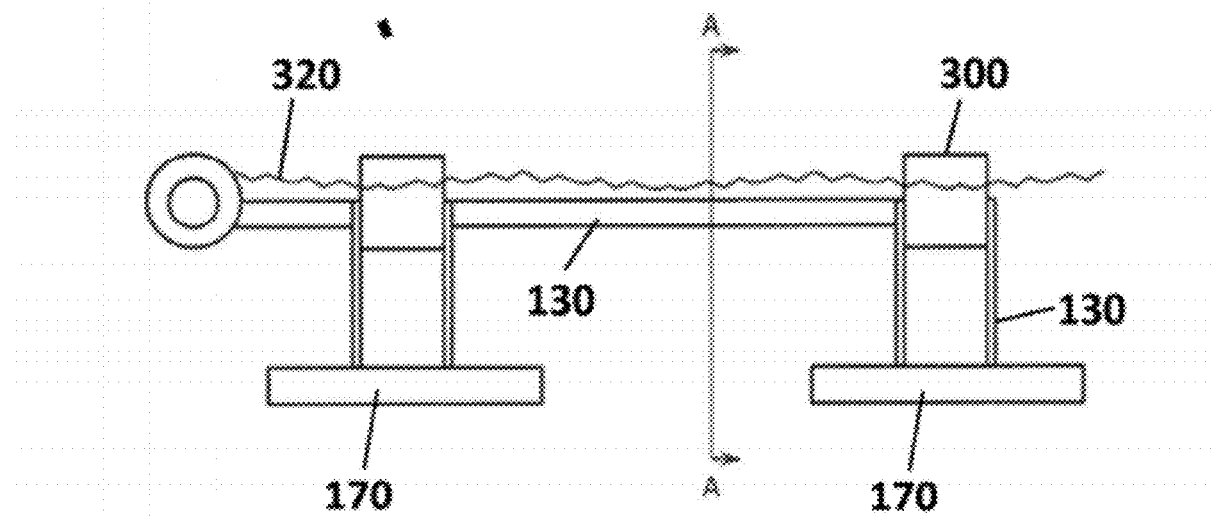
FIGS. 37A and B show a portion of a mixing system having a cambered horizontal support member in accordance with certain embodiments of the present invention.
Figure 37B:
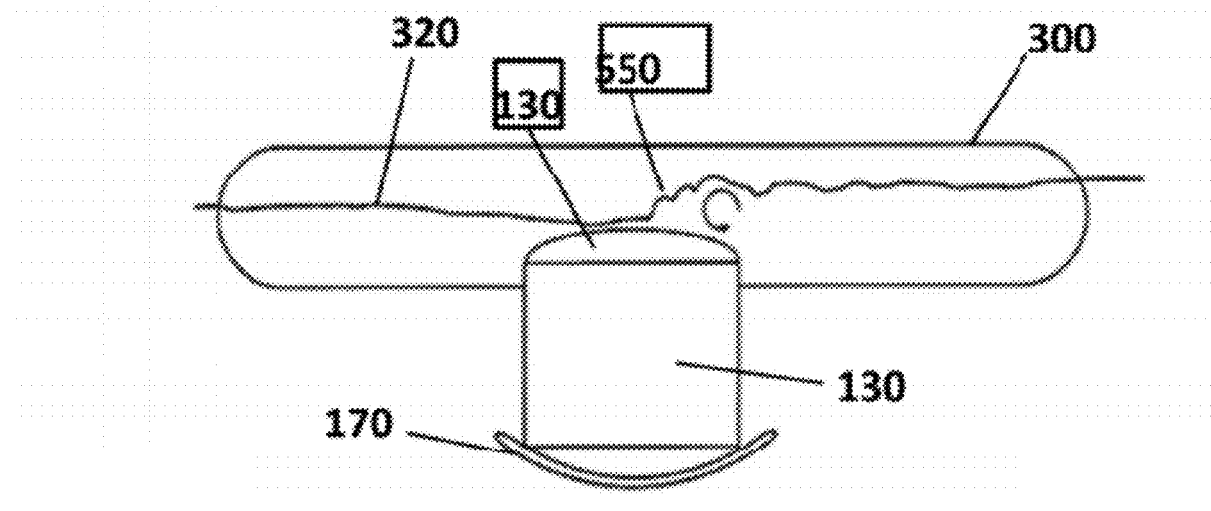

As illustrated in FIGS. 37A and B, agitation of the surface 320 can be enhanced by inducing a small hydraulic jump 550 by towing a foil 170 or a cambered horizontal support member 130 just below the surface 320 of the algae culture.

Figure 38:
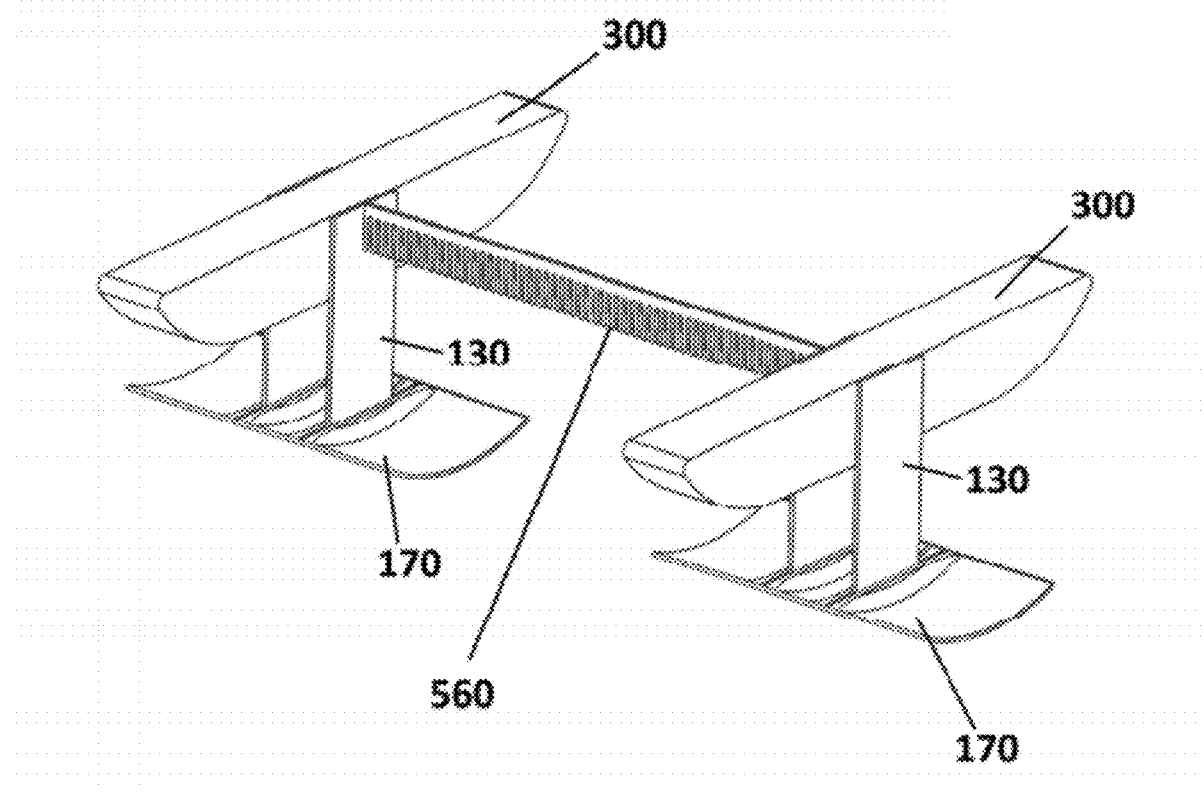
FIG. 38 shows foils, flotation members, support members and a surface agitating comb in accordance with certain embodiments of the present invention.

As illustrated in FIG. 38, in some embodiments, a surface agitating comb 560 or other suitable ancillary structure is attached to a horizontal support member 130 to agitate the surface 320 of the algae culture and increase gas transfer rates between vapor and liquid phases contained in a photobioreactor 310.

Figure 39:
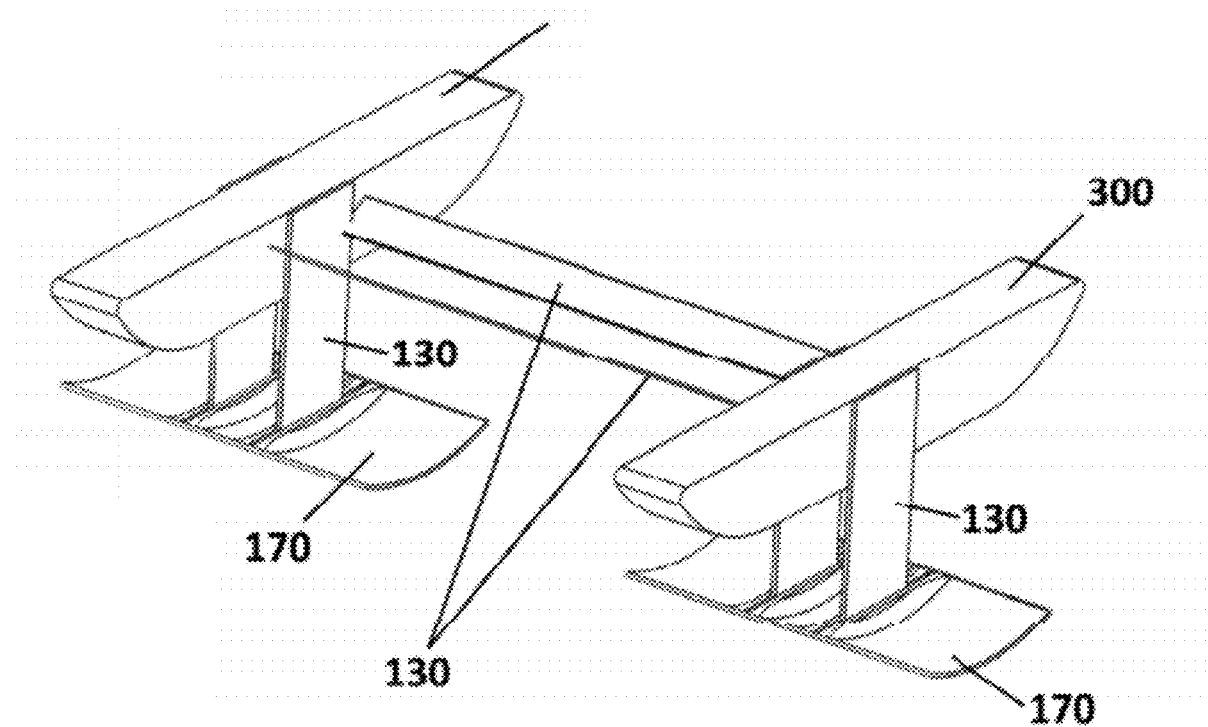
FIG. 39 shows foils, flotation members and support members in accordance with certain embodiments of the present invention.

As illustrated in FIG. 39, in some embodiments, one or more vertical support members 130 connecting a foil 170 to a flotation member 300 serve as rudders to prevent yaw. To be effective as steering devices, the foil 170 needs to pulled from a point forward of the center of pressure for the vertical support members 130 acting as rudders. A larger distance between the tow point and the center of pressure for the vertical support members 130 requires a stronger restoring force to align the foil 170 and counter any imbalance caused by imperfect foil 170 manufacturing, fouling from algae growth on the foil 170 or friction from contacting a surface of the photobioreactor 310. The vertical support members 130 additionally agitate the surface 320 of the algae culture.

In some embodiments, flotation members 300 and support members 130 are made from molded plastic, fiberglass, sintered nylon, glass-reinforced plastic, or any other material that is suitable to provide rigidity, durability, and positive or neutral buoyancy.

Figure 40:
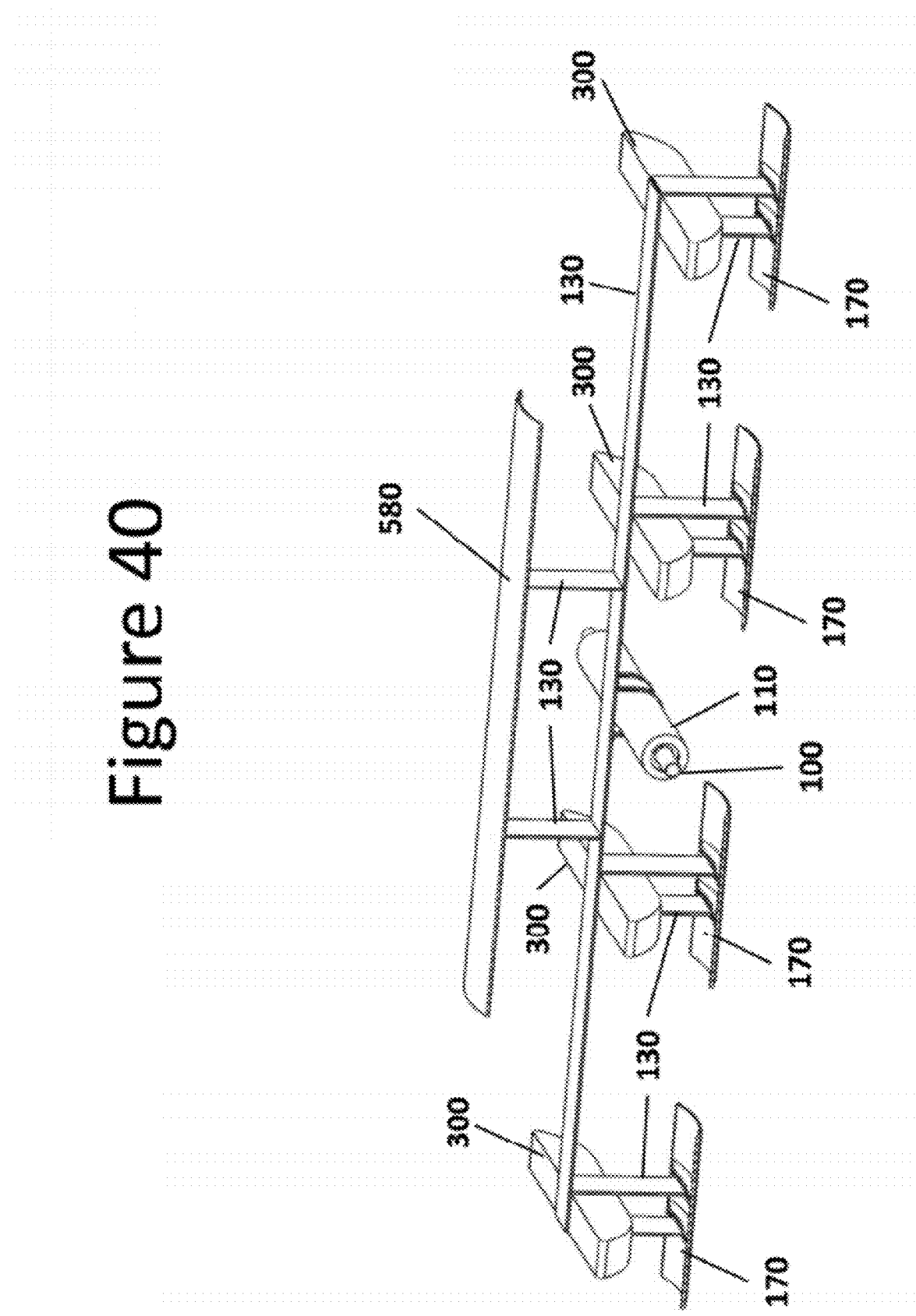
FIG. 40 shows a portion of a mixing system and an airfoil in accordance with certain embodiments of the present invention.

As illustrated in FIG. 40, in some embodiments, an airfoil 580 is positioned above the surface 320 of liquid in a photobioreactor 310. This configuration advantageously induces circulation of the vapor phase in the photobioreactor 310, which helps to increase the efficiency of a solar still by enhancing vapor transport from the surface 320 of the water to the walls of the photobioreactor 310.

In some embodiments, the longitudinal axis of the photobioreactor 310 or other mixing vessel is vertical. The drive conduit 100 likewise is vertically oriented, and the foil assembly 180 moves in a vertical direction along the drive conduit 100 and is fully submersed in the contents of the mixing vessel over at least a portion of the mixing vessel.

In some embodiments, the foil assembly 180 is used to skim the surface 320 of an open pond. The drive conduit 100 is positioned at or near the surface 320 of the pond, and the position and angle of attack of the foil 170 is adapted to maintain the foil 170 at or immediately beneath the pond surface 320.

In an exemplary embodiment, a gas sparging hose 700 is attached to a foil 170. Gas 702 may be pumped through the hose 700 and bubbled into the algae culture, with the outlet of the hose 700 located, for example, underneath the foil 170, near an edge of the foil 170 or immediately underneath the surface 320 of the algae culture. The hose 700 is adapted to move along the length of the photobioreactor 310 with the foil 170. Movement of the foil 170 creates shear in the algae culture near the lateral edges of the foil 170, which shears and reduces the size of the gas bubbles 702. Additionally, the gas bubbles 702 are entrained in the trailing vortices 330, which increases the residence time of the gas bubbles 702 in the algae culture and improves efficiency of mass transfer between the liquid phase of the algae culture and the gas phase present in the photobioreactor 310.

The hose 700 supplying the gas may be made of any suitable materials that are impermeable to the gas, that provide buoyance for the hose 700 to float on the surface 320 of the algae culture and that are sufficiently pliable to enable the hose 700 to fold or coil on the surface 320 of the algae culture. In some embodiments, a cage additionally is attached to the foil assembly 180 to capture slack in the hose 700 and prevent tangling.

In an exemplary embodiment, one or more Venturi tubes are incorporated in support members 130, with one opening of each Venturi tube disposed above the surface 320 of the algae culture and the opposite opening of each Venturi tube disposed below the surface 320 of the algae culture. The diameter of each Venturi tube may be, for example, approximately 1 to 2 millimeters.

As the foil 170 moves through the algae culture, a pressure gradient develops across the length of the Venturi tube. The pressure gradient pulls gas into the algae culture from above the surface 320 of the algae culture, creating small bubbles that are expelled into the algae culture. In some embodiments, Venturi tubes in the support members 130 are formed symmetrically to provide equivalent gas bubbling in each direction of longitudinal motion of the foil 170.

In an exemplary embodiment using pneumatic motive force to drive the drive element 190, the foils 170, support members 130 and other parts of the foil assembly 180 are omitted and only a follower element 110, which is magnetically coupled to the drive element 190, moves along the length of the drive conduit 100. When driven at high speeds, a cylindrical follower element 110 creates an air cavity in the shape of a bell behind the follower element 110 as it moves through the algae culture. The plunging jet of the liquid bell causes the formation of small bubbles in the algae culture, which increases mixing and mass transfer from the algae culture.

In some embodiments in which the foil assembly 180 is omitted, a gas sparging hose 700 is attached to the follower element 110. The hose 700 introduces gas bubbles 702 into the algae culture. The end of the hose 700 that is not attached to the follower element 110 may be connected to the photobioreactor 310 along the side in the center of the photobioreactor 310.

Mixing Operations

A mixing system in accordance with some embodiments of the present invention is capable of generating vertical mixing that is essential to the cultivation of algae in a photobioreactor 310 while minimizing capital investment and energy usage. In shallow depths with vertical recirculation, the necessary minimum vertical velocity needed to maintain a culture comprising certain strains of algae and to prevent visible sedimentation is approximately 20 to 30 seconds for turnover of algae in a circular cross section of six to eight inches contained in a culture having a depth of eight inches. For circulation rates that exceed this threshold, production in these systems increases only slightly, while energy consumption increases significantly.

Figure 41:
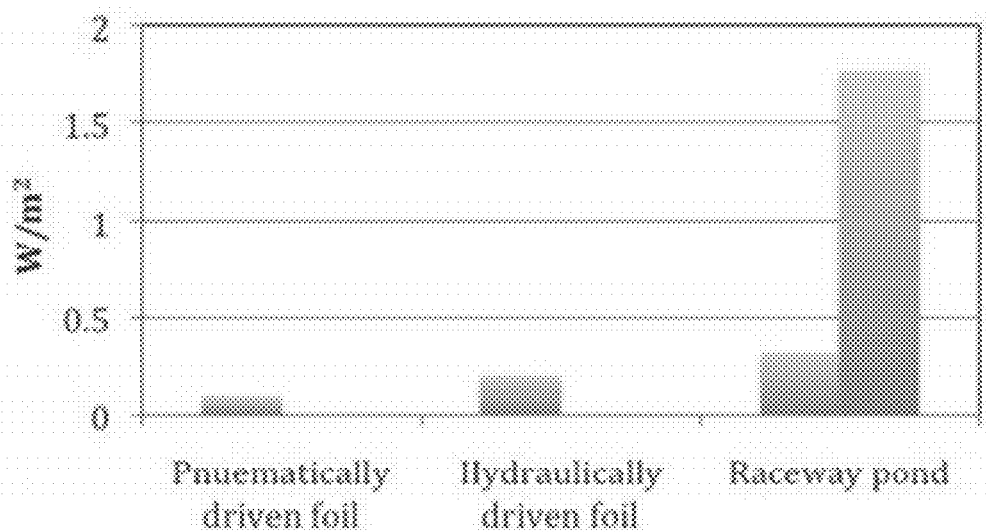
FIG. 41 shows a comparison of calculated energy requirements for mixing systems of the present invention with a mixing system known in the art.

FIG. 41 illustrates calculated energy requirements for mixing in a raceway pond system known in the art, as compared with energy requirements for certain embodiments of the present invention, to account for sliding friction, hydraulic and pneumatic losses and motor efficiency. The system of the present invention advantageously consumes energy at a lower rate while providing sufficient mixing of an aqueous algae culture. The smaller and larger columns for the raceway system represent, respectively, energy consumption required for 40 second and 20 second turnover times. This range of circulation tunes corresponds to the initial circulation time (20 seconds) after a foil assembly 180 passes through a static point in the mixing vessel and the decayed circulation time (40 seconds) immediately before the foil assembly 180 subsequently passes through the same point again, when the foil assembly 180 is towed at 0.5 meters per second.

A major distinction between rotary impeller motion known in the art and the linear foil 170 motion comprised by the present invention is the functionality and performance of the type of motion. Rotary impeller, or paddle wheel, motion is generally utilized to generate a directed flow, typically along the length or circumference of the vessel. Fluctuations in motion that are transverse to the selected direction of flow are chaotic and occur due to turbulence that is generated in the boundary layer of the vessel. Components of turbulence that are not directed vertically and do not contribute to vertical transport, which is important in the embodiment of a photobioreactor 310 where light is received from overhead, are nonetheless generated. The chaotic vertical motion and extra fluctuation components thus make this rotary motion energetically inefficient for bulk vertical transport.

The efficiency of vertical transport may be increased by placing foils 170 in a stream (as taught by Laws et al.) to induce vertical recirculation. However, the majority of flow kinetic energy is still dissipated through overcoming boundary friction in sustaining the relative motion required.

In accordance with embodiments of the present invention, by moving the foil 170 in a linear path through an algae culture contained in a photobioreactor 310 or other mixing vessel, the problem of dissipation of flow kinetic energy is overcome. The decay of recirculation, which is created by passing a foil 170 through the algae culture in a linear path to generate trailing vortices 330, is also ameliorated by repeatedly passing the foil 170 through the same path to continually reinforce the vortices 330.

Vertical mixing systems known in the art may be compact, at the expense of elevated energy consumption. In accordance with embodiments of the present invention, components of the vertical mixing system may be manufactured from lightweight materials, such as plastics, which can help minimize capital expenditures and energy consumption for the system.

Figure 42:
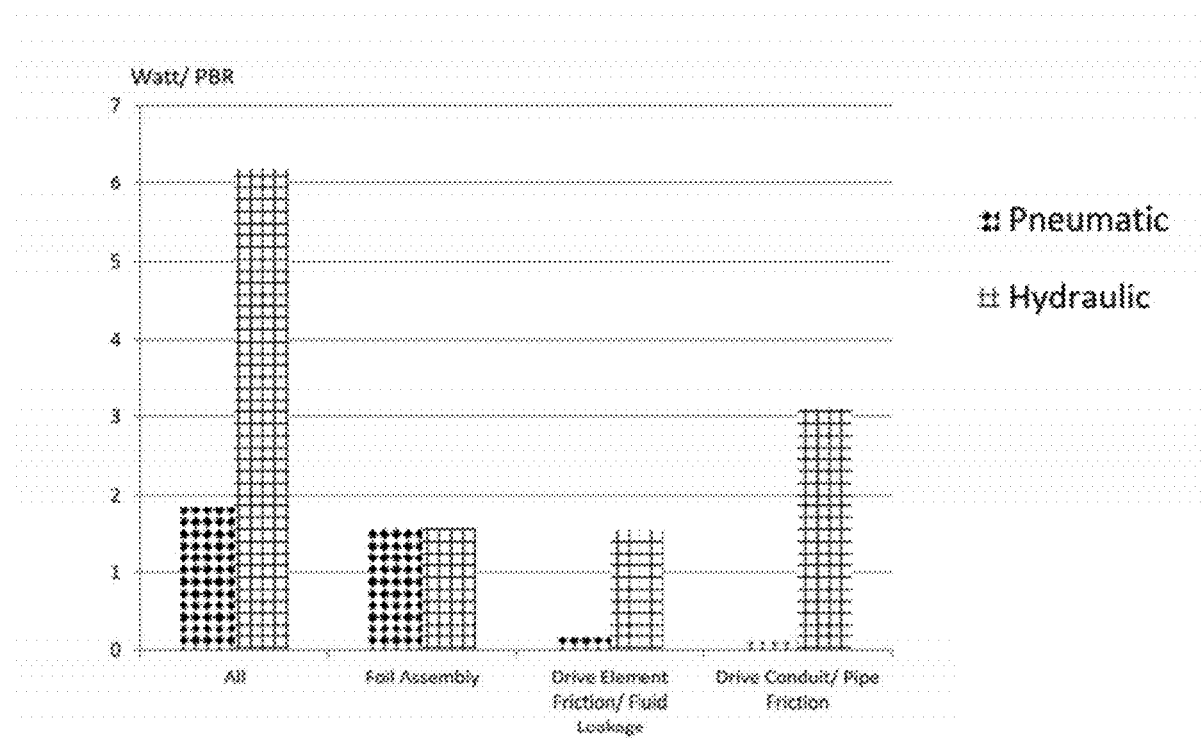
FIG. 42 shows a comparison of energy consumption in pneumatic and hydraulic mixing systems in accordance with certain embodiments of the present invention.

FIG. 42 details energy in pneumatic and hydraulic mixing systems of the present invention. In the exemplary embodiment, the pneumatic mixing system uses air and the hydraulic mixing system uses water. Consumption data attributable to drive element friction/fluid leakage and to drive conduit/pipe friction are specific to the motive force used in each mixing system. Drive element friction/fluid leakage indicates energy loss due to friction between the outer surface of the drive element 190 and the inner surface of the drive conduit 100, in conjunction with head loss due to fluid leaking past the drive element 190 inside the drive conduit 100. Drive conduit/pipe friction indicates energy loss due to friction as the drive fluid flows through the pipes 410 and drive conduit 100 of the mixing system. FIG. 42 illustrates that combined drive element friction/fluid leakage and drive conduit/pipe friction are substantially lower for the pneumatic mixing system than for the hydraulic mixing system.

In FIG. 42, foil assembly indicates energy consumption attributable to hydrodynamic drag on the foil assembly 180 moving through the algae culture, which is independent of the drive system used. Comparison of total energy consumption and energy losses attributable to each category shows that a substantially higher proportion of energy is translated directly to moving the foil assembly 180 using the pneumatic mixing system than using the hydraulic mixing system.

In some embodiments, a mixing system of the present invention is used to agitate algae culture in a photobioreactor 310 intermittently. According to the present invention, intermittent operation of the mixing system provides sufficient vertical mixing while economizing energy consumption.

In exemplary embodiments, mixing systems of the present invention are used to agitate only portions of algae culture contained in a photobioreactor 310. In some embodiments, horizontally oriented foils 170 generate trailing vortices 330 that agitate the algae culture from the surface 320 to a depth that is less than the total depth of the algae culture. The span of each foil 170 may be less than the total depth of the algae culture, so that the foil 170 generates trailing vortices 330 having diameters less than the depth of the algae culture 113. Lateral spacing between foils 170 may be greater than the span of each foil 170.

In some embodiments, vertically oriented foils 170, each having a span less than the depth of the algae culture, agitate the algae culture from the surface 320 to a depth that is less than the total depth of the algae culture.

In some embodiments, the foil assembly 180 traverses only a portion of the length of the photobioreactor 310, agitating the algae culture contained in that portion while leaving the algae culture in the remaining portion of the photobioreactor 310 unmixed.

Example 1

Both hydraulic and pneumatic drive fluids have been used to propel a magnetically coupled foil assembly 180 through a photobioreactor 310 at 0.5 meters per second. In a preferred embodiment, the foil assembly 180 traverses the 50 foot length of a commercial scale photobioreactor 310 at 0.5 meters per second for a defined time interval (usually 30 seconds) before the foil assembly 180 reverses direction of motion. The minimum steady state power requirement for motion of a foil assembly 180 according to these specifications has been determined by measuring fluid pressures and flow rates while the foil assembly 180 moves at a constant speed. This determination neglects any additional energy consumption or efficiency that occurs during the few seconds when the foil assembly 180 is moving at less than 0.5 meters per second while reversing direction of motion.

Using hydraulic drive fluid and a drive ferromagnet 144, measurements indicate a pressure drop of 8 to 9 pounds per square inch per photobioreactor 310 at a fluid flow rate of 2 gallons per minute. Without accounting for pump 420 and drive efficiency, the minimum power requirement using water as a drive fluid is determined by Equation 1:

$$\text{Power}_{min} = \Delta \text{Pressure} \times \text{Flowrate} = 7.8 \text{ Watts per photobioreactor 310}$$

which is equivalent to 0.34 Watts/m$^2$ for a 23 m$^2$ photobioreactor 310.

Power requirements have not varied in photobioreactors 310 containing either freshwater, seawater or algae culture. Accordingly, power consumption by mixing systems of the present invention used in liquid not containing algae culture is substantially equivalent to power consumption by mixing systems of the present invention used in liquid containing algae culture. According to the present invention, drag on the foil assembly 180 is mostly due to inertial forces, rather than viscous forces, and the densities of all fluids tested in the photobioreactor 310 are roughly equivalent.

A preponderance of power loss in mixing systems of the present invention that use hydraulic drive fluid were attributable to fluid leakage past the drive ferromagnet 144 and the resulting increased pressure drop to force the hydraulic fluid, typically water, through the drive conduits 100 and pipes 410. Using a pneumatic drive fluid significantly reduced pressure drop over the drive ferromagnet 144 due to the lower viscosity of gas, typically air, compared to water and other fluids and due to the use of seals to reduce fluid leakage past the drive ferromagnet 144. Thus, mixing systems of the present invention that incorporate a floating pneumatic seal around the drive ferromagnet 144 and use lubricated air typically have operated at 3 to 4 pounds per square inch at 5 to 6 standard liters per minute.

Four pneumatically driven mixing systems have been operated outdoors with 6.16±6% standard liters per minute of air consumed by each (referenced at 25 degrees Celsius) under 2.75±0.05 pounds per square inch. Using the standard equation for calculating the power required to compress gas adiabatically, the minimum energy requirement is thus 1.82 Watt/photobioreactor 310, or 0.08 Watts/m$^2$.

Net energy usage for a commercial mixing system of the present invention to power 240 photobioreactors 310, based on distribution losses of 5%, a compressor of 50% efficiency and an electrical drive of 90% efficiency yields a minimum energy requirement of 4.26 Watts/photobioreactor 310, or 0.185 Watts/m$^2$. An array of 240 photobioreactors 310, as illustrated in FIG. 23, would require the use of a rotary lobe compressor rated at 1.5 horsepower. A commercial plant with a centralized compressor system may utilize a more efficient compressor to reduce the power requirements. It is also possible to use bleed air from the first compression stages of a power generating gas turbine as the pneumatic drive fluid, which may reduce net energy cost if the efficiency of conversion of fuel energy to electricity is considered.

The energy required to run a pneumatically driven foil assembly 180 is roughly equivalent to that required for a large raceway system running at 0.25 meters per second, with an 8 inch algae culture depth. The net power requirements for both systems are approximately 0.2 Watts/m$^2$. Thus, the operating expense for both systems is $1230 per hectare per year assuming an energy cost of $0.07 per kilowatt hour. The operating expense is higher for small raceway systems, however. One major manufacturer of raceway paddlewheels (Waterwheel Factory, Inc.) estimates that motors rated for at least 20-40 Watts would be required to provide mixing in photobioreactors 310 measuring 5 feet by 50 feet under the most optimistic conditions, which is a factor of 5-10 times higher power requirement than the exemplary foil mixed systems.

Example 2

Growth of cyanobacteria in response to mixing was compared in two reactor types that varied in mixing system design. Two closed foil-mixed photobioreactors and two closed flume-style raceway pond photobioreactors were tested. The oval-shaped raceway pond photobioreactors and the foil-mixed photobioreactors were constructed and enclosed using the same thin, flexible polymeric film.

Inoculum cultures of a unicellular cyanobacterium were scaled in 50-liter flat-panel culture vessels. The inoculum cultures were then transferred into the two raceway pond photobioreactors and the two foil-mixed photobioreactors containing seawater and BG-11 nutrient mix. Each raceway pond photobioreactor contained approximately 460 liters of seawater and each foil-mixed photobioreactor contained approximately 900 liters of seawater. Sunlight entered each reactor across the top surface only, and the culture depth in each reactor was 8 inches (20 centimeters), yielding equal surface area to volume ratios for the four reactors. The seawater in each photobioreactor was pre-filtered to 0.2-μm and had salinity of 35.

Air was delivered to each photobioreactor at a rate of 5 liters per minute, and carbon dioxide was added from 08:00 to 18:00 local standard time, controlled to a volumetric ratio of 10% carbon dioxide to air. Each photobioreactor was maintained under ambient irradiance and temperature conditions.

The culture contained in each foil-mixed photobioreactor was mixed using a foil assembly comprising four foils positioned at a depth of four inches in the algae culture contained in the photobioreactor. Each foil had a span of seven inches and a chord of four inches. The foils were spaced with their centerlines 14 inches apart.

The foil speed traversing the length of the foil-mixed photobioreactor was maintained at 0.5 meters per second while the foil was in motion. When the foil reached each end of the photobioreactor, the motion of the foil was paused for 20 to 22 seconds in order to simulate the period of the foil, and thus vortex reinforcement frequency, in a 50 foot-long commercial-scale, foil-mixed photobioreactor.

Each raceway photobioreactor was operated similarly to a paddlewheel raceway in which horizontal motion of culture was maintained through pumping and recirculation of the flow. Rather than using a paddlewheel, however, pumping in the raceway photobioreactors was accomplished using four Tunze® Turbelle® stream 6085 pumps in each bioreactor. These are propeller pumps with a 90 mm (3.5 in.) ball design generally used for water circulation in aquariums or tanks. Each Tunze® Turbelle® stream 6085 produces flow rate of about 8 liters per hour at power consumption of about 14 Watts, but the particular power consumption of these pumps is of secondary importance. Rather, the horizontal flow that they produced in the raceway photobioreactor was the target. The pumps were arranged to provide a flow rate of 0.25 m/s in an 8 inch (20 cm) deep culture in the photobioreactor raceways. This flow rate was calculated following Weissman et al., "Photobioreactor Design: Mixing, Carbon Utilization, and Oxygen Accumulation," Biotechnology and Bioengineering, Vol. 31, Pp. 336-344 (1988), equating the electrical energy consumption of a commercial scale paddlewheel system to generate this flow (0.21 Watts/square meter) to the power to drive the pneumatic foil system. The power requirement was determined using Manning's equation for hydraulic loss. Drive efficiency was estimated as 0.31 for a paddlewheel operating at the specified speed and depth on a 100 square meter raceway. The drive efficiency could be as high as 0.5 for a very large system, but the increased efficiency would not significantly increase the flow rate, i.e., to 0.28 meters per second, under the stated power consumption. Raceway reactors are also typically operated at mixing speeds of 0.15-0.25 meters per second to minimize settling of algae in the culture.

As shown in Table 1, volumetric dry weight of the unicellular cyanobacterium in each algae culture was measured for each photobioreactor three times per week for three weeks, as each culture matured from growth phase to early stationary phase. Dry weight areal biomass of the unicellular cyanobacterium in each algal culture, shown in Table 1, was calculated based on measured culture volumes and the surface areas of the culture in each photobioreactor, shown in Table 2.

TABLE 1

| Time | Raceway PBR 1 | | Raceway PBR 2 | | Foil Mixed PBR 1 | | Foil Mixed PBR 2 | |
| --- | --- | --- | --- | --- | --- | --- | --- | --- |
| (day) | mg/L | g/m$^2$ | mg/L | g/m$^2$ | mg/L | g/m$^2$ | mg/L | g/m$^2$ |
| 0.7 | 59.33 | 11.67 | 14.67 | 2.98 | 57.26 | 12.02 | 62.07 | 13.35 |
| 2.4 | 85.83 | 16.88 | 72.50 | 14.75 | 67.70 | 14.22 | 97.22 | 20.90 |
| 4.4 | 218.52 | 42.98 | 209.63 | 42.66 | 209.63 | 44.02 | 194.81 | 41.89 |
| 7.3 | 380.00 | 74.73 | 351.11 | 71.45 | 455.56 | 95.67 | 443.33 | 95.32 |

TABLE 1-continued

| Time | Raceway PBR 1 | | Raceway PBR 2 | | Foil Mixed PBR 1 | | Foil Mixed PBR 2 | |
|---|---|---|---|---|---|---|---|---|
| (day) | mg/L | g/m² | mg/L | g/m² | mg/L | g/m² | mg/L | g/m² |
| 10.3 | 397.64 | 78.20 | 435.56 | 88.64 | 513.33 | 107.80 | 475.56 | 102.24 |
| 11.3 | 379.17 | 74.57 | 369.44 | 75.18 | 433.33 | 91.00 | 419.44 | 90.18 |
| 14.4 | 390.00 | 76.70 | 460.00 | 93.61 | 466.67 | 98.00 | 490.00 | 105.35 |
| 16.3 | 425.00 | 83.58 | 460.00 | 93.61 | 580.00 | 121.80 | 536.67 | 115.38 |
| 18.3 | 420.00 | 82.60 | 540.00 | 109.89 | 660.00 | 138.60 | 636.67 | 136.88 |
| 21.3 | N/A | N/A | N/A | N/A | 587.73 | 123.42 | 541.67 | 116.46 |

TABLE 2

| Reactor | SA (m²) | Volume (L) |
|---|---|---|
| Raceway PBR 1 | 2.31 | 454 |
| Raceway PBR 2 | 2.31 | 470 |
| Foil Mixed PBR 1 | 4.23 | 889 |
| Foil Mixed PBR 2 | 4.31 | 926 |

The logistic growth model stated in Equation 2 (Kot, "Elements of Mathematical Ecology", Cambridge University Press (2001)) was parameterized from the areal data in each photobioreactor as listed in Table 1.

$$B(t) = \frac{K B_0 e^{\mu t}}{K + B_0(e^{\mu t} - 1)} \quad \text{Equation 2}$$

wherein
t=time (day);
μ=specific growth rate (1/day);
$B_0$=initial biomass (g-DW/m²); and
K=biomass abundance at stationary phase (g-DW/m²).

Values of the parameters in Equation 2 obtained from non-linear least square fit of the logistic growth model to the data in Table 1 are shown in Table 3:

TABLE 3

| PBR | μ | K | Max. Growth Rate (g/m²/d) | R² |
|---|---|---|---|---|
| Raceway PBR 1 | 0.6741 | 79.97 | 13.4783 | 0.987 |
| Raceway PBR 2 | 0.4740 | 96.14 | 11.3931 | 0.952 |
| Foil Mixed PBR 1 | 0.4911 | 117.81 | 14.4658 | 0.922 |
| Foil Mixed PBR 2 | 0.4307 | 116.90 | 12.5867 | 0.935 |
| p value | 0.3921 | 0.069 | 0.519 | |
| t-stat* | 1.083 | −3.618 | −0.777 | |
| Significant? | No | Yes (90%) | No | |

*2-tailed t-test

Figure 43:
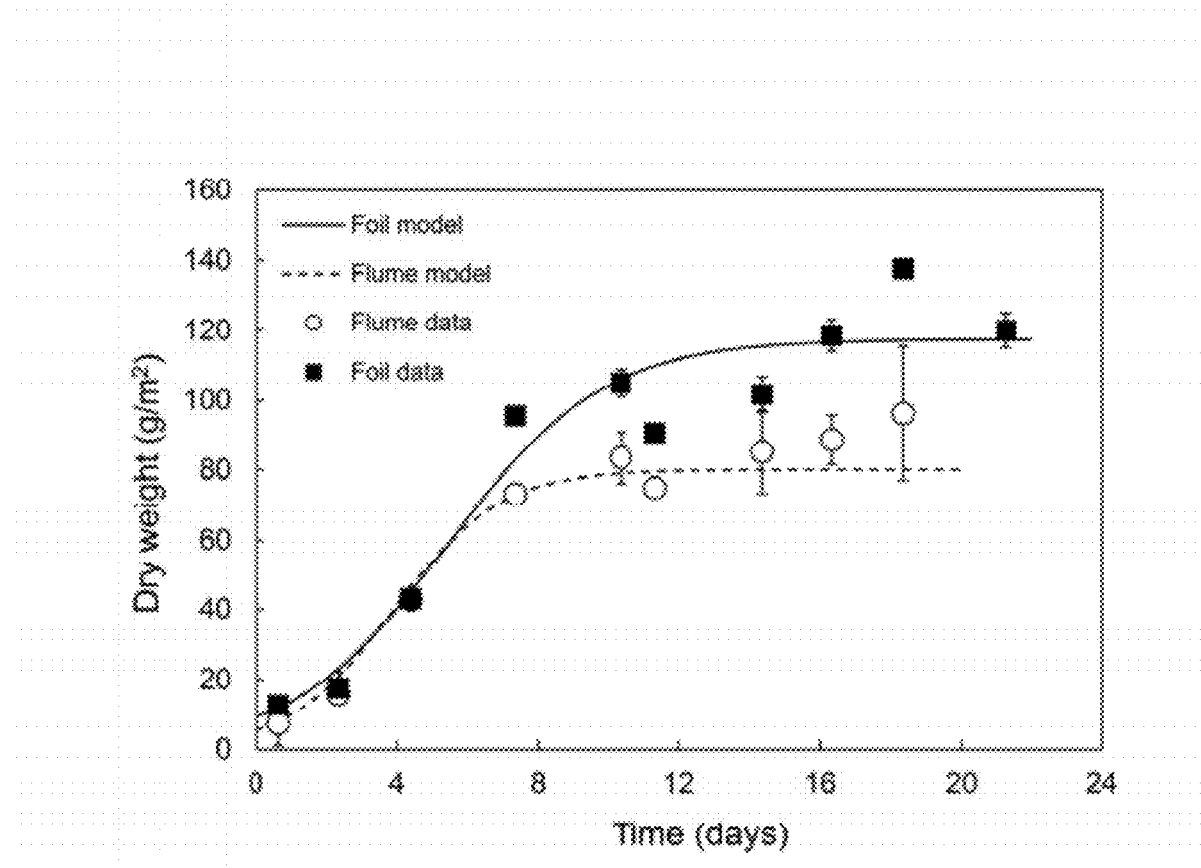
FIG. 43 shows an exemplary graphical representation of the dependence of biomass accumulation on mixing type in closed photobioreactors.

Plots of the average dry weight areal biomass data for each replicate photobioreactor type in Table 1 and the parameterized logistic growth models in Equation 2 for averaged data from both reactor types are overlain in FIG. 43. If an exponential model of growth is assumed instead of a logistic model and specific growth, μ, is calculated as $\ln(B_2/B_1)/(t_2-t_1)$, where $t_1$=2.4 days and $t_2$=7.3 days, then specific growth rates average 0.343±0.055 and 0.307±0.013, respectively to foil-mixed and raceway PBRs, and are not significantly different (t-test stat=0.8969, p=0.4644).

As shown in Table 4, both measured and modeled cumulative biomass growth at day 16 are significantly greater in the foil-mixed photobioreactors than in the raceway photobioreactors:

TABLE 4

| 16-day cumulative biomass growth (g/m²) | | | | |
|---|---|---|---|---|
| | Measured Cum. Growth (g/m²) | | Modeled Cum. Growth (g/m²) | |
| Reactor | Mean | Std. Dev. | Mean | Std. Dev. |
| Foil Mixed PBRs | 118.6 | 4.5 | 116.5 | 1.01 |
| Raceway PBRs | 88.6 | 7.1 | 87.5 | 10.7 |
| t-stat | 5.0375 | | 3.6612 | |
| p value | 0.0372 | | 0.0672 | |
| Significant? | Yes (95%) | | Yes (90%) | |

Example 3

Capital expense is compared for conventional mixing technology using paddlewheels to mix shallow algae cultures and for a mixing system in accordance with the present invention using a magnetically coupled, moving foil assembly. Details of the capital expense for large scale paddlewheel systems have been published in Weissman et al. Two paddlewheel systems described therein are adapted for 0.4 hectare and 8 hectare ponds. The paddlewheel mixer capital expense totals adjusted to present day values are approximately $11,000 and $36,000 for the 0.4 hectare and 8 hectare ponds, respectively. As noted in Table 5, these capital expense totals are equivalent to approximately $53,000 and $9,000 per hectare, respectively.

TABLE 5

| 5 × 50 ft reactor area (23 m²) | | |
|---|---|---|
| Component | Open channel | Sealed Film Photobioreactor |
| center barrier | | $ 116 |
| paddlewheel | $ 37 | $ 37 |
| support | | |
| guard poles | | $ 2 |
| flange | $ 40 | $ 40 |
| bearings | | |
| lip seals | | $ 40 |
| paddlewheel | $ 22 | $ 22 |
| shaft 3/8 SS | $ 45 | $ 45 |
| end fairings | | $ 15 |
| gear motor | $ 40 | $ 40 |
| Capex/PBR | $ 184 | $ 356 |
| Capex/hectare | $80,122 | $154,966 |
| Industrial scale raceway ponds Weissmann & Goebel 1987* | | |
| Capex/hectare | $52,770 | (0.4 hectare) |
| Capex/hectare | $ 8,850 | (8 hectare) |

*Cost adjusted for 2011

An independent estimate for the lowest cost of a paddlewheel mixing system suitable for use in an open 23 square meter (0.0023 hectare) raceway pond, which is equivalent to the typical size of an enclosed bioreactor measuring 5 feet by 50 feet, was determined by estimating the lowest material costs for a design provided by Waterwheel Factory, Inc., a major waterwheel manufacturer. The estimated material costs are shown in Table 2.

At $184 per raceway photobioreactor, the capital expense per hectare for a small-scale paddlewheel mixing system is approximately $80,000 per hectare. This estimate is plotted in FIG. 44 along with historical published data. As show by the dotted line plotted in FIG. 44, there is a trend toward increased capital expense per area with smaller raceway systems.

The capital expense for a foil mixing system in accordance with the present invention used with a 23 square meter enclosed photobioreactor is detailed in Table 6.

TABLE 6

| Component | Specification | feet of piping | lb/ft[1] | $/ft[2] | total cost |
|---|---|---|---|---|---|
| header piping (central row) | 1.5" SDR11 | 610 | 0.41 | 0.492 | $ 300 |
| header piping (sides) | 1.25" SDR15.3 | 1420 | 0.16 | 0.192 | $ 273 |
| mixer tubing | ½" SDR10.1 | 12,480 | 0.048 | 0.0576 | $ 719 |

| | | quantity | $/item | | |
|---|---|---|---|---|---|
| compressor | 1.5 hp rotary lobe blower | 1 | 1000 | | $ 1,000 |
| electronics and control | ABB VFD or 4-way valve | 1 | 350 | | $ 350 |
| external magnets | NdFeB Grade N42 1.25"OD × 0.75" ID × ⅛" | 240 | 6.4 | | $ 1,536 |
| internal magnets | NdFeB Grade N40 0.5"OD × 0.25" ID × ¼" | 480 | 2.37 | | $ 1,138 |
| mixer[3] | 2 lbs HDPE | 240 | 4.38 | | $ 1,051 |
| | | | | cost/module[4] | $ 6,366 |
| | | | | cost/PBR[5] | $ 27 |
| | | | | cost/hectare | $11,533 |

[1]Performance Pipe IPS size data for PE 4710.
[2]$1.20/lb in accord with pricing from Ferguson Enterpries, Inc.
[3]Cost calculated by 3X cost of plastic for standard blow molding, $0.73/lb in accord with ICIS pricing.
[4]1 module consists of 240 photobioreactors arranged as in FIG. 23.
[5]Each photobioreactor is 5 feet wide by 50 feet long and has a wet area of 23 square meters.

The capital expense illustrated in Table 6 includes the drive and distribution components of the pneumatic chive foil mixing system for a set of 240 photobioreactors (in 4 rows of 60). Here, the capital expense per bioreactor is $27, or approximately $11,500 per hectare. Thus, the capital expense per area for a facility constructed using photobioreactor modules of this size is independent of the size of the facility.

Figure 44:
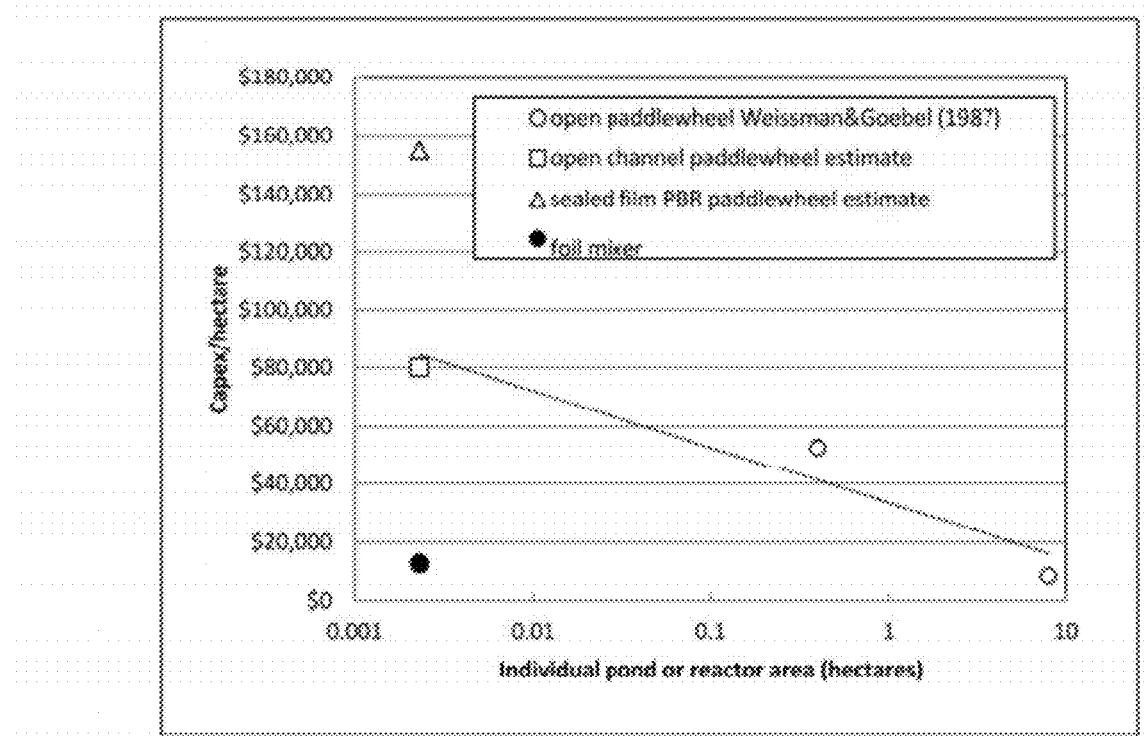
FIG. 44 shows an exemplary graphical representation of capital expenditure per hectare for different mixing systems.

Capital expense is compared for foil mixing systems and raceway mixing systems in Table 7 and FIG. 44.

TABLE 7

| | individual reactor size (hectare) | Capex/hectare |
|---|---|---|
| open paddlewheel Weissman&Goebel (1987) | 8 | 8,848 |
| open paddlewheel Weissman&Goebel (1987) | 0.4 | 52,772 |
| open channel paddlewheel estimate | 0.0023 | 80,122 |
| sealed film PBR paddlewheel estimate | 0.0023 | 154,966 |
| foil mixer | 0.0023 | 11,533 |

The data in Table 7 and FIG. 44 show that the currently sized foil mixing system is approximately one order of magnitude less expensive than raceway paddlewheel mixing systems on an areal basis, except for raceways which approach a size of 8 hectares. Thus, foil mixing reduces the capital cost of mixing on all scales which can be enclosed at reasonable expense. Even if the cost to enclose a 0.4 hectare (approximately 1 acre) pond was negligible, foil mixing systems are still 4.5 times less expensive than raceway paddlewheel mixing systems. The cost for a sealed raceway system would exceed the estimates shown in Table 6 due to the cost of seals, guards, central barriers and end pieces that would need to be manufactured for the photobioreactors.

The foregoing Examples 1 through 3 demonstrate that the biomass output of a foil mixed system was comparable or better than a raceway pond, while the operating expense of the foil system was equivalent or lower. The most distinctive advantage of the foil mixed system is its low capital expense, which makes up a large fraction of the total cost even when spread over a 15 year operating period as shown in Table 8. Capital expense is a much larger fraction of the total expense for the paddlewheel raceway systems for areas that are practical to enclose (e.g. 23 square meters). Thus the total cost of mixing to generate biomass is much higher in the paddlewheel system, by a factor as large as 8. Here the cost of mixing is only about 4 cents per kilogram of dry weight, while cost of mixing for an enclosed paddlewheel system could be 34 cents per kilogram.

TABLE 8

| Annual expenditure/hectare | Pneumatically driven foil mixed reactors (23 sq. m) | Enclosed paddlewheel reactors (23 sq. m) |
|---|---|---|
| Capex/15 years[1] | 769 | 10,331 |
| Opex | 1,230 | [(2)]5,775 |
| Total | 1,999 | 16,106 |
| Biomass yield per year[3] | 47,450 | 47,450 |
| Total cost[4] ($/kg of biomass) | 0.042 | 0.339 |

[1]Interest on loan not considered in either case.
[(2)]20 Watts per photobioreactor as the minimum suggested by Waterwheel Factory, Inc. for 0.25 meters per second flow.
[3]Assuming maximum growth rate (13 grams per square meter per day) demonstrated in Example 2 is sustained over a year.
[4]Considering only the cost of mixing.

In certain embodiments, as illustrated in FIGS. 46, 47 and 48, the depth of the algae culture is shallow and a crossbar 590 is used to create a shallow breaking wave front 600 on the surface 320 of the algae culture. In certain embodiments, the depth of the algae culture is preferably approximately 1 to 2 inches. In certain embodiments, the depth of the algae culture is preferably approximately 1 inch. The crossbar 590 is attached to a follower element 110 that is disposed on a drive conduit 100. The crossbar 590 is propelled using magnetic coupling between the follower element 110 and a drive element 190, to which pneumatic or hydraulic motive force is applied.

The crossbar 590 is propelled at sufficient speed to displace fluid along the length of the photobioreactor 310, such that a wave front 600 is generated that moves at a higher speed than the shallow water wave in the direction of travel of the crossbar 590. For an algae culture of 1 inch depth, a wave front 600 may be generated by a crossbar traveling at 0.5 meters per second.

The wave front 600 generated at the surface 320 of the algae culture provides enhanced mass transfer between the liquid algae culture and the air above the surface 320 of the algae culture. Dissolved oxygen content in the algae culture would be lower when a breaking wave front 600 is generated than when a breaking wave front 600 is not generated in the algae culture. The wave front 600 also generates provides vertical mixing of the algae within the culture, which enhances photosynthetic productivity and diffusion of nutrients.

The range of traverse, or stroke length, of the crossbar 590 may be substantially shorter than the length of the photobioreactor 310. Stroke length can be controlled by placing stoppers inside the drive conduit 100 to restrict the motion of the drive element 190 or around the outside of the drive conduit 100 to restrict the motion of the follower element 110. In one embodiment, a stroke length of 1 meter is sufficient to generate a wave front 600 that can propagate for 80% of the length of the photobioreactor 310. Shorter stroke length of the wave front 600 produces shorter propagation distance of the wave front 600.

A wave front 600 can be created in a photobioreactor 310 that is 50 feet long using 8.5-9.5 pounds per square inch hydraulic motive force in a drive conduit 100 of 0.52 inches inside diameter, which propels the crossbar 590 at 0.33-0.5 meters per second. If the crossbar 590 is located in the center of the photobioreactor 310, a cycle time of approximately 10 seconds for the crossbar 590 to complete one oscillation allows for one breaking wave front 600 to be present on either side of the crossbar 590 at any time, while maintaining low energy usage, approximately 4 Watts per photobioreactor 310, equivalent to a mixing system using a foil assembly 180.

The crossbar 590 used to generate a wave front 600 may be buoyant and may have chamfered edges on the lower surfaces of the crossbar 590 to generate lift, which prevents the crossbar 590 from touching the bottom of the photobioreactor 310 and reduces friction and wear on the components of the crossbar 590 and the photobioreactor 310. The crossbar 590 will be optimally designed such that reflections of the wave front 600 are minimized. The wave front 600 preferably dissipates when it reaches the end of the photobioreactor 310 and does not disrupt the motion of the crossbar 590. Resonant operation of the crossbar 590 is possible but may be difficult to control at low capital expense.

Multiple crossbars 590 in one photobioreactor 310 can be driven in the same manner as a system using multiple foil assemblies 180. In combination with reducing the stroke length of each crossbar 590, a configuration employing multiple crossbars 590 can be used to generate wave fronts 600 at higher frequencies, so that more than two breaking wave fronts 600 would be present in the photobioreactor 310 at any time.

Although the present invention has been described in considerable detail with reference to certain embodiments thereof, other embodiments are possible. Therefore, the spirit and scope of the appended claims should not be limited to the description of the embodiments contained therein.

What is claimed is:

1. A magnetically coupled mixing system comprising:
   a mixing vessel;
   a liquid disposed within the mixing vessel, wherein the liquid partially fills the mixing vessel creating a to surface of the liquid;
   a drive conduit, wherein the drive conduit is disposed floating in the liquid at the to surface of the liquid;
   a drive element disposed within the drive conduit and adapted to move within the drive conduit in a longitudinal direction parallel to the to surface of the liquid; and
   a magnetic follower element disposed at least partially within the liquid and around the perimeter of at least a portion of the drive conduit and adapted to move longitudinally along the drive conduit, wherein the magnetic follower element is adapted to couple magnetically with the drive element and is proximally disposed outside the drive conduit.

2. The magnetically coupled mixing system of claim 1 further comprising a gas supply and a hose adapted to sparge gas from the gas supply into the liquid disposed within the mixing vessel, wherein the hose comprises a first end attached to the magnetic follower element and a second end, wherein gas from the gas supply is sparged through the first end of the hose into the liquid.

3. The magnetically coupled mixing system of claim 2 wherein the second end of the hose is attached to the mixing vessel.

4. The magnetically coupled mixing system of claim 1 further comprising a drive fluid contained within the drive conduit and a pump in communication with the drive conduit, wherein the pump is adapted to move the drive fluid and the drive element within the drive conduit and wherein the drive fluid is air, water, mineral oil, polyethylene glycol or hydraulic fluid.

* * * * *

UNITED STATES PATENT AND TRADEMARK OFFICE
CERTIFICATE OF CORRECTION

PATENT NO.        : 8,398,296 B2
APPLICATION NO.   : 13/405012
DATED             : March 19, 2013
INVENTOR(S)       : Harlan Miller, III et al.

It is certified that error appears in the above-identified patent and that said Letters Patent is hereby corrected as shown below:

In the Specifications:

Column 1, Line 3, please insert the following paragraph after the title of the invention:

--STATEMENT REGARDING FEDERALLY SPONSORED RESEARCH

[0001] This invention was made in part with United States government support under the Department of Energy grant number DE-EE0002867. The government has certain rights in this invention.--

In the Claims:

Claim 1, Column 34, Line 21, please delete the word "to" and insert the word --top--.

Claim 1, Column 34, Line 24, please delete the word "to" and insert the word --top--.

Claim 1, Column 34, Line 27, please delete the words "the to" and insert the words --the top--.

Signed and Sealed this
Twenty-third Day of April, 2013

Teresa Stanek Rea
*Acting Director of the United States Patent and Trademark Office*